(12) United States Patent
Kawakami et al.

(10) Patent No.: US 8,835,018 B2
(45) Date of Patent: *Sep. 16, 2014

(54) ORGANIC COMPOUND, ANTHRACENE DERIVATIVE, AND LIGHT-EMITTING ELEMENT, LIGHT-EMITTING DEVICE, AND ELECTRONIC DEVICE IN WHICH THE ANTHRACENE DERIVATIVE IS USED

(75) Inventors: Sachiko Kawakami, Kanagawa (JP); Nobuharu Ohsawa, Kanagawa (JP)

(73) Assignee: Semiconductor Energy Laboratory Co., Ltd., Kanagawa-ken (JP)

( * ) Notice: Subject to any disclaimer, the term of this patent is extended or adjusted under 35 U.S.C. 154(b) by 1200 days.

This patent is subject to a terminal disclaimer.

(21) Appl. No.: 12/055,000

(22) Filed: Mar. 25, 2008

(65) Prior Publication Data
US 2008/0268284 A1    Oct. 30, 2008

(30) Foreign Application Priority Data

Apr. 25, 2007  (JP) .................................. 2007-115079
Jan. 22, 2008  (JP) .................................. 2008-011127

(51) Int. Cl.
| | | |
|---|---|---|
| H01L 51/54 | (2006.01) | |
| H01L 51/00 | (2006.01) | |
| C09K 11/07 | (2006.01) | |
| H05B 33/14 | (2006.01) | |
| C07D 209/86 | (2006.01) | |
| H01L 51/50 | (2006.01) | |

(52) U.S. Cl.
CPC .......... *C07D 209/86* (2013.01); *H01L 51/0061* (2013.01); *H01L 51/0072* (2013.01); *C09K 2211/1011* (2013.01); *H01L 51/5012* (2013.01); *C09K 11/07* (2013.01); *C09K 2211/1029* (2013.01); *C09K 2211/1014* (2013.01); *C09K 2211/1007* (2013.01); *H01L 51/006* (2013.01); *H05B 33/14* (2013.01); *Y10S 428/917* (2013.01)
USPC ........... 428/690; 428/917; 548/440; 313/504; 313/506; 252/301.16; 257/40; 257/103; 257/E51.051

(58) Field of Classification Search
USPC ................................................ 257/E51.051
See application file for complete search history.

(56) References Cited

U.S. PATENT DOCUMENTS

| | | | |
|---|---|---|---|
| 7,879,464 B2 | 2/2011 | Kawakami et al. | |
| 7,960,566 B2 * | 6/2011 | Ogita et al. | .......... 548/445 |
| 8,017,252 B2 | 9/2011 | Iwaki et al. | |
| 8,198,801 B2 | 6/2012 | Kim et al. | |
| 8,252,434 B2 | 8/2012 | Iwaki et al. | |
| 8,278,649 B2 * | 10/2012 | Ohsawa | .......... 257/40 |
| 8,283,055 B2 * | 10/2012 | Seo et al. | .......... 428/690 |
| 8,541,114 B2 | 9/2013 | Iwaki et al. | |
| 8,686,628 B2 | 4/2014 | Kawakami et al. | |
| 2005/0225235 A1 * | 10/2005 | Kim et al. | .......... 313/504 |
| 2005/0260442 A1 | 11/2005 | Yu et al. | |
| 2007/0075632 A1 | 4/2007 | Kawakami et al. | |
| 2007/0152572 A1 | 7/2007 | Kawakami et al. | |
| 2007/0267969 A1 | 11/2007 | Nakashima et al. | |
| 2013/0320321 A1 | 12/2013 | Iwaki et al. | |

FOREIGN PATENT DOCUMENTS

| | | | | |
|---|---|---|---|---|
| EP | 1696708 A1 * | 12/2004 | ............ | H05B 33/14 |
| EP | 1928828 A | 3/2007 | | |
| JP | 09-310066 | 12/1997 | | |
| JP | 2007-056006 | 3/2007 | | |

(Continued)

OTHER PUBLICATIONS

Jianmin Shi et al., "Anthracene Derivatives for Stable Blue-Emitting Organic Electroluminescence Devices," *Applied Physics Letters*, vol. 80, No. 17, Apr. 29, 2002, pp. 3201-3203.

(Continued)

*Primary Examiner* — Michael H Wilson
(74) *Attorney, Agent, or Firm* — Nixon Peabody LLP; Jeffrey L. Costellia

(57) ABSTRACT

An anthracene derivative represented by a general formula (1) and an organic compound represented by a general formula (8) are provided. Further, by use of the anthracene derivative represented by the general formula (1), a light-emitting element with high emission efficiency can be obtained. Furthermore, by use of the anthracene derivative represented by the general formula (1), a light-emitting element that emits blue light with high color purity can be obtained.

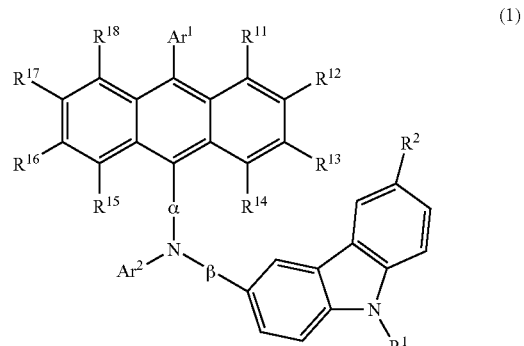

(1)

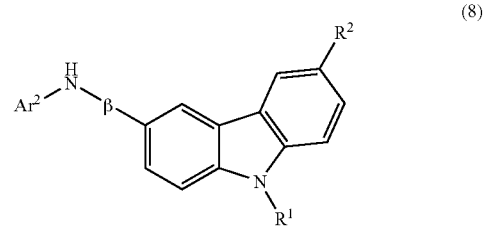

(8)

15 Claims, 34 Drawing Sheets

(56) References Cited

FOREIGN PATENT DOCUMENTS

| | | |
|---|---|---|
| JP | 2007-063501 | 3/2007 |
| JP | 2007-091721 A | 4/2007 |
| KR | 2006-0134849 A | 12/2006 |
| TW | 200600565 B | 1/2006 |
| WO | WO 2005/090512 A1 | 9/2005 |
| WO | WO-2006/104221 | 10/2006 |
| WO | WO 2007/013537 A1 | 2/2007 |
| WO | WO 2007/029530 | 3/2007 |

OTHER PUBLICATIONS

European Search Report; Application No. 08005880.3 (EP10548/11210) Dated Aug. 27, 2008—Full English translation.

Taiwanese Office Action (Application No. 97111177; TW10548/11210) Dated May 17, 2013.

Chinese Office Action (Application No. 201210576949.7) Dated Mar. 25, 2014.

* cited by examiner

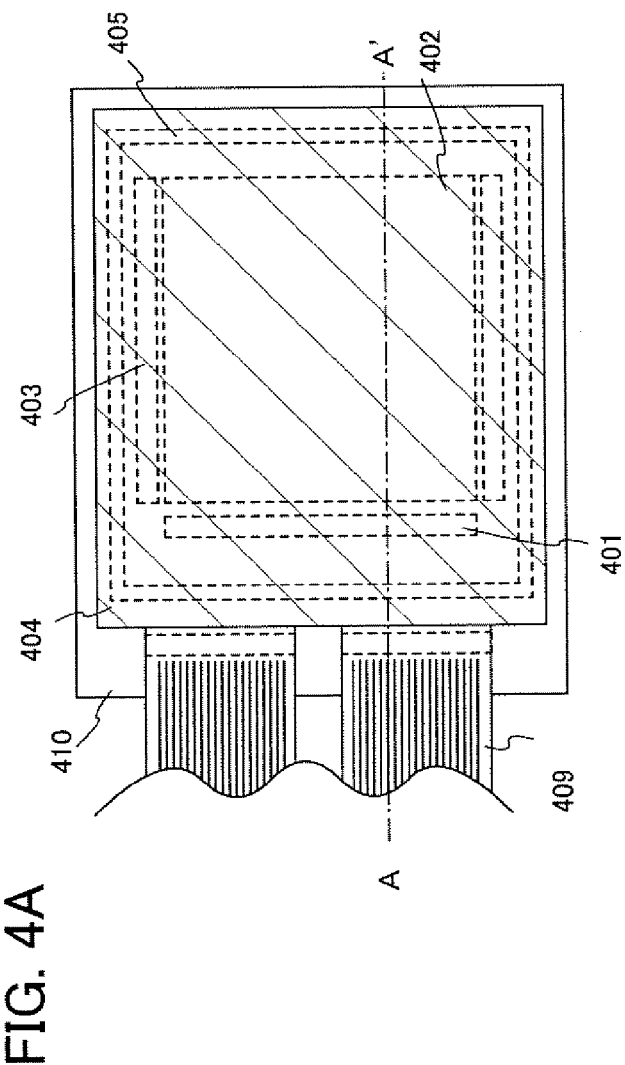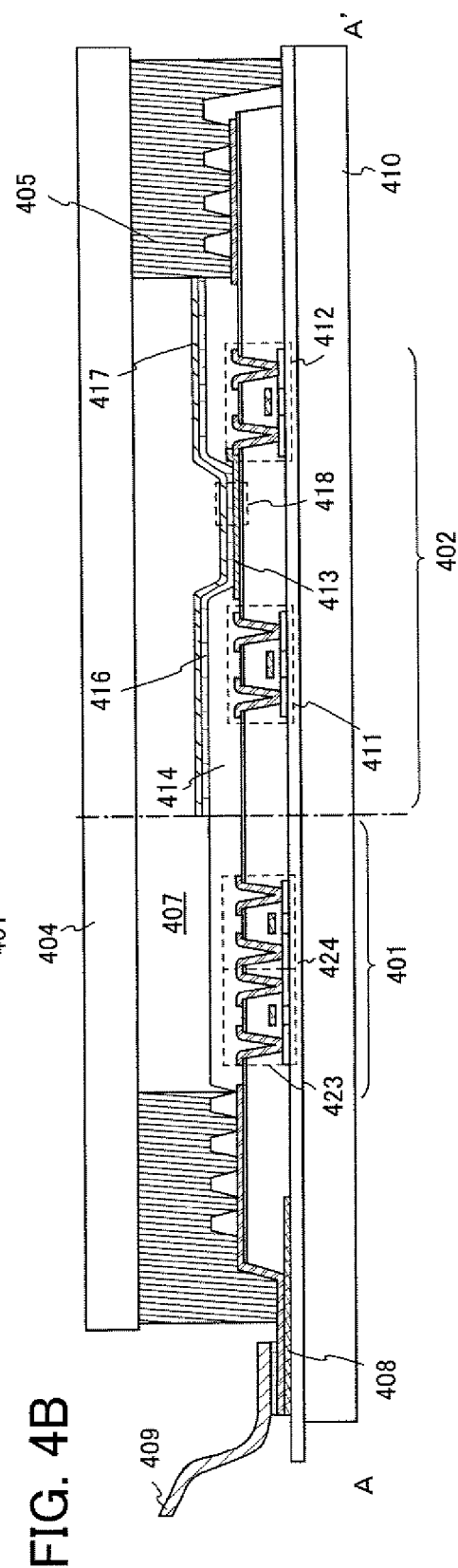
FIG. 4A
FIG. 4B

ORGANIC COMPOUND, ANTHRACENE DERIVATIVE, AND LIGHT-EMITTING ELEMENT, LIGHT-EMITTING DEVICE, AND ELECTRONIC DEVICE IN WHICH THE ANTHRACENE DERIVATIVE IS USED

BACKGROUND OF THE INVENTION

1. Field of the Invention

The present invention relates to organic compounds, anthracene derivatives, and light-emitting elements, light-emitting devices, and electronic devices in which the anthracene derivatives are used.

2. Description of the Related Art

In a light-emitting element, a layer containing an organic compound is interposed between a pair of electrodes. Such a light-emitting element is characterized in that a thin and lightweight element can be fabricated, light is emitted by supply of direct current, response is faster compared to liquid crystals, and the like. Moreover, light-emitting devices in which such light-emitting elements are arranged in matrix form, that is, passive matrix light-emitting devices and active matrix light-emitting devices are superior to conventional liquid crystal displays in terms of wide viewing angle and high visibility. From such reasons, light-emitting elements are desired to be applied to next-generation flat panel displays. In some cases, light-emitting elements are referred to as electroluminescent elements or EL elements.

Electrons are injected from a cathode into a layer containing an organic compound interposed between a pair of electrodes, and at the same time, holes are injected from an anode into the layer containing an organic compound, whereby a light-emitting element is driven. The electrons injected from the cathode and the holes injected from the anode are recombined with each other in the layer containing an organic compound to form molecular excitons. The molecular excitons release energy in returning to a ground state. When the energy is released as light having a wavelength corresponding to that of visible light, light emission can be seen. Excited states of organic compounds include a singlet state and a triplet state, and when either state is the excited state, light can be emitted.

An emission wavelength of a light-emitting element is determined by the energy gap between a ground state and an excited state formed by the recombination that is, a band gap. Therefore, a structure of a molecule that serves for emitting light is selected or modified as appropriate, whereby any emission color of light can be obtained. Further, full color light-emitting device can be manufactured when light-emitting elements that are capable of emitting light of red, blue, and green that are three primary colors of light are used for the manufacture of the light-emitting device.

In order to manufacture a full color light-emitting device with excellent color reproducibility, red, blue, and green light-emitting elements that are highly reliable and excellent in color purity are needed. As a result of recent developments of materials, high reliability and excellent color purity for red and green light-emitting elements have been achieved. However, enough efficiency and color purity for a blue light-emitting element have not been achieved. For example, in Nonpatent Document 1 (J. Shi et al., Applied Physics Letters, Vol. 80, No. 17, pp. 3201-3203, 2002), a blue light-emitting element with relatively high reliability is reported. For the light-emitting element, however, enough emission efficiency and color is not achieved.

SUMMARY OF THE INVENTION

In view of the foregoing problems, objects of the present invention are to provide novel anthracene derivatives and organic compounds.

Another object of the present invention is to provide a light-emitting element with high emission efficiency. Further, another object of the present invention is to provide a light-emitting element that emits blue light with high color purity.

Other objects of the present invention are to provide a light-emitting device and an electronic device in which power consumption is reduced.

As a result of diligent study, the present inventors have found that the problems can be solved with an anthracene derivative represented by a general formula (1) given below. Thus, one aspect of the present invention is an anthracene derivative represented by a general formula (1) given below.

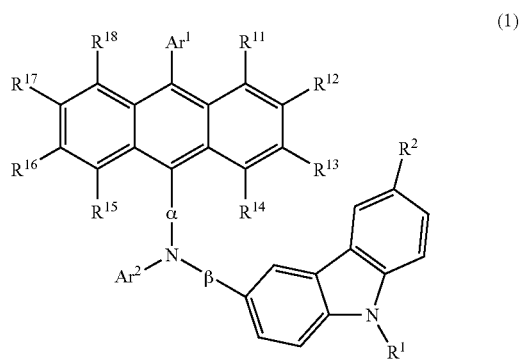

(1)

In the above general formula (1), $Ar^1$ and $Ar^2$ may be the same or different from each other and each represent a substituted or unsubstituted aryl group having 6 to 25 carbon atoms; α and β may be the same or different from each other and each represent a substituted or unsubstituted arylene group having 6 to 25 carbon atoms; $R^1$ represents an alkyl group having 1 to 4 carbon atoms or a substituted or unsubstituted aryl group having 6 to 25 carbon atoms; $R^2$ represents one of hydrogen, an alkyl group having 1 to 4 carbon atoms, a substituted or unsubstituted aryl group having 6 to 25 carbon atoms, a halogen group, and a haloalkyl group; and $R^{11}$ to $R^{18}$ may be the same or different from each other and each represent hydrogen or an alkyl group having 1 to 4 carbon atoms.

One aspect of the present invention is an anthracene derivative represented by a general formula (2) given below.

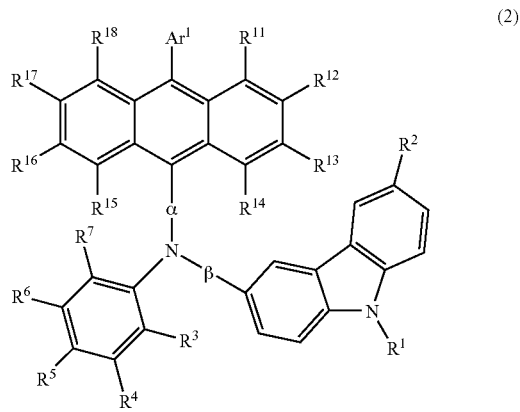

(2)

In the above general formula (2), $Ar^1$ represents a substituted or unsubstituted aryl group having 6 to 25 carbon atoms; α and β may be the same or different from each other and each represent a substituted or unsubstituted arylene group having 6 to 25 carbon atoms; $R^1$ represents an alkyl group having 1 to 4 carbon atoms or a substituted or unsubstituted aryl group having 6 to 25 carbon atoms; $R^2$ represents one of hydrogen, an alkyl group having 1 to 4 carbon atoms, a substituted or unsubstituted aryl group having 6 to 25 carbon atoms, a halogen group, and a haloalkyl group; $R^3$ to $R^7$ may be the same or different from each other and each represent one of hydrogen, an alkyl group having 1 to 4 carbon atoms, a halogen group, and a haloalkyl group; and $R^{11}$ to $R^{18}$ may be the same or different from each other and each represent hydrogen or an alkyl group having 1 to 4 carbon atoms.

One aspect of the present invention is an anthracene derivative represented by a general formula (3) given below.

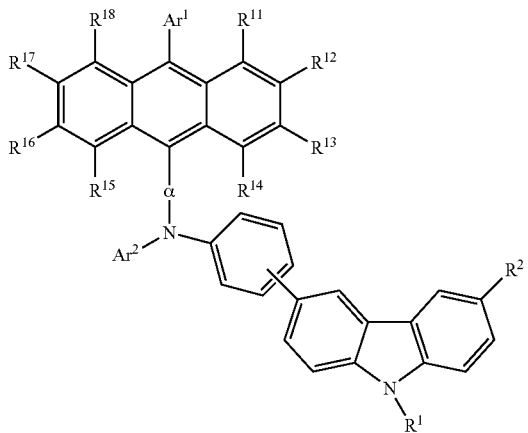

(3)

In the above general formula (3), $Ar^1$ and $Ar^2$ may be the same or different from each other and each represent a substituted or unsubstituted aryl group having 6 to 25 carbon atoms; α represents a substituted or unsubstituted arylene group having 6 to 25 carbon atoms; $R^1$ represents an alkyl group having 1 to 4 carbon atoms or a substituted or unsubstituted aryl group having 6 to 25 carbon atoms; $R^2$ represents one of hydrogen, an alkyl group having 1 to 4 carbon atoms, a substituted or unsubstituted aryl group having 6 to 25 carbon atoms, a halogen group, and a haloalkyl group; and $R^{11}$ to $R^{18}$ may be the same or different from each other and each represent hydrogen or an alkyl group having 1 to 4 carbon atoms.

One aspect of the present invention is an anthracene derivative represented by a general formula (4) given below.

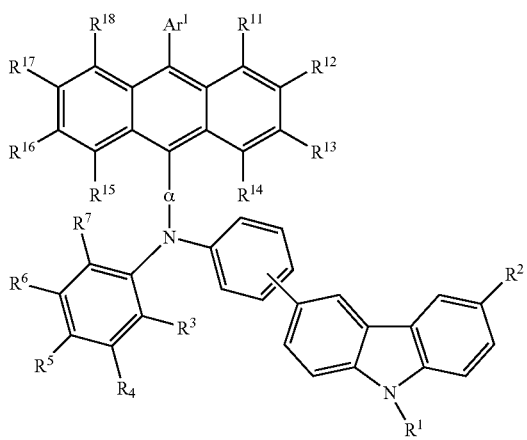

(4)

In the above general formula (4), $Ar^1$ each represents a substituted or unsubstituted aryl group having 6 to 25 carbon atoms; α represents a substituted or unsubstituted arylene group having 6 to 25 carbon atoms; $R^1$ represents an alkyl group having 1 to 4 carbon atoms or a substituted or unsubstituted aryl group having 6 to 25 carbon atoms; $R^2$ represents one of hydrogen, an alkyl group having 1 to 4 carbon atoms, a substituted or unsubstituted aryl group having 6 to 25 carbon atoms, a halogen group, and a haloalkyl group; $R^3$ to $R^7$ may be the same or different from each other and each represent one of hydrogen, an alkyl group having 1 to 4 carbon atoms, a halogen group, and a haloalkyl group; and $R^{11}$ to $R^{18}$ may be the same or different from each other and each represent hydrogen or an alkyl group having 1 to 4 carbon atoms.

One aspect of the present invention is an anthracene derivative represented by a general formula (5) given below.

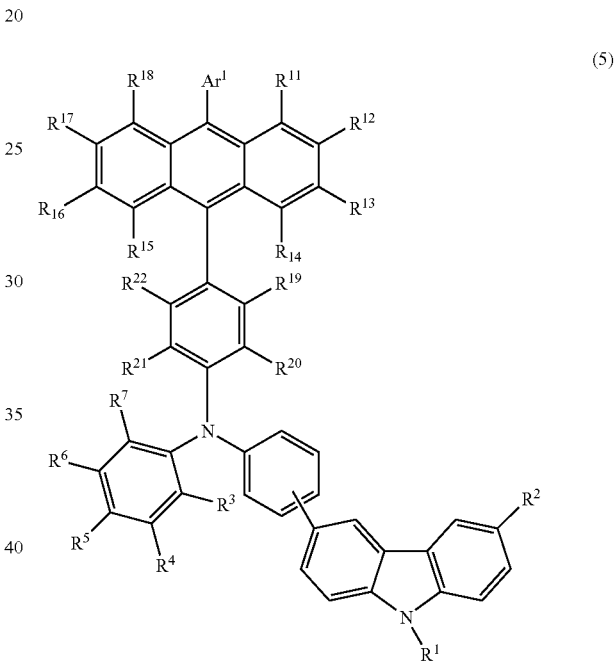

(5)

In the above general formula (5), $Ar^1$ represents a substituted or unsubstituted aryl group having 6 to 25 carbon atoms; $R^1$ represents an alkyl group having 1 to 4 carbon atoms or a substituted or unsubstituted aryl group having 6 to 25 carbon atoms; $R^2$ represents one of hydrogen, an alkyl group having 1 to 4 carbon atoms, a substituted or unsubstituted aryl group having 6 to 25 carbon atoms, a halogen group, and a haloalkyl group; $R^3$ to $R^7$ may be the same or different from each other and each represent one of hydrogen, an alkyl group having 1 to 4 carbon atoms, a halogen group, and a haloalkyl group; $R^{11}$ to $R^{18}$ may be the same or different from each other and each represent hydrogen or an alkyl group having 1 to 4 carbon atoms; and $R^{19}$ to $R^{22}$ may be the same or different from each other and each represent one of hydrogen, an alkyl group having 1 to 4 carbon atoms, and an alkoxy group having 1 to 4 carbon atoms.

One aspect of the present invention is an anthracene derivative represented by a general formula (6) given below.

(6)

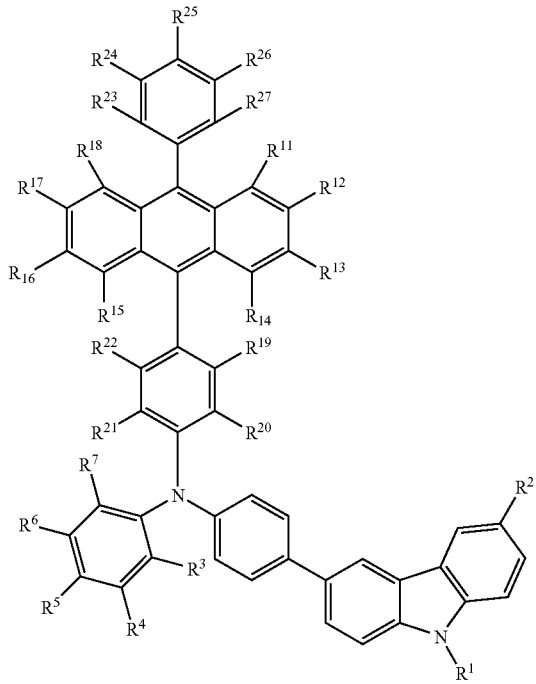

In the above general formula (6), $R^1$ represents an alkyl group having 1 to 4 carbon atoms or a substituted or unsubstituted aryl group having 6 to 25 carbon atoms; $R^2$ represents one of hydrogen, an alkyl group having 1 to 4 carbon atoms, a substituted or unsubstituted aryl group having 6 to 25 carbon atoms, a halogen group, and a haloalkyl group; $R^3$ to $R^7$ may be the same or different from each other and each represent one of hydrogen, an alkyl group having 1 to 4 carbon atoms, a halogen group, and a haloalkyl group; $R^{11}$ to $R^{18}$ may be the same or different from each other and each represent hydrogen or an alkyl group having 1 to 4 carbon atoms; and $R^{19}$ to $R^{27}$ may be the same or different from each other and each represent one of hydrogen, an alkyl group having 1 to 4 carbon atoms, and an alkoxy group having 1 to 4 carbon atoms.

One aspect of the present invention is an anthracene derivative represented by a general formula (7) given below.

(7)

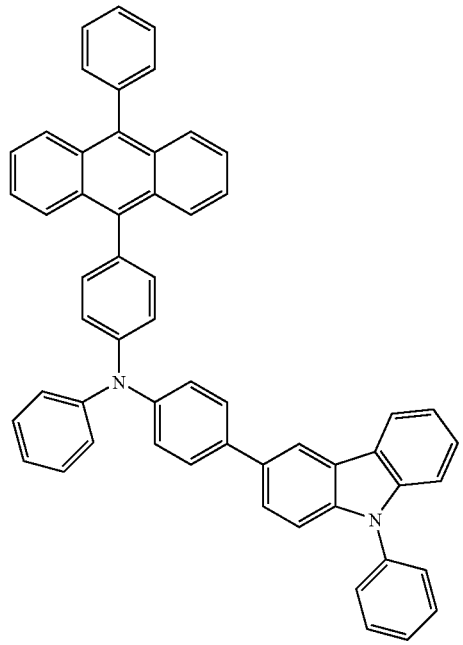

One aspect of the present invention is a light-emitting element that contains any of the above anthracene derivatives, that is, a light-emitting element that contains any of the above anthracene derivatives between a pair of electrodes.

Further, since the above anthracene derivatives have high emission efficiency, it is preferred that each of them be used for a light-emitting layer. Thus, one aspect of the present invention is a light-emitting element that includes a light-emitting layer between a pair of electrodes, where the light-emitting layer contains any of the above anthracene derivatives.

The light-emitting element of the present invention thus obtained can be made to have a long life, and thus, a light-emitting device (e.g., an image display device) in which such a light-emitting element is used can be made to have a long life. Thus, the present invention also covers the light-emitting device and an electronic device in which the light-emitting element of the present invention is used.

The light-emitting device of the present invention is characterized in that it includes a light-emitting element that contains any of the above-described anthracene derivatives and a control circuit configured to control light emission from the light-emitting element. The category of the light-emitting device in this specification includes an image display device in which a light-emitting element is used. Further, the category of the light-emitting device also includes a module in which a connecter such as an anisotropic film, a tape automated bonding (TAB) tape, or a tape carrier package (TCP) is attached to a light-emitting element; a module in which a printed wiring board is provided at an end of a TAB tape or a TCP; and a module in which an integrated circuit (IC) is directly mounted on a light-emitting element by a chip on glass (COG) method. In addition, the category includes a light-emitting device used for a lighting device or the like.

Further, an electronic device in which the light-emitting element of the present invention is used for its display portion is also included in the category of the present invention. Accordingly, one aspect of the present invention is an electronic device having a display portion, where the display portion includes the above-described light-emitting element and a control circuit configured to control light emission from the light-emitting element.

Furthermore, the present invention also covers organic compounds used for the synthesis of the anthracene derivatives of the present invention because the organic compounds used for the synthesis of the anthracene derivatives of the present invention are novel materials. Accordingly, one aspect of the present invention is an organic compound represented by a general formula (8) given below.

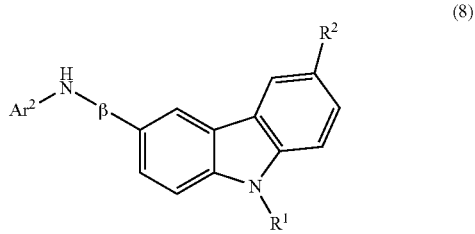

(8)

In the above general formula (8), $Ar^2$ represents a substituted or unsubstituted aryl group having 6 to 25 carbon atoms; β represents a substituted or unsubstituted arylene group having 6 to 25 carbon atoms; $R^1$ represents an alkyl group having 1 to 4 carbon atoms or a substituted or unsubstituted aryl group having 6 to 25 carbon atoms; and $R^2$ represents one of hydrogen, an alkyl group having 1 to 4 carbon atoms, a substituted or unsubstituted aryl group having 6 to 25 carbon atoms, a halogen group, and a haloalkyl group.

One aspect of the present invention is an organic compound represented by a general formula (9) given below.

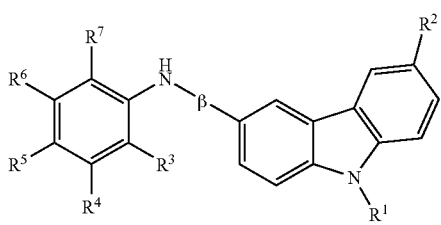

(9)

In the above general formula (9), β represents a substituted or unsubstituted arylene group having 6 to 25 carbon atoms; $R^1$ represents an alkyl group having 1 to 4 carbon atoms or a substituted or unsubstituted aryl group having 6 to 25 carbon atoms; $R^2$ represents one of hydrogen, an alkyl group having 1 to 4 carbon atoms, a substituted or unsubstituted aryl group having 6 to 25 carbon atoms, a halogen group, and a haloalkyl group; and $R^3$ to $R^7$ may be the same or different from each other and each represent one of hydrogen, an alkyl group having 1 to 4 carbon atoms, a halogen group, and a haloalkyl group.

One aspect of the present invention is an organic compound represented by a general formula (10) given below.

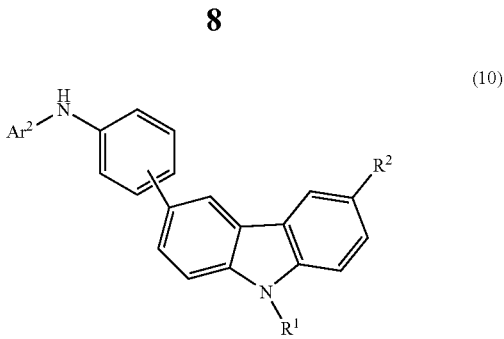

(10)

In the above general formula (10), $Ar^2$ represents a substituted or unsubstituted aryl group having 6 to 25 carbon atoms; $R^1$ represents an alkyl group having 1 to 4 carbon atoms or a substituted or unsubstituted aryl group having 6 to 25 carbon atoms; and $R^2$ represents one of hydrogen, an alkyl group having 1 to 4 carbon atoms, a substituted or unsubstituted aryl group having 6 to 25 carbon atoms, a halogen group, and a haloalkyl group.

One aspect of the present invention is an organic compound represented by a general formula (11) given below.

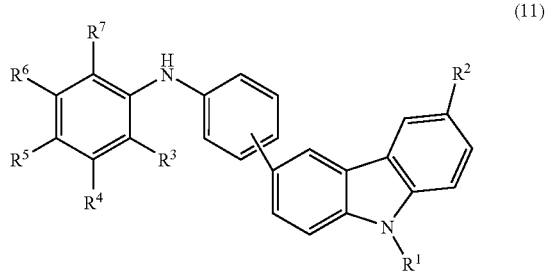

(11)

In the above general formula (11), $R^1$ represents an alkyl group having 1 to 4 carbon atoms or a substituted or unsubstituted aryl group having 6 to 25 carbon atoms; $R^2$ represents one of hydrogen, an alkyl group having 1 to 4 carbon atoms, a substituted or unsubstituted aryl group having 6 to 25 carbon atoms, a halogen group, and a haloalkyl group; and $R^3$ to $R^7$ may be the same or different from each other and each represent one of hydrogen, an alkyl group having 1 to 4 carbon atoms, a halogen group, and a haloalkyl group One aspect of the present invention is an organic compound represented by a general formula (12) given below.

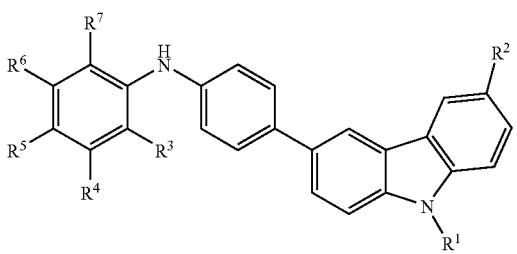

(12)

In the above general formula (12), $R^1$ represents an alkyl group having 1 to 4 carbon atoms or a substituted or unsubstituted aryl group having 6 to 25 carbon atoms; $R^2$ represents one of hydrogen, an alkyl group having 1 to 4 carbon atoms, a substituted or unsubstituted aryl group having 6 to 25 carbon atoms, a halogen group, and a haloalkyl group; and $R^3$ to $R^7$ may be the same or different from each other and each represent one of hydrogen, an alkyl group having 1 to 4 carbon atoms, a halogen group, and a haloalkyl group.

One aspect of the present invention is an organic compound represented by a general formula (13) given below.

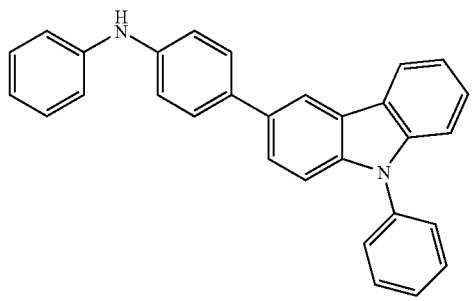

(13)

The anthracene derivatives of the present invention have high emission efficiency. Furthermore, the anthracene derivatives of the present invention can emit blue light with high color purity.

Furthermore, by use of any of the anthracene derivatives of the present invention, a light-emitting element with high emission efficiency can be obtained. Further, a light-emitting element that emits blue light with high color purity can also be obtained.

Furthermore, by use of any of the anthracene derivatives of the present invention, a light-emitting device and an electronic device in which power consumption is reduced can be obtained.

BRIEF DESCRIPTION OF THE DRAWINGS

FIGS. 4A and 4B illustrate a light-emitting device of the present invention.

DETAILED DESCRIPTION OF THE INVENTION

Figure 1:
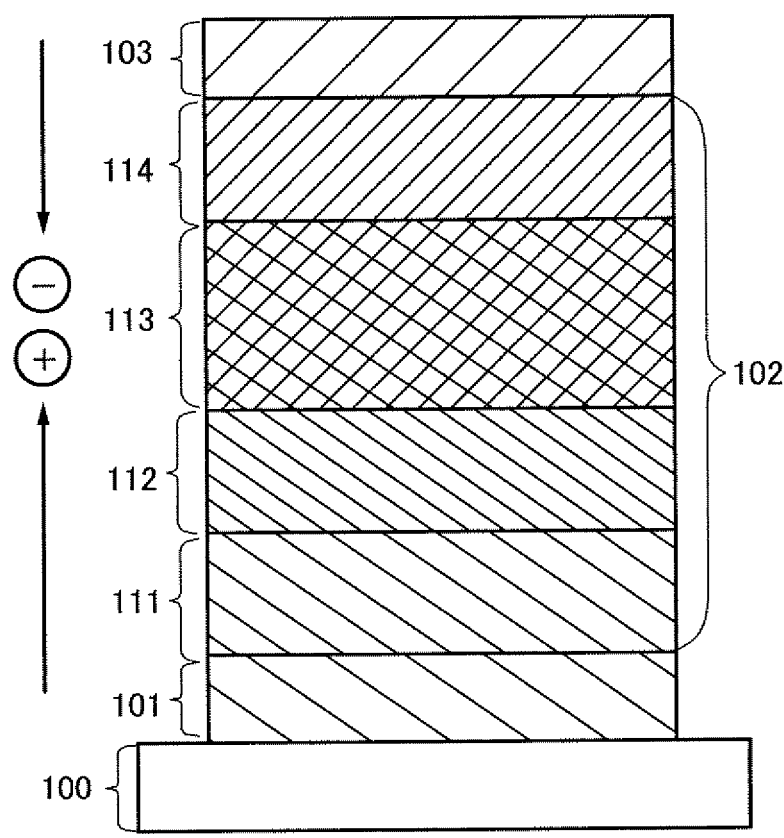
FIG. 1 illustrates a light-emitting element of the present invention.

Hereinafter, embodiment modes and examples of the present invention are described using the accompanying drawings. It is easily understood by those skilled in the art that a variety of changes may be made in forms and details without departing from the spirit and the scope of the present invention. Therefore, the present invention should not be limited to the description of the embodiment modes and examples below.

[Embodiment Mode 1]

In this embodiment mode, anthracene derivatives of the present invention are described.

An anthracene derivative of the present invention is represented by the general formula (1).

(1)

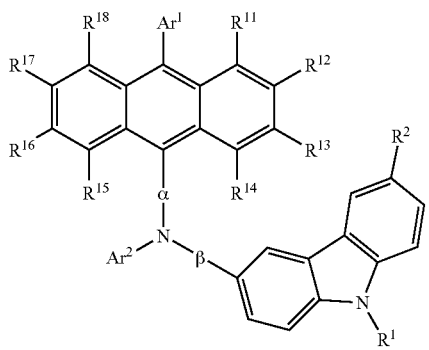

In the above general formula (1), $Ar^1$ and $Ar^2$ may be the same or different from each other and each represent a substituted or unsubstituted aryl group having 6 to 25 carbon atoms; α and β may be the same or different from each other and each represent a substituted or unsubstituted arylene group having 6 to 25 carbon atoms; $R^1$ represents an alkyl group having 1 to 4 carbon atoms or a substituted or unsubstituted aryl group having 6 to 25 carbon atoms; $R^2$ represents one of hydrogen, an alkyl group having 1 to 4 carbon atoms, a substituted or unsubstituted aryl group having 6 to 25 carbon atoms, a halogen group, and a haloalkyl group; and $R^{11}$ to $R^{18}$ may be the same or different from each other and each represent hydrogen or an alkyl group having 1 to 4 carbon atoms.

Structures shown in (Ar-1) to (Ar-19) are given as examples of substituents represented by $Ar^1$ and $Ar^2$ in the above general formula (1). Further, $Ar^1$ may have an alkyl group having 1 to 4 carbon atoms or an alkoxy group having 1 to 4 carbon atoms. In fabrication of a light-emitting element by a wet process, using any of the anthracene derivatives of the present invention, it is preferred that $Ar^1$ have an alkyl group having 1 to 4 carbon atoms or an alkoxy group having 1 to 4 carbon atoms because such a structure increases the solubility of the anthracene derivative of the present invention.

(Ar-1)

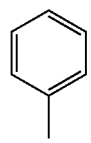

(Ar-2)

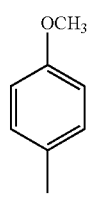

(Ar-3)

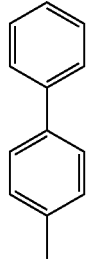

(Ar-4)

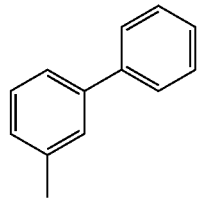

(Ar-5)

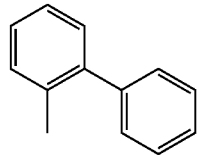

(Ar-6)

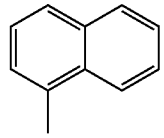

(Ar-7)

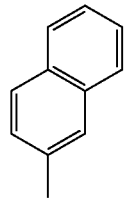

(Ar-8)

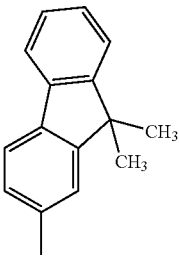

(Ar-9)

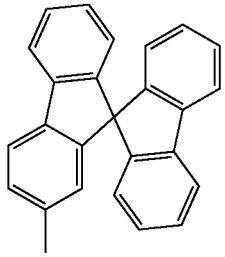

(Ar-10) 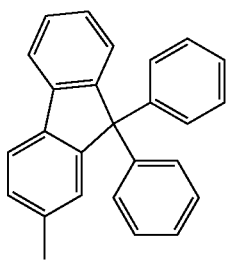

(Ar-11) 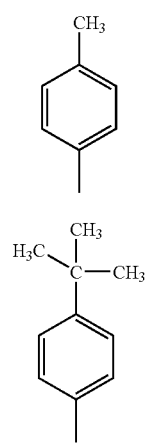

(Ar-12) 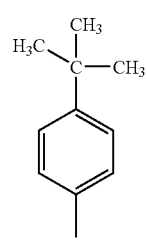

(Ar-13) 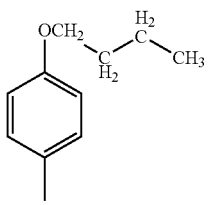

(Ar-14) 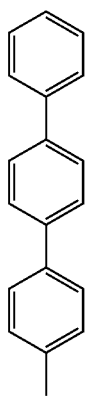

(Ar-15) 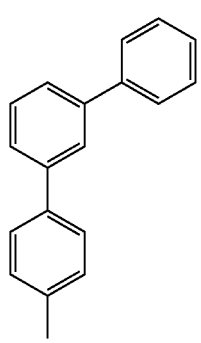

(Ar-16) 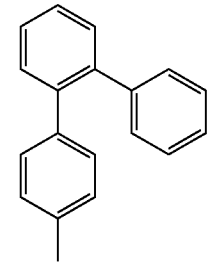

(Ar-17) 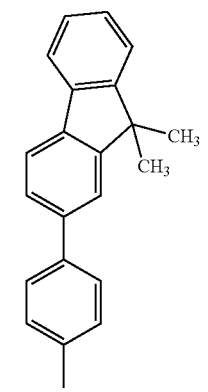

(Ar-18) 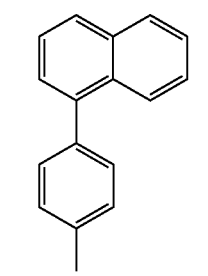

(Ar-19) 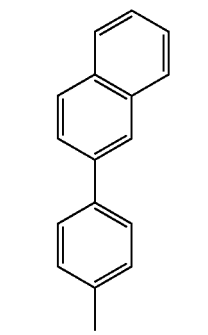

Structures shown in (α-1) to (α-12) are given as examples of a structure represented by α in the above general formula (1). Further, α may have an alkyl group having 1 to 4 carbon atoms or an alkoxy group having 1 to 4 carbon atoms. When α has an alkyl group having 1 to 4 carbon atoms or an alkoxy group having 1 to 4 carbon atoms, the solubility of the anthracene derivative of the present invention is increased; therefore, a light-emitting element can be fabricated using any of the anthracene derivatives of the present invention by a wet process.

(α-1)
(α-2)
(α-3)
(α-4)
(α-5)
(α-6)
(α-7)
(α-8)
(α-9)
(α-10)
(α-11)
(α-12)
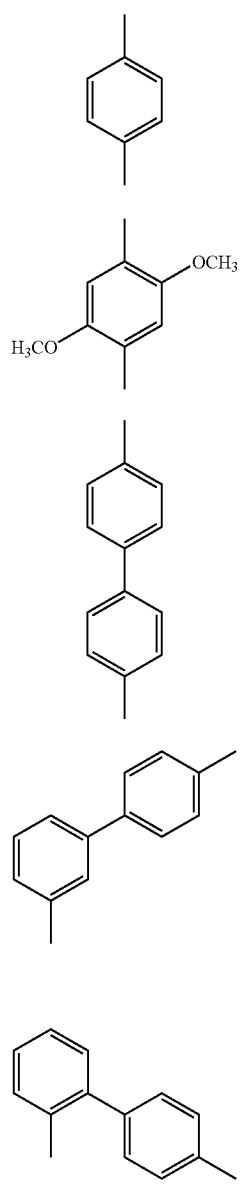
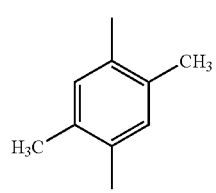
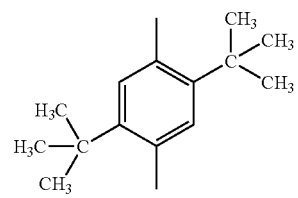
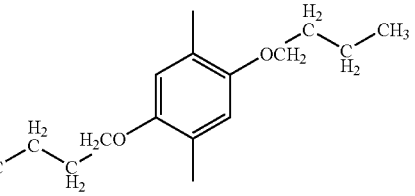
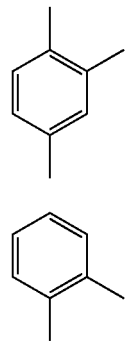
Structures shown in (β-1) to (β-10) are given as examples of a structure represented by β in the above general formula (1).
(β-1)
(β-2)
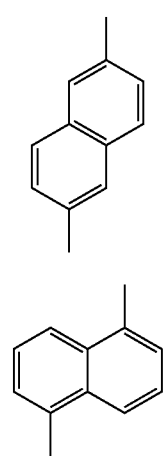

(β-3)
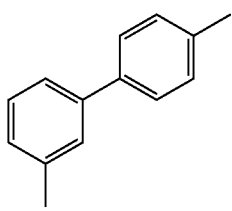
(β-4)
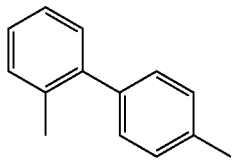
(β-5)
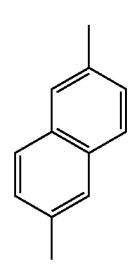
(β-6)
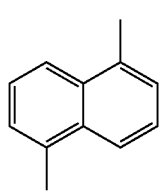
(β-7)
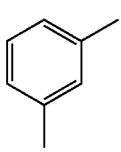
(β-8)
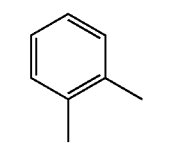
(β-9)
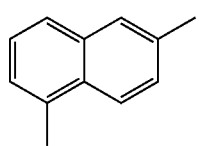
(β-10)
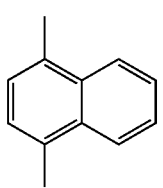
Structures shown in (R1-1) to (R1-21) are given as examples of a substituent represented by $R^1$ in the above general formula (1).
(R1-1)
(R1-2)
(R1-3)
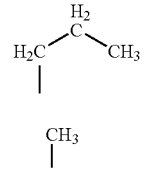
(R1-4)
(R1-5)
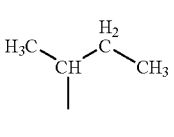
(R1-6)
(R1-7)
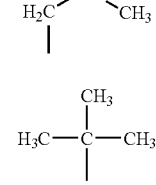
(R1-8)
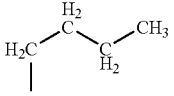
(R1-9)
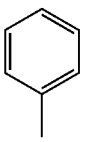
(R1-10)
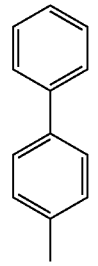
(R1-11)
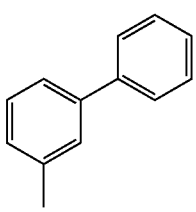

(R1-12) 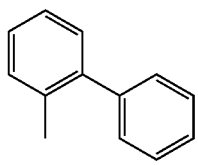
(R1-13) 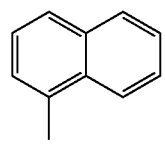
(R1-14) 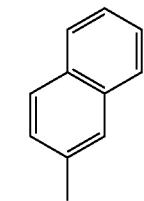
(R1-15) 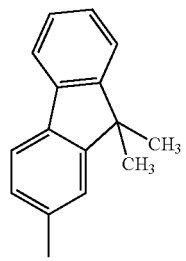
(R1-16) 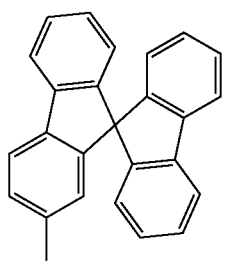
(R1-17) 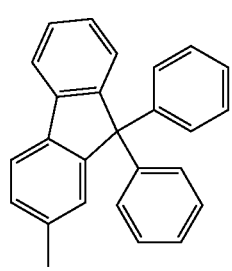
(R1-18) 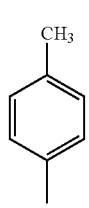
(R1-19) 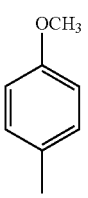
(R1-20) 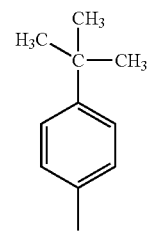
(R1-21) 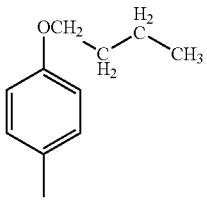
Structures shown in (R2-1) to (R2-24) are given as examples of a substituent represented by $R^2$ in the above general formula (1).
(R2-1)
H
(R2-2)
CH₃
(R2-3)
CH₃
|
CH₂
|
(R2-4)
    H₂
    C
H₂C   CH₃
    |
(R2-5)
   CH₃
   |
HC—CH₃
   |
(R2-6)
F
|
(R2-7)
       H₂
H₃C    C
   CH    CH₃
   |
(R2-8)
    CH₃
    |
    CH
H₂C    CH₃
|

-continued (R2-9)
(R2-10)
(R2-11)
(R2-12)
(R2-13)
(R2-14)
(R2-15)
(R2-16)
(R2-17)

(R2-18)
(R2-19)
(R2-20)
(R2-21)
(R2-22)
(R2-23)
(R2-24)

Specific examples of such an anthracene derivative of the present invention include, but are not limited to, anthracene derivatives represented by structural formulae (100) to (164) given below.

(104)
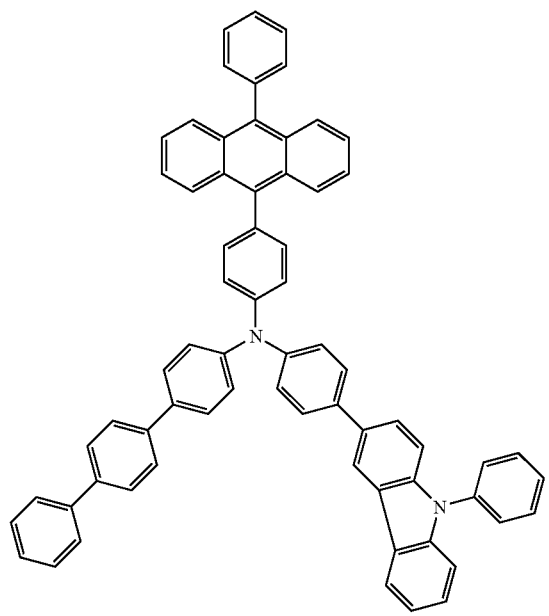
(105)
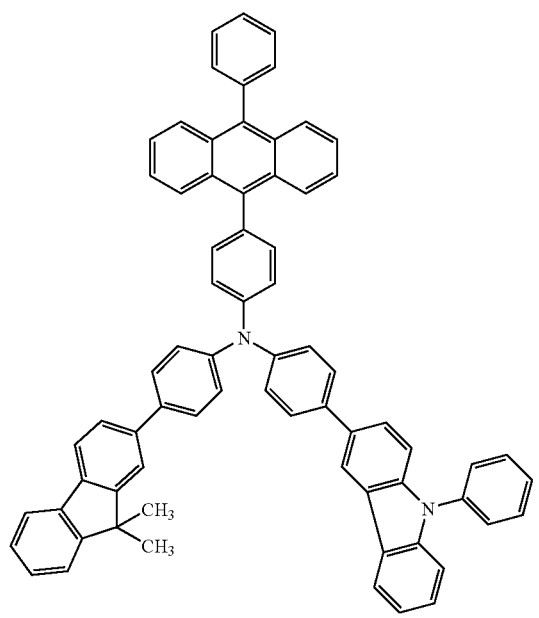
(106)
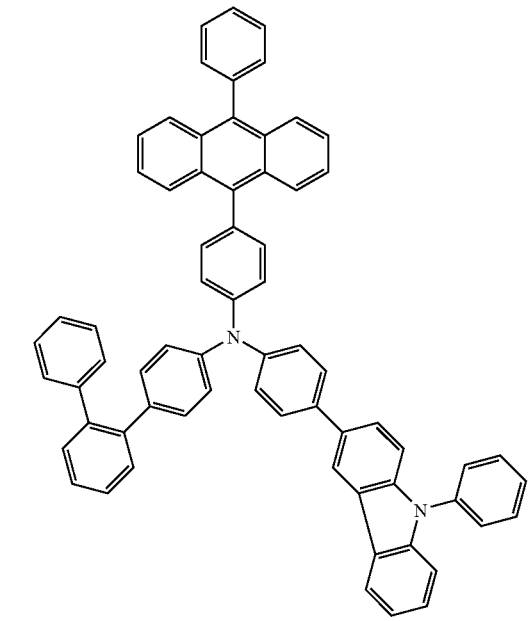
(107)
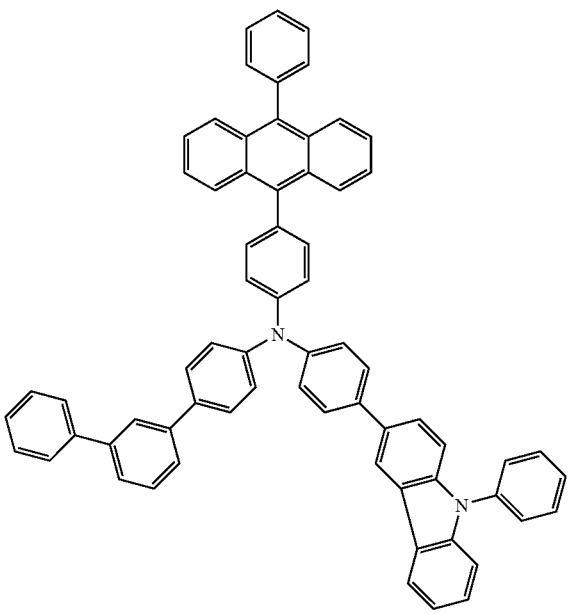

(108)
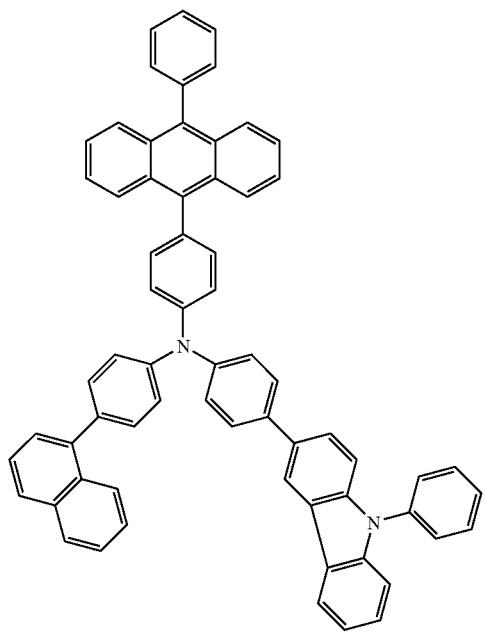
(110)
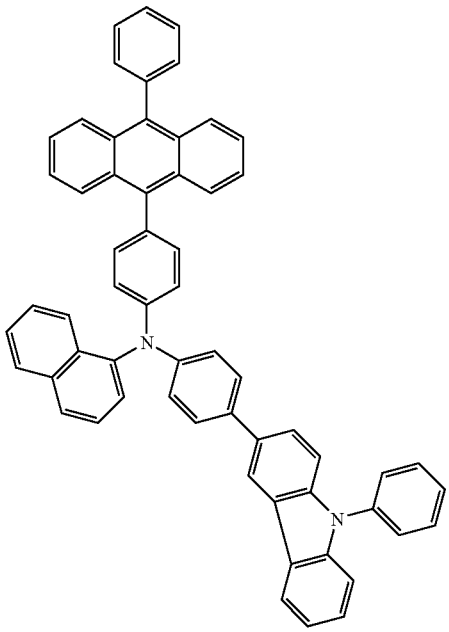
(109)
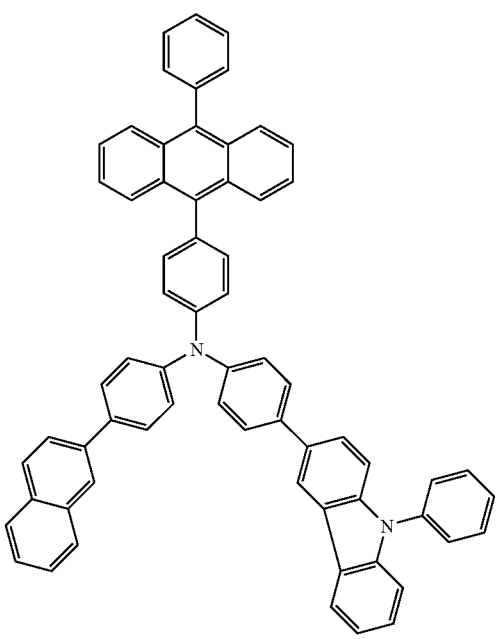
(111)
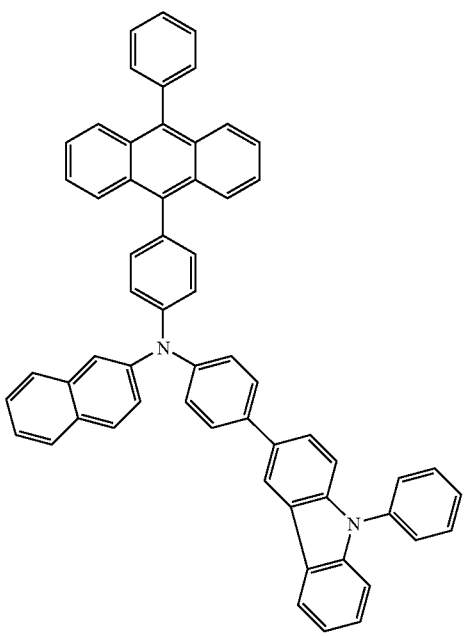

(112)
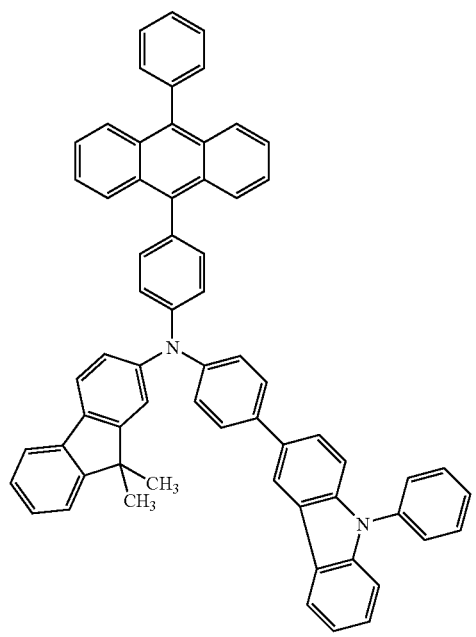
(113)
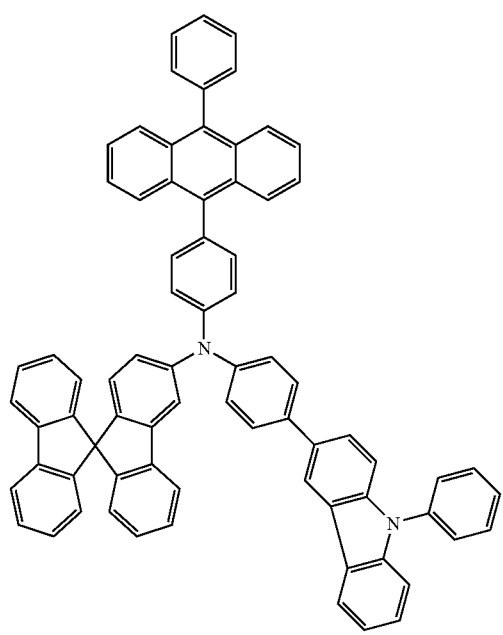
(114)
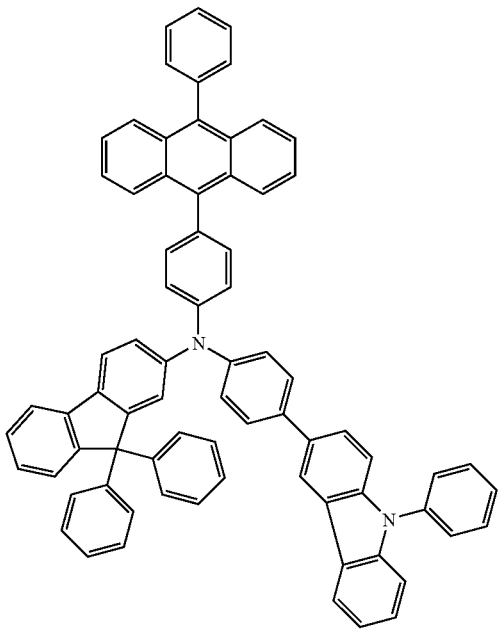
(115)
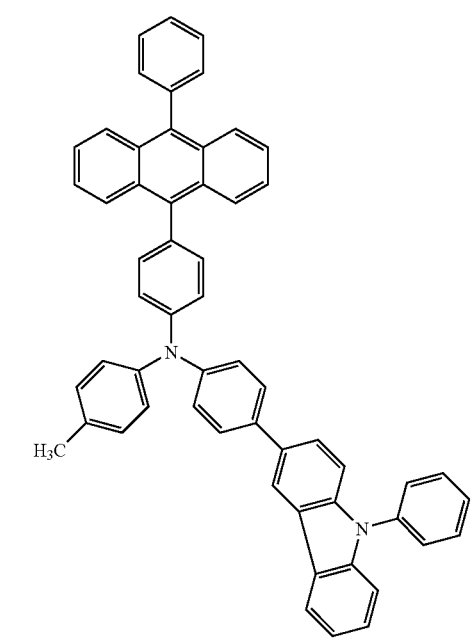

(116)
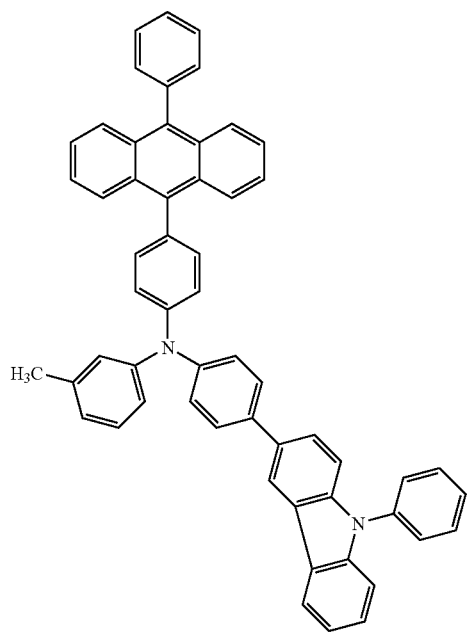
(118)
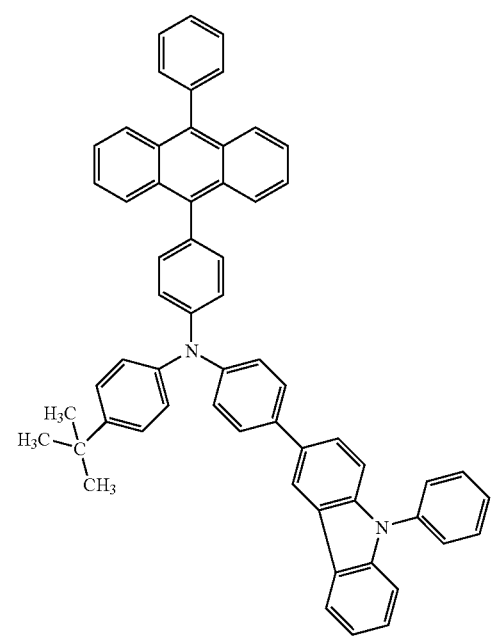
(117)
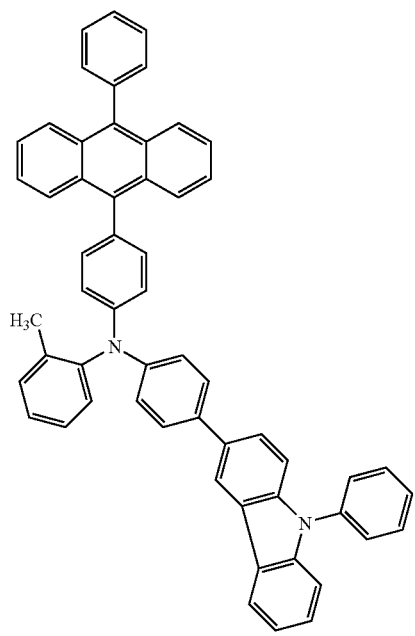
(119)
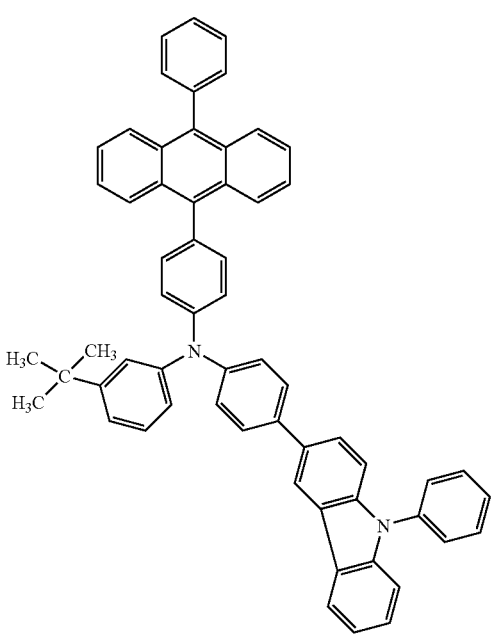

(120)
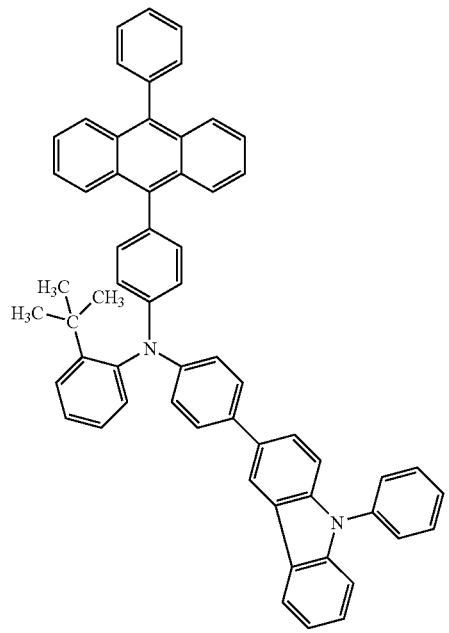
(122)
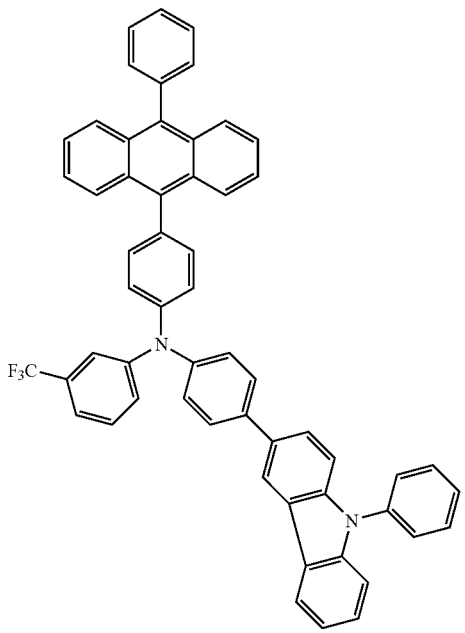
(121)
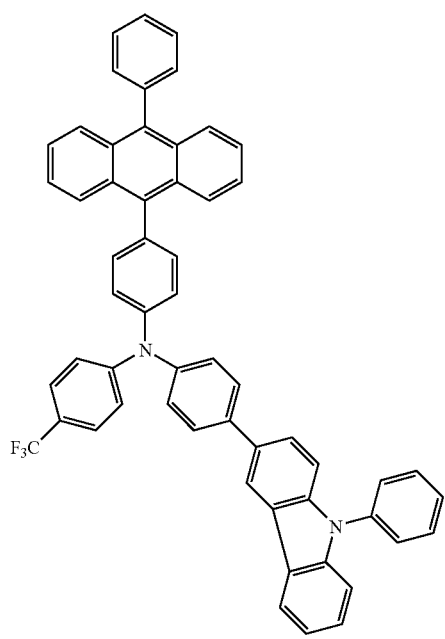
(123)
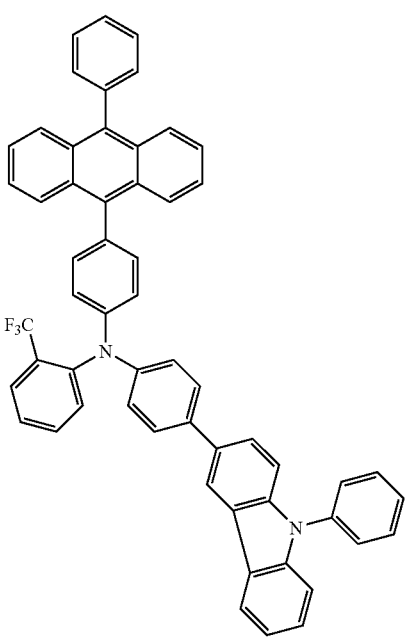

(124)
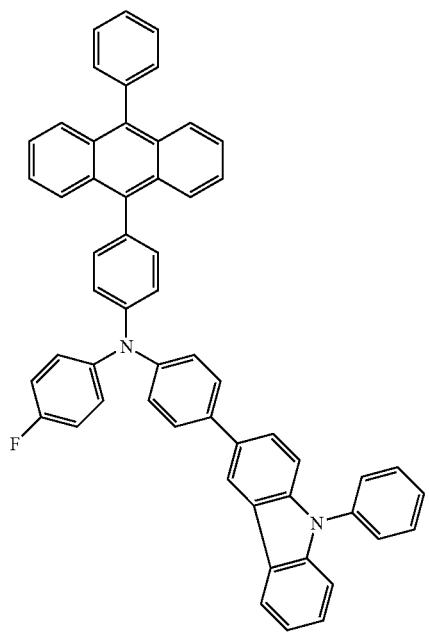
(125)
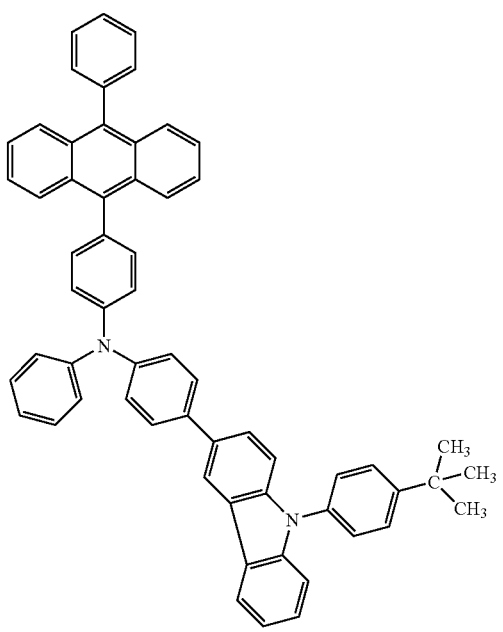
(126)
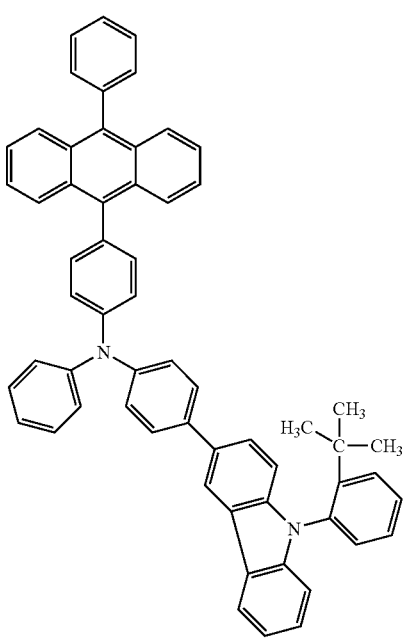
(127)
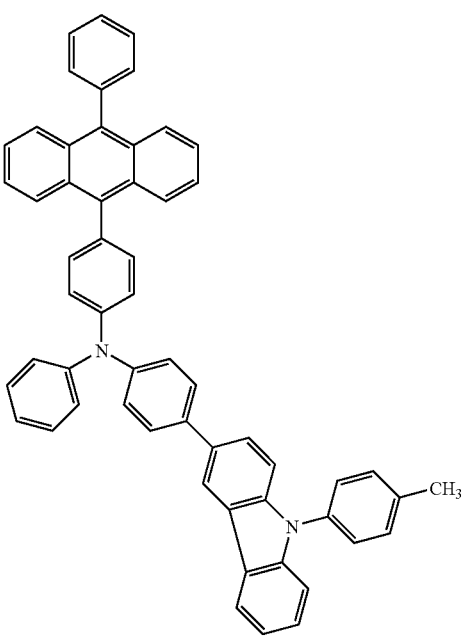

(128)
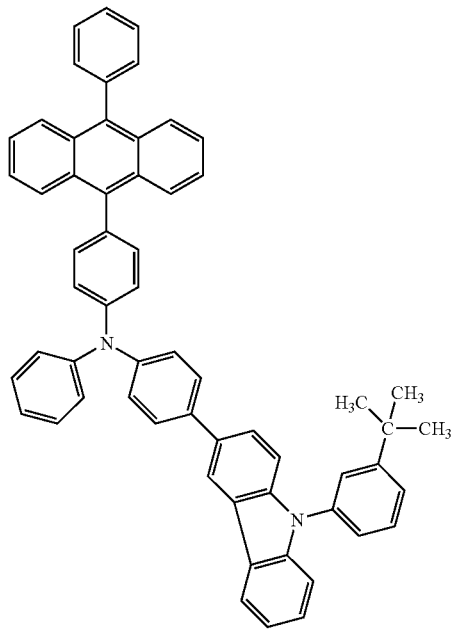
(129)
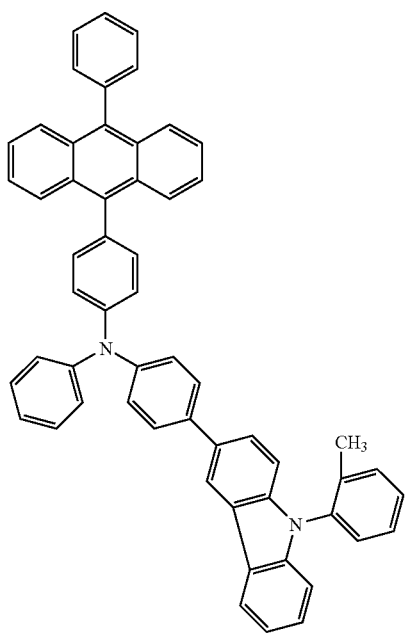
(130)
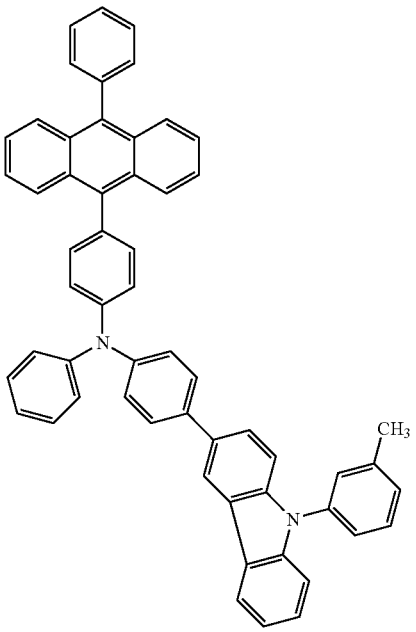
(131)
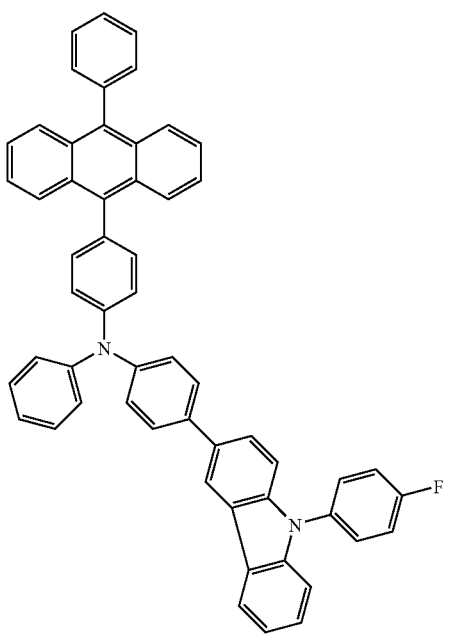

(132)
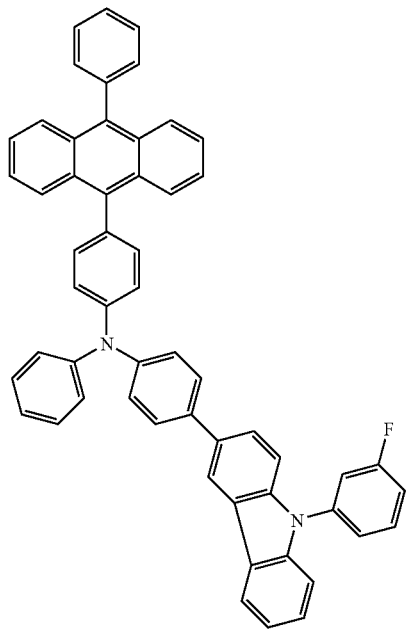
(133)
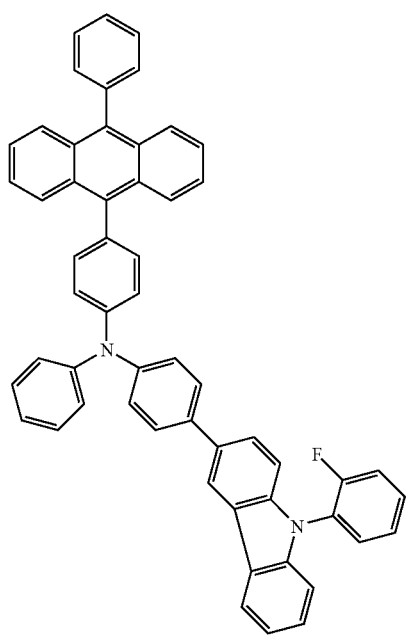
(134)
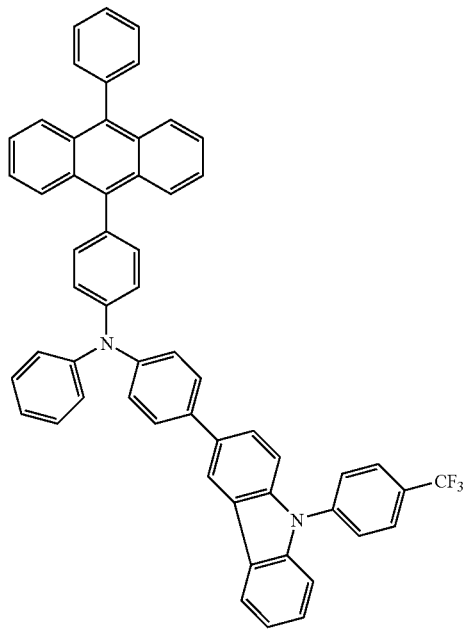
(135)
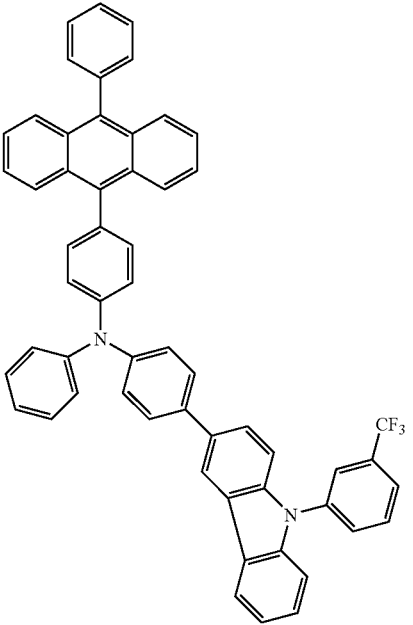

(136)
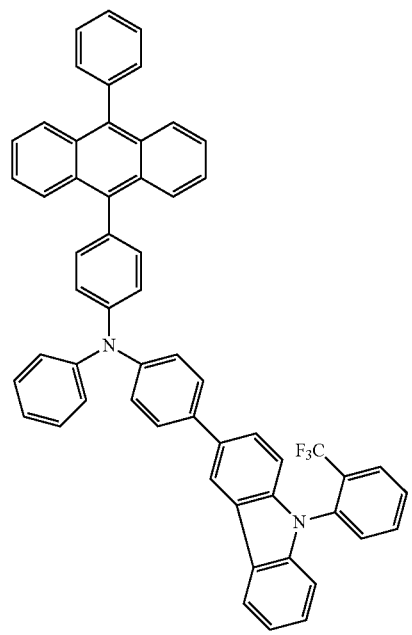
(137)
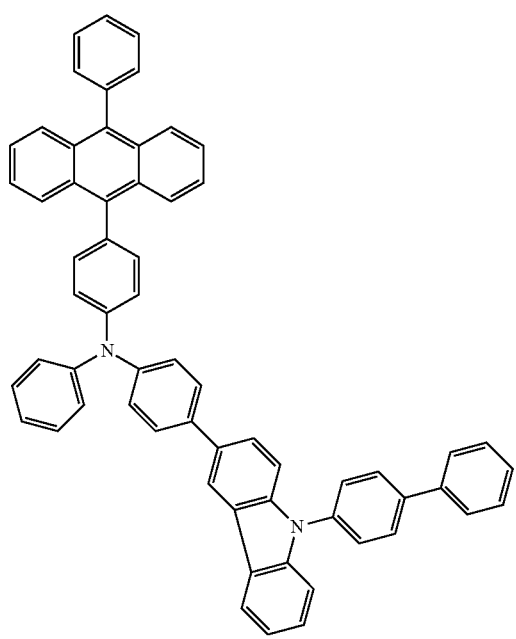
(138)
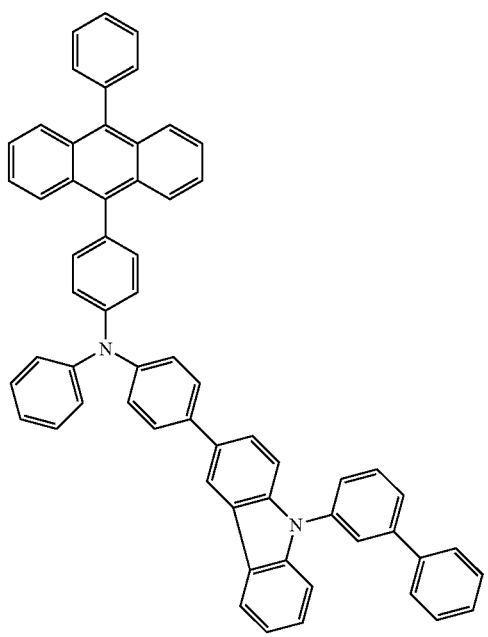
(139)
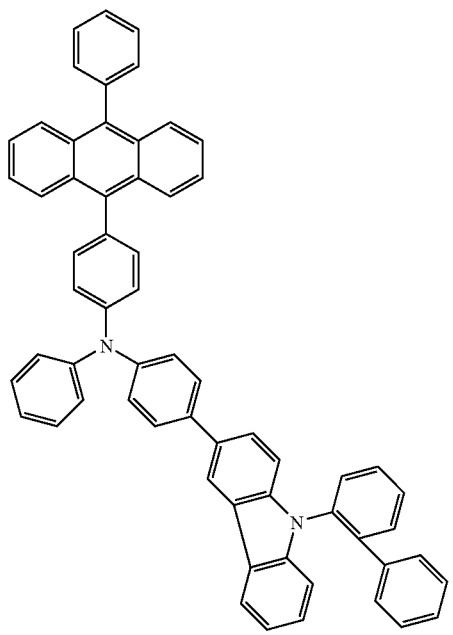

(140)

(141)

(142)

(143)

(145)
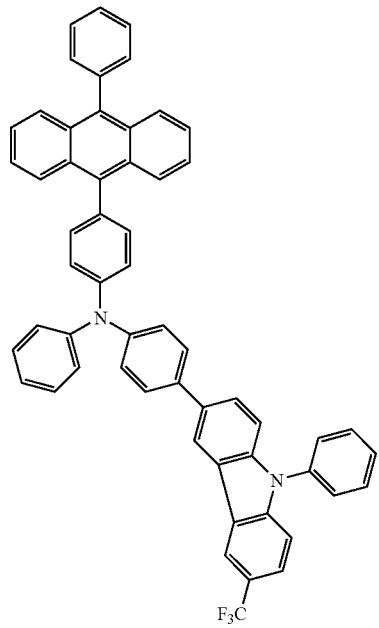
(147)
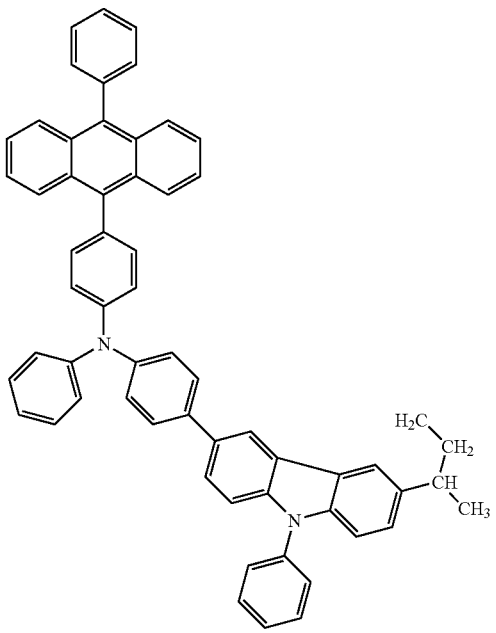
(146)
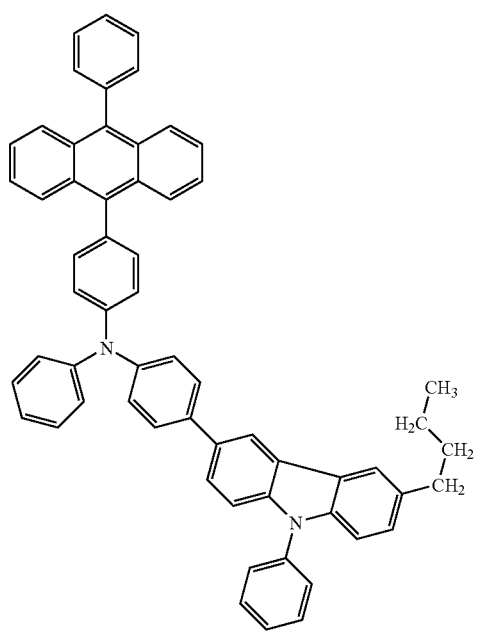
(148)
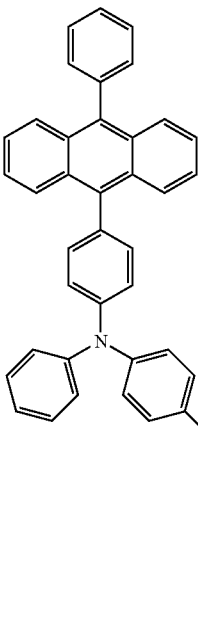

(149)
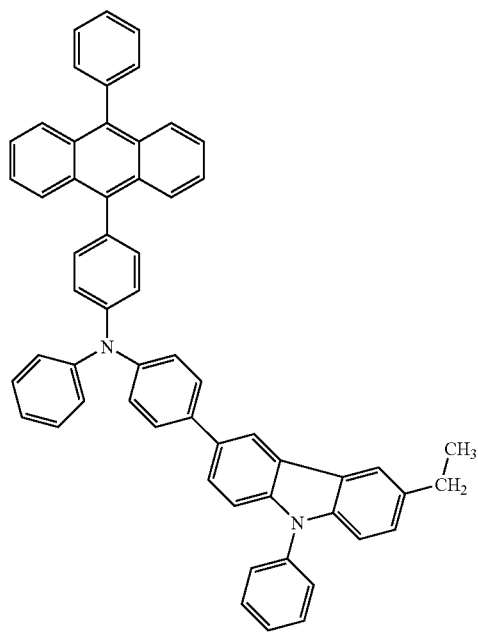
(150)
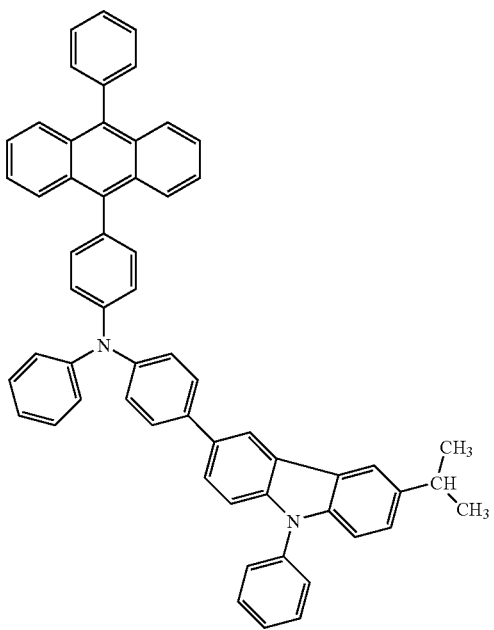
(151)
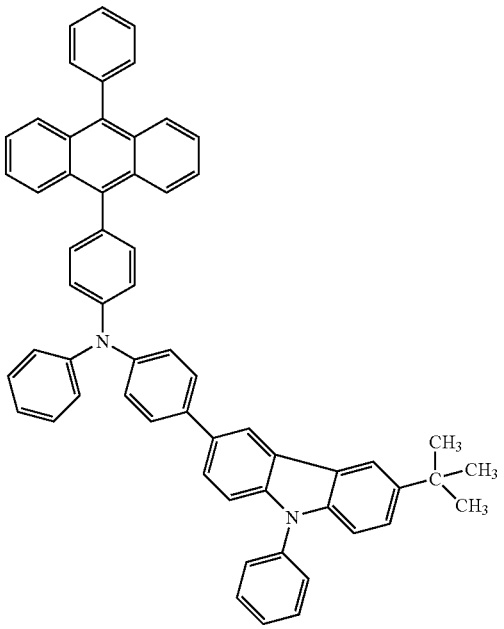
(152)
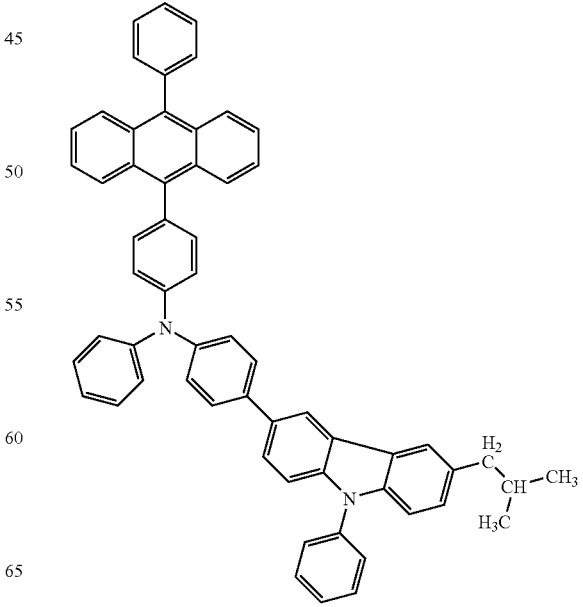

(153)
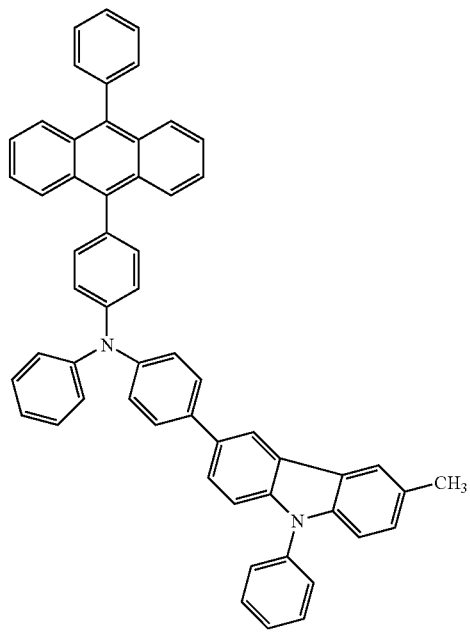
(154)
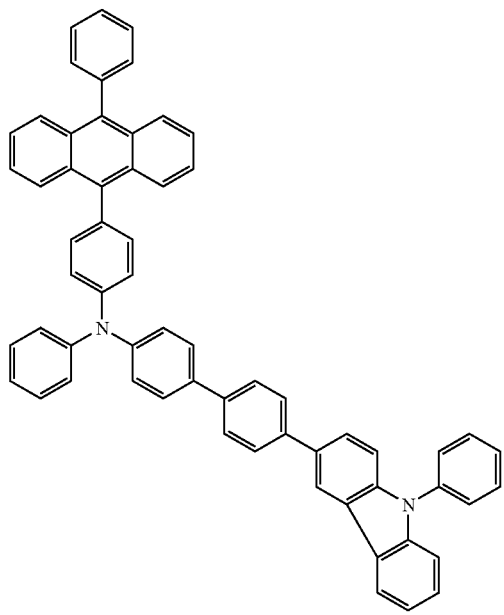
(155)
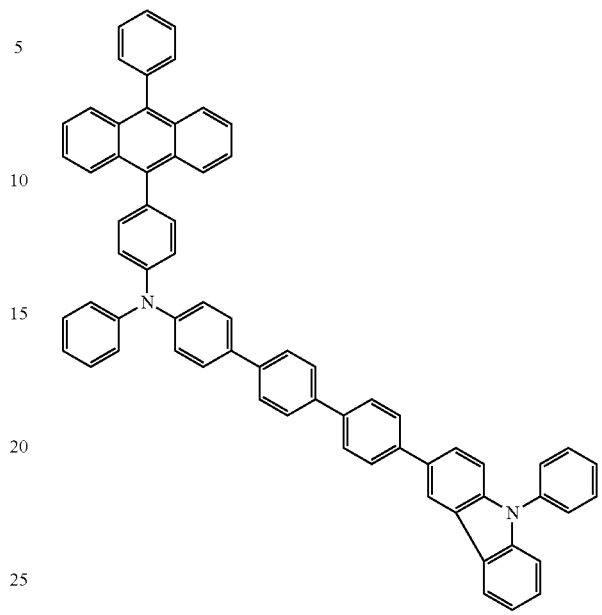
(156)
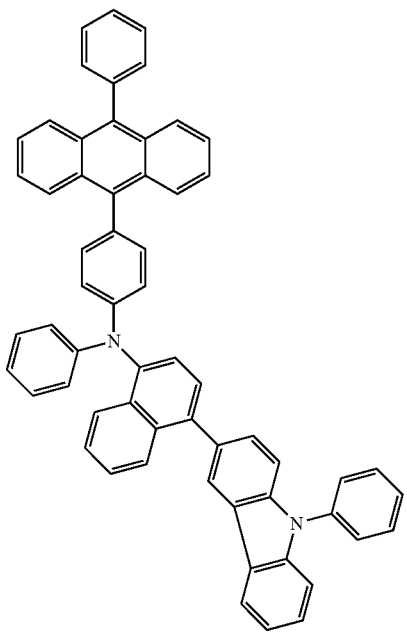

(157)
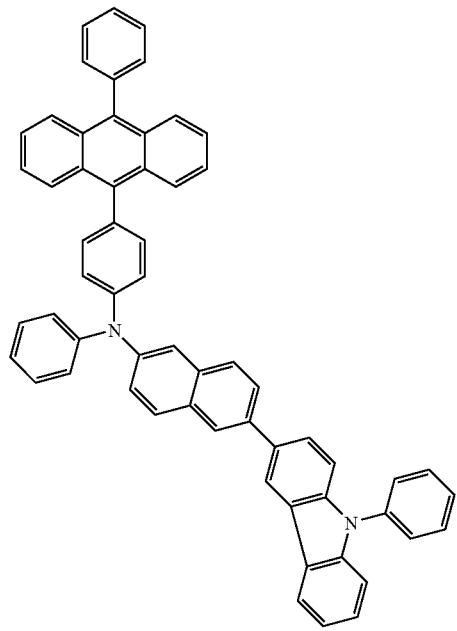
(158)
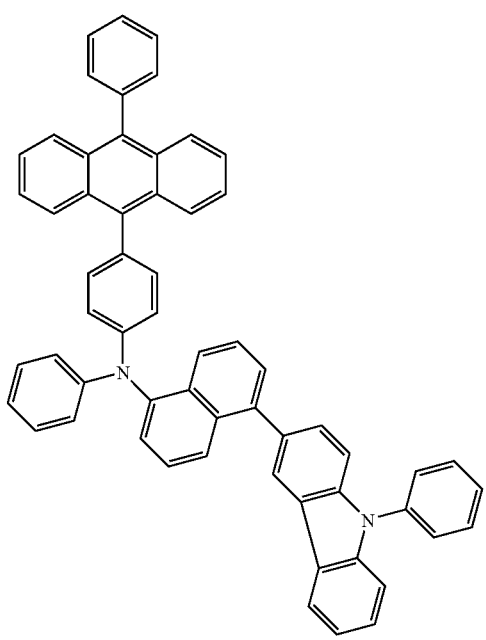
(159)
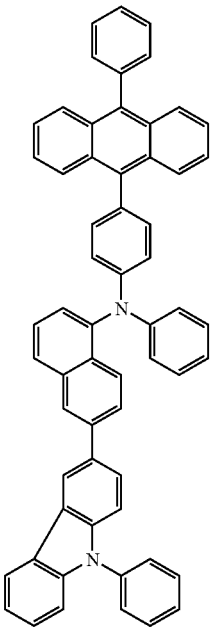
(160)
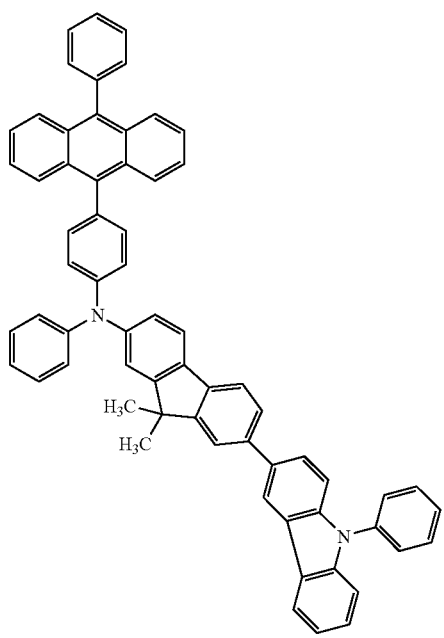

(161)

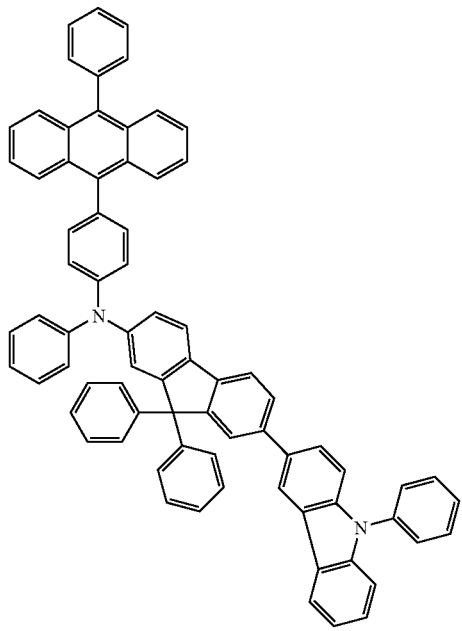

(162)

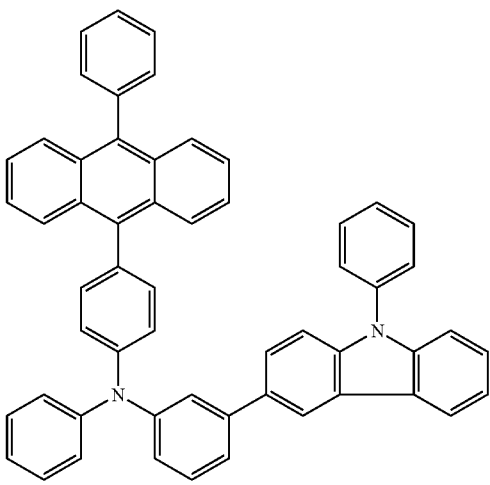

(163)

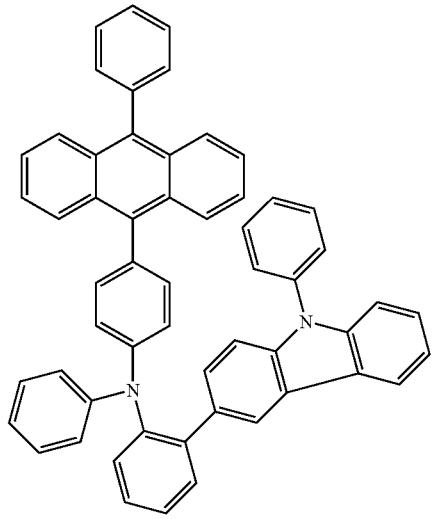

(164)

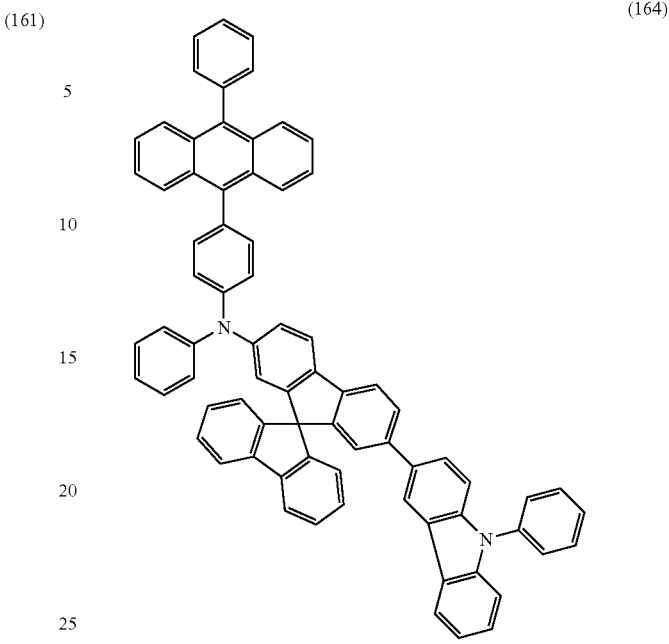

Any of a variety of reactions can be employed for a synthesis method of the anthracene derivatives of the present invention. For example, the synthesis can be performed by use of any of the synthesis methods shown in synthesis schemes (a-1) to (a-3) given below.

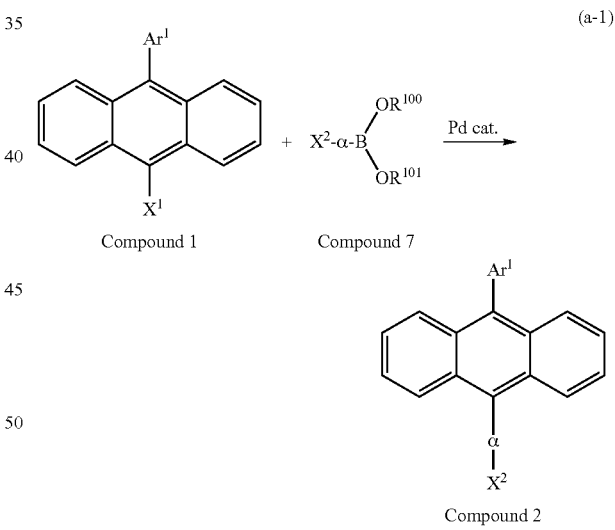

(a-1)

First, 9-halid-10-arylanthracene (Compound 1) and halogenated aryl boronic acid or halogenated aryl organic boron compound (Compound 7) are coupled by Suzuki-Miyaura Coupling using a palladium catalyst, whereby 9-(halogenated aryl)-10-arylanthracene (Compound 2) can be obtained. In the synthesis scheme, $X^1$ represents a halogen or a triflate group, and $X^2$ represents a halogen. When $X^1$ is a halogen, $X^1$ and $X^2$ may be the same or different from each other. Use of iodine and bromine are preferable for the halogen. It is more preferable that $X^1$ be iodine and that $X^2$ be bromine. Further, $R^{100}$ and $R^{101}$ each represent hydrogen or an alkyl group having 1 to 6 carbon atoms, may be the same or different from each other, and may be combined with each other to form a ring. Ar¹ represents a substituted or unsubstituted aryl group having 6 to 25 carbon atoms. α represents a substituted or unsubstituted arylene group having 6 to 25 carbon atoms. Examples of the palladium catalyst that can be used in the synthesis scheme (a-1) include, but are not limited to, palladium(II) acetate, tetrakis(triphenylphosphine)palladium(0), and the like. Examples of the ligand in the palladium catalyst, which can be used in the synthesis scheme (a-1), include, but are not limited to, tri(ortho-tolyl)phosphine, triphenylphosphine, tricyclohexylphosphine, and the like. Examples of the base that can be used in the synthesis scheme (a-1) include, but are not limited to, organic bases such as sodium tert-butoxide, inorganic bases such as potassium carbonate, and the like. Examples of the solvent that can be used in the synthesis scheme (a-1) include, but are not limited to, a mixed solvent of toluene and water; a mixed solvent of toluene, an alcohol such as ethanol, and water; a mixed solvent of xylene and water; a mixed solvent of xylene, an alcohol such as ethanol, and water; a mixed solvent of benzene and water; a mixed solvent of benzene, an alcohol such as ethanol, and water; a mixed solvent of an ether such as ethyleneglycoldimethylether and water; and the like. Use of the mixed solvent of toluene and water or the mixed solvent of toluene, ethanol, and water is more preferable.

tuted aryl group having 6 to 25 carbon atoms, a halogen group, and a haloalkyl group. $R^{102}$ and $R^{103}$ each represent hydrogen or an alkyl group having 1 to 6 carbon atoms, may be the same or different from each other, and combined with each other to form a ring. Examples of the palladium catalyst that can be used in the synthesis scheme (a-2) include, but are not limited to, palladium(II) acetate, tetrakis(triphenylphosphine)palladium(0), and the like. Examples of the ligand that can be used in the synthesis scheme (a-2) include, but are not limited to, tri(ortho-tolyl)phosphine, triphenylphosphine, tricyclohexylphosphine, and the like. Examples of the base that can be used in the synthesis scheme (a-2) include, but are not limited to, organic bases such as sodium tert-butoxide, inorganic bases such as potassium carbonate, and the like. Examples of the solvent that can be used in the synthesis scheme (a-2) include, but are not limited to, a mixed solvent of toluene and water; a mixed solvent of toluene, an alcohol such as ethanol, and water; a mixed solvent of xylene and water; a mixed solvent of xylene, an alcohol such as ethanol, and water; a mixed solvent of benzene and water; a mixed solvent of benzene, an alcohol such as ethanol, and water; a mixed solvent of an ether such as ethyleneglycoldimethylether and water; and the like. Use of the mixed solvent of toluene and water or the mixed solvent of toluene, ethanol, and water is more preferable.

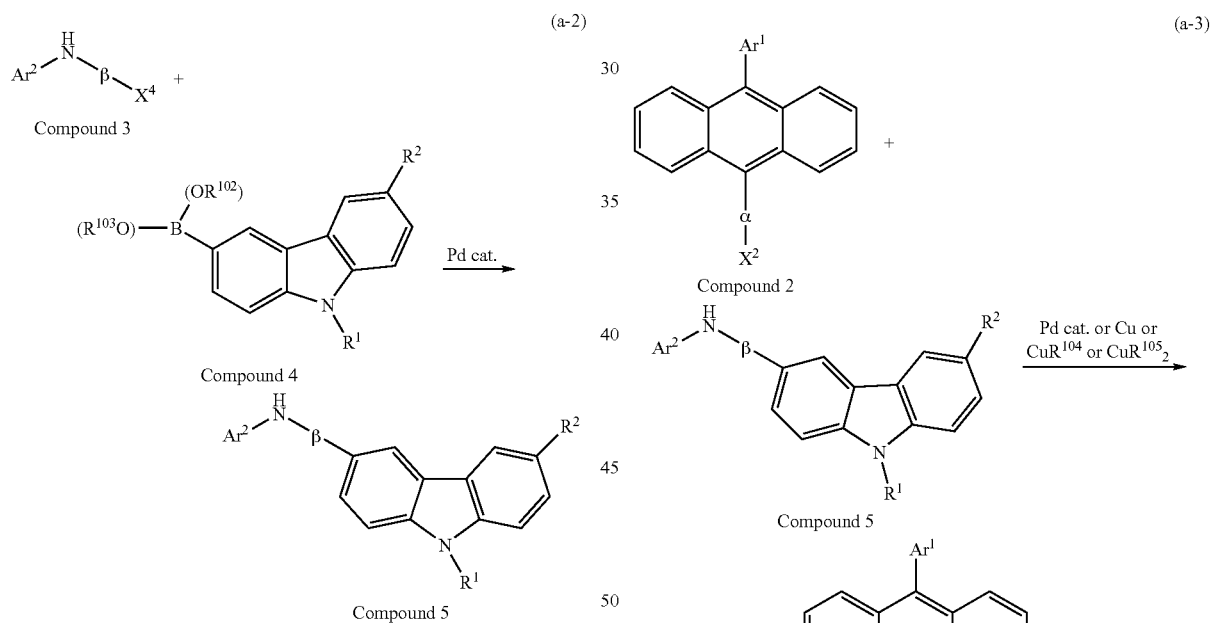

Diarylamine halide (Compound 3) and 9H-carbazole-3-boronic acid or a compound obtained by 9H-carbazole in which the 3-position is substituted with organoboron (Compound 4) are coupled by Suzuki-Miyaura Coupling using a palladium catalyst, whereby a carbazole compound in which the 3-position is substituted with diarylamine (Compound 5) can be obtained. In the synthesis scheme, $Ar^2$ represents a substituted or unsubstituted aryl group having 6 to 25 carbon atoms $X^4$ represents a halogen or a triflate group, and iodine or bromine can be used as the halogen. β represents a substituted or unsubstituted arylene group having 6 to 25 carbon atoms. $R^1$ represents an alkyl group having 1 to 4 carbon atoms or a substituted or unsubstituted aryl group having 6 to 25 carbon atoms. $R^2$ represents one of hydrogen, an alkyl group having 1 to 4 carbon atoms, a substituted or unsubsti- Then, the 9-(halogenated aryl)-10-arylanthracene (Compound 2) obtained by the synthesis scheme (a-1) and the carbazole compound in which the 3-position is substituted with diarylamine (Compound 5) obtained by the synthesis scheme (a-2) are coupled by a Buchwald-Hartwig reaction using a palladium catalyst or an Ullmann reaction using copper or a copper compound, whereby Compound 6 which is one of the anthracene derivatives of the present invention can be obtained. When a Buchwald-Hartwig reaction is performed in the synthesis scheme (a-3), examples of the palladium catalyst that can be used in the synthesis scheme (a-3) include, but are not limited to, bis(dibenzylideneacetone)palladium(0), palladium(II) acetate, and the like. Examples of the ligand in the palladium catalyst, which can be used in the synthesis scheme (a-3), include, but are not limited to, tri(tert-butyl)phosphine, tri(n-hexyl)phosphine, tricyclohexylphosphine, and the like. Examples of the base that can be used in the synthesis scheme (a-3) include, but are not limited to, organic bases such as sodium tert-butoxide, inorganic bases such as potassium carbonate, and the like. Examples of the solvent that can be used in the synthesis scheme (a-3) include, but are not limited to, toluene, xylene, benzene, tetrahydrofuran, and the like. The case in which an Ullmann reaction is performed in the synthesis scheme (a-3) is described. In the synthesis scheme (a-3), $R^{104}$ and $R^{105}$ each represent a halogen, an acetyl group, or the like, and chlorine, bromine, or iodine can be used as the halogen. It is preferred that $R^{104}$ be iodine to form copper(I) iodide or that $R^{105}$ be an acetyl group to form a copper(II) acetate. The copper compound used in the reaction is not limited to these, and copper can be used instead of the copper compound. Examples of the base that can be used in the synthesis scheme (a-3) include, but are not limited to, an inorganic base such as potassium carbonate. Examples of the solvent that can be used in the synthesis scheme (a-3) include, but are not limited to, 1,3-dimethyl-3,4,5,6-tetrahydro-2(1H)pyrimidinone (abbreviated to DMPU), toluene, xylene, benzene, and the like. Use of DMPU or xylene that has a high boiling point is preferable because, by an Ullmann reaction, an object can be obtained in a shorter time and at a higher yield when the reaction temperature is greater than or equal to 100° C. Use of DMPU is more preferable because it is further preferable that the reaction temperature be a temperature greater than or equal to 150° C. In the synthesis scheme, $Ar^1$ and $Ar^2$ may be the same or different from each other and each represent a substituted or unsubstituted aryl group having 6 to 25 carbon atoms. α and β may be the same or different from each other and each represent a substituted or unsubstituted arylene group having 6 to 25 carbon atoms. $X^2$ represents a halogen. $R^1$ represents an alkyl group having 1 to 4 carbon atoms or a substituted or unsubstituted aryl group having 6 to 25 carbon atoms. $R^2$ represents one of hydrogen, an alkyl group having 1 to 4 carbon atoms, a substituted or unsubstituted aryl group having 6 to 25 carbon atoms, a halogen group, and a haloalkyl group.

The anthracene derivatives of the present invention have high emission efficiency. Therefore, it is preferred that any of the anthracene derivatives of the present invention be used for a light-emitting element. Furthermore, the anthracene derivatives of the present invention emit blue light with high color purity. Thus, it is preferred that any of the anthracene derivatives of the present invention be used for a light-emitting device such as a full-color display that displays images. Further, the anthracene derivatives of the present invention can be used as a hole-transporting layer of a light-emitting element since the anthracene derivatives of the present invention have a hole-transporting property.

[Embodiment Mode 2]

In this embodiment mode, organic compounds that are materials used for the synthesis of the anthracene derivatives of the present invention are described. These organic compounds are novel materials and thus included in the present invention.

One of the organic compounds is the organic compound represented by the general formula (8).

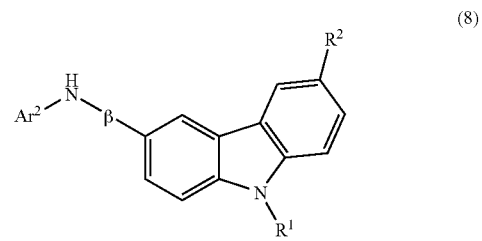

(8)

In the above general formula (8), $Ar^2$ represents a substituted or unsubstituted aryl group having 6 to 25 carbon atoms; β represents a substituted or unsubstituted arylene group having 6 to 25 carbon atoms; $R^1$ represents an alkyl group having 1 to 4 carbon atoms or a substituted or unsubstituted aryl group having 6 to 25 carbon atoms; and $R^2$ represents one of hydrogen, an alkyl group having 1 to 4 carbon atoms, a substituted or unsubstituted aryl group having 6 to 25 carbon atoms, a halogen group, and a haloalkyl group.

Structures shown in (Ar2-1) to (Ar2-19) are given as examples of a substituent represented by $Ar^2$ in the above general formula (8).

(Ar2-1)

(Ar2-2)

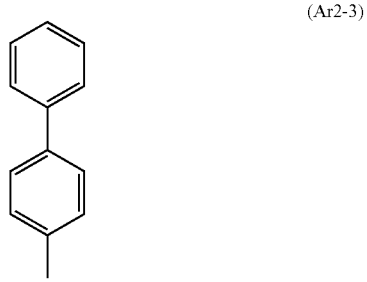

(Ar2-3)

-continued
(Ar2-4)
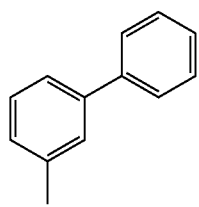
(Ar2-5)
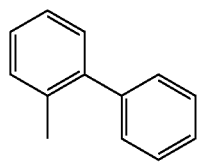
(Ar2-6)
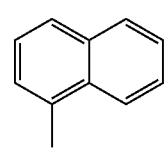
(Ar2-7)
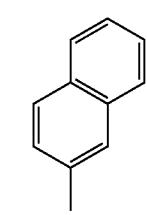
(Ar2-8)
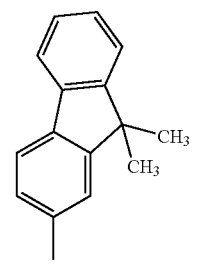
(Ar2-9)
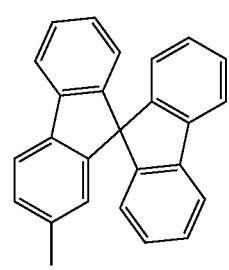
(Ar2-10)
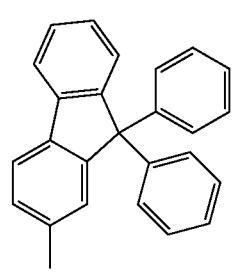
-continued
(Ar2-11)
(Ar2-12)
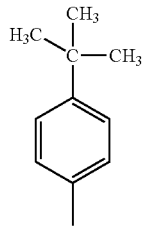
(Ar2-13)
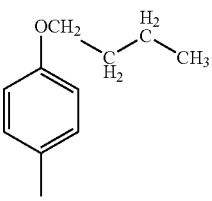
(Ar2-14)
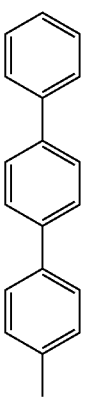
(Ar2-15)
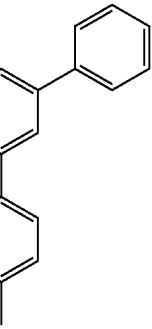
(Ar2-16)
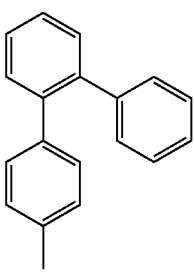

(Ar2-17)
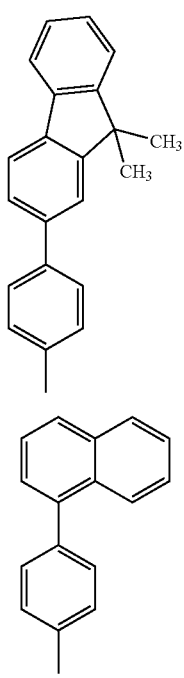
(Ar2-18)
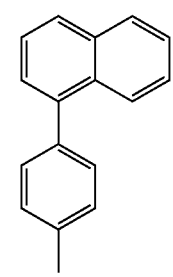
(Ar2-19)
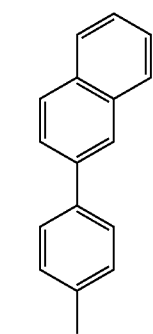
Structures shown in (β-1) to (β-10) are given as examples of a structure represented by β in the above general formula (8).
(β-1)
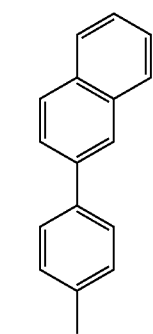
(β-2)
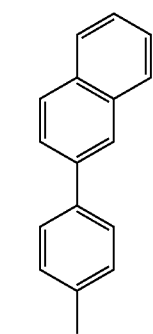
(β-3)
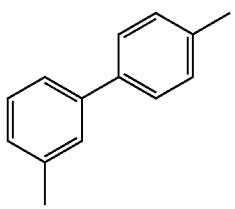
(β-4)
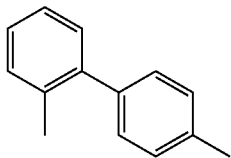
(β-5)
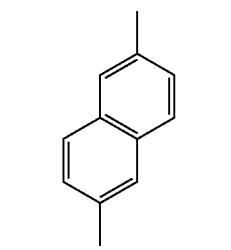
(β-6)
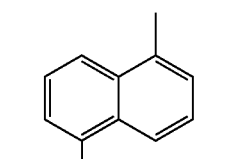
(β-7)
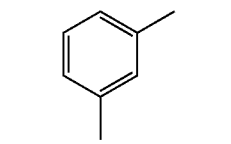
(β-8)
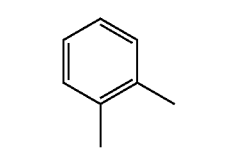
(β-9)
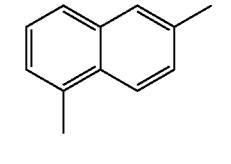
(β-10)
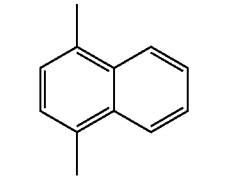
Structures shown in (R1-1) to (R1-21) are given as examples of a substituent represented by $R^1$ in the above general formula (8).

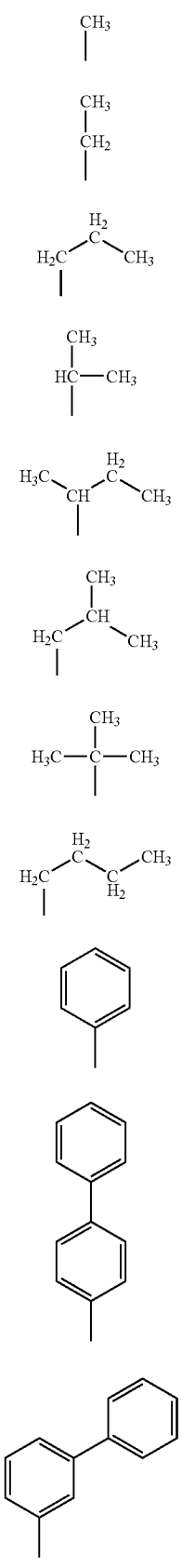

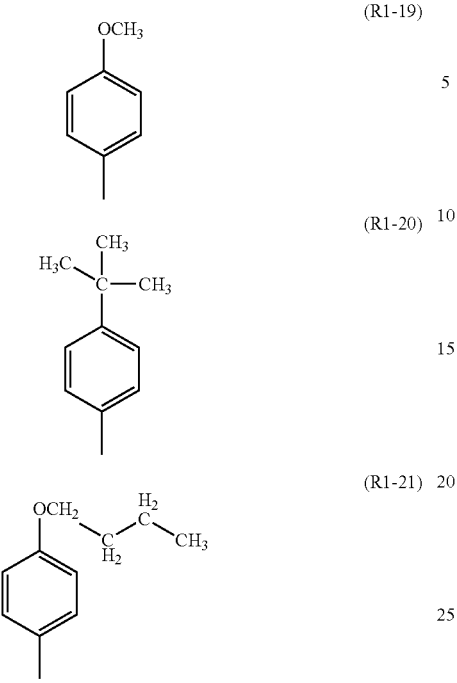
Structures shown in (R2-1) to (R2-24) are given as examples of a substituent represented by R² in the above general formula (8).
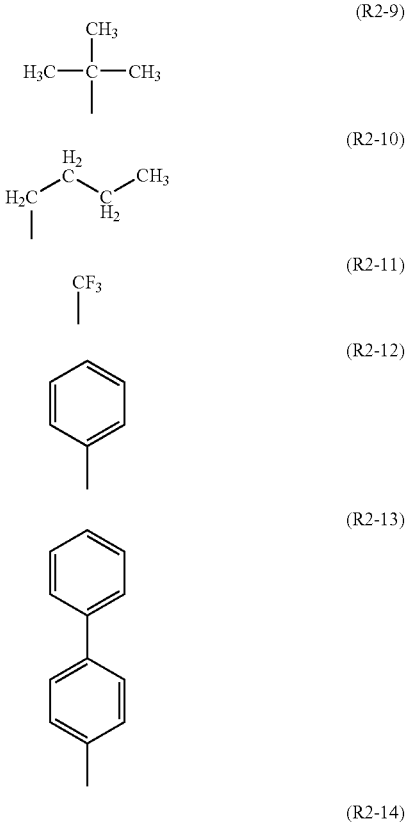
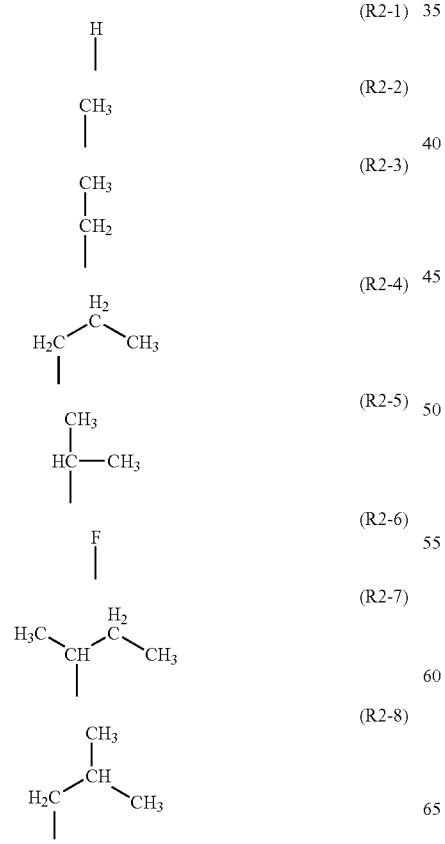

-continued
(R2-18) 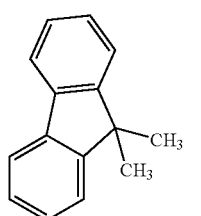
(R2-19) 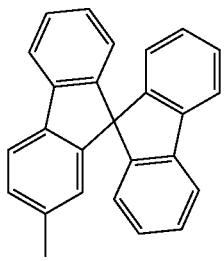
(R2-20) 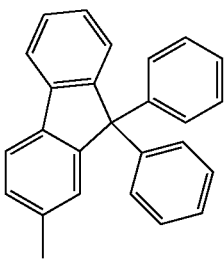
(R2-21) 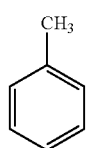
(R2-22) 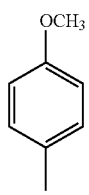
(R2-23) 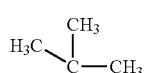
(R2-24) 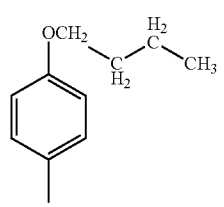
Specific examples of the organic compounds of the present invention include, but are not limited to, organic compounds represented by structural formulae (200) to (264) given below.
(200)
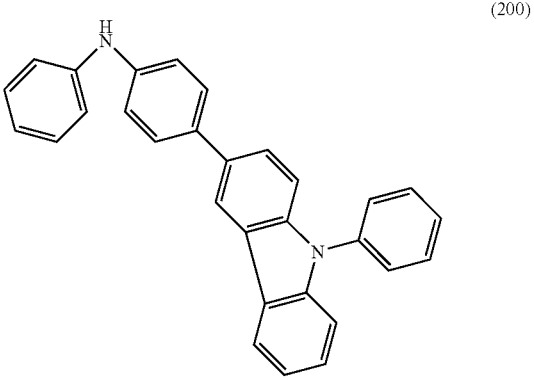
(201)
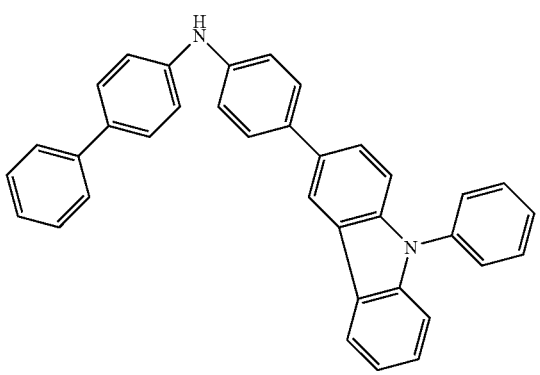
(202)
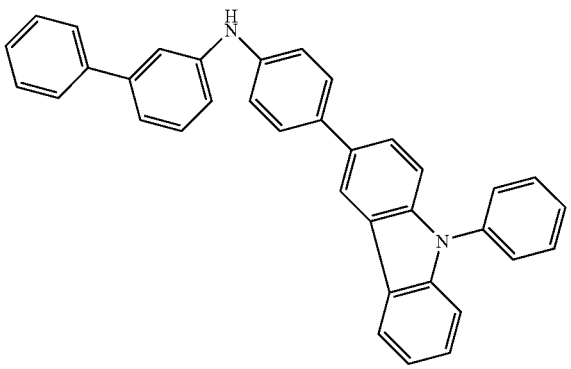

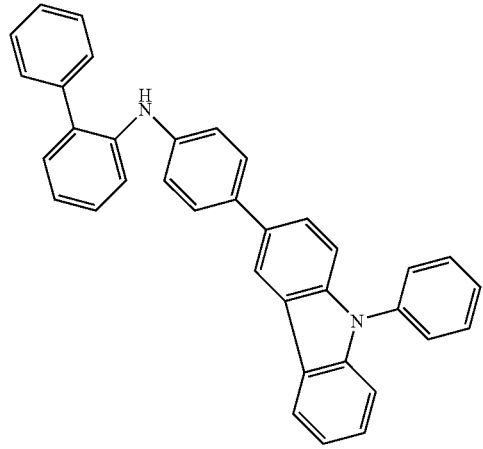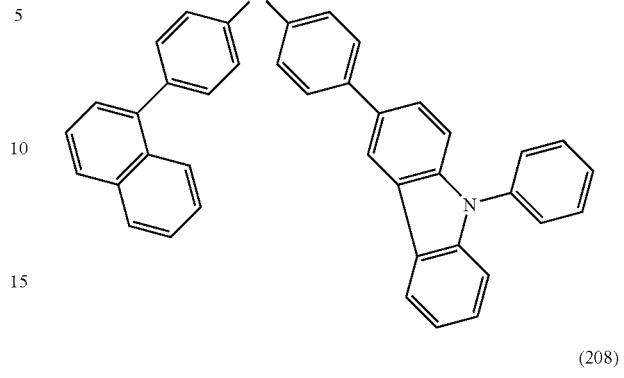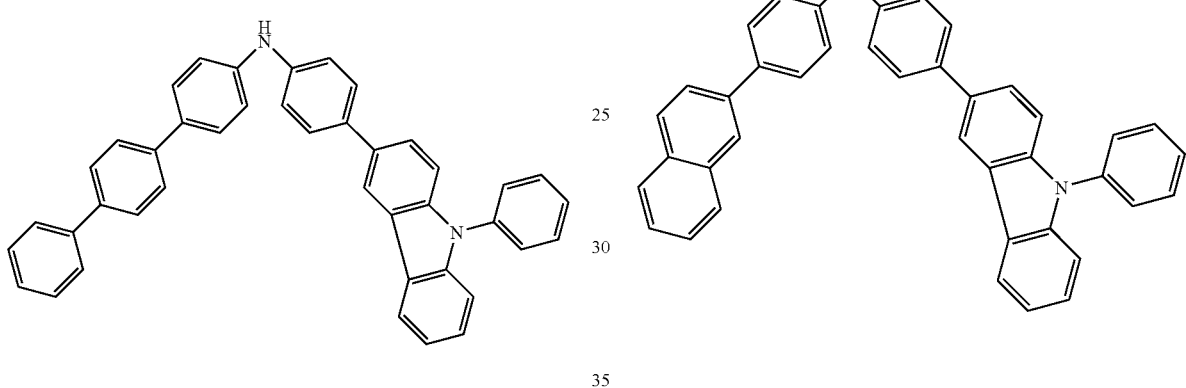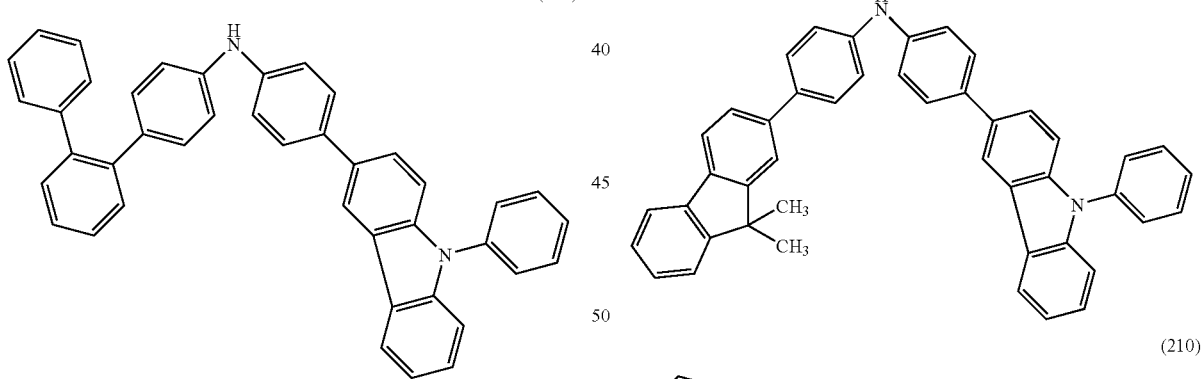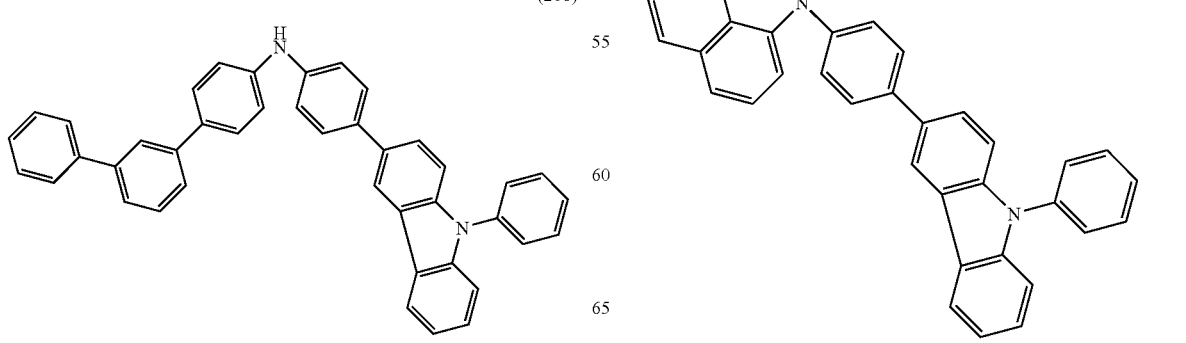

(211)
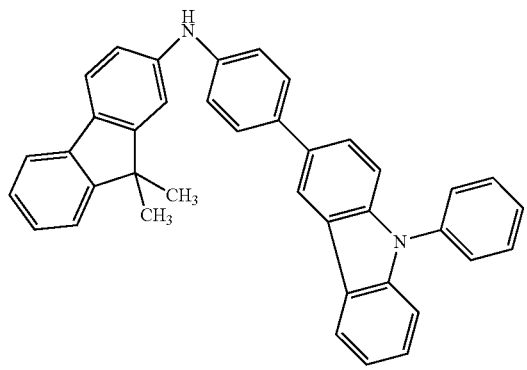
(215)
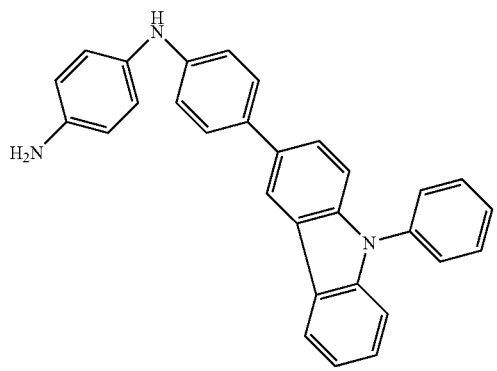
(212)
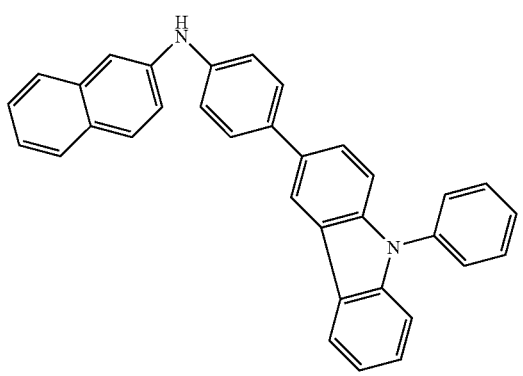
(216)
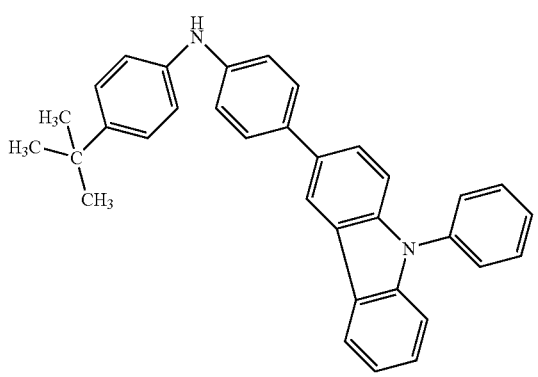
(213)
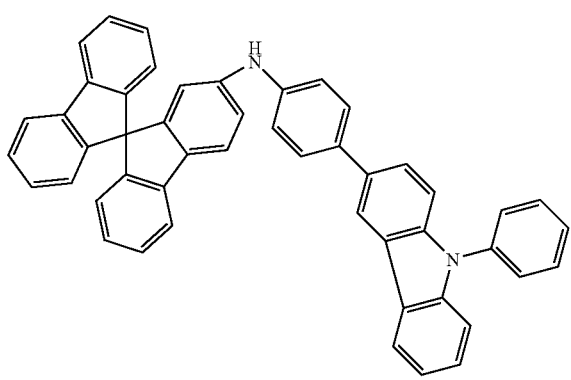
(217)
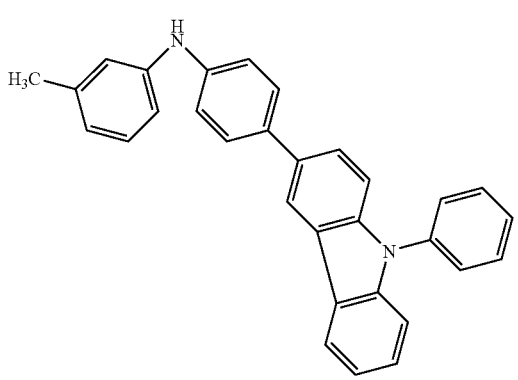
(214)
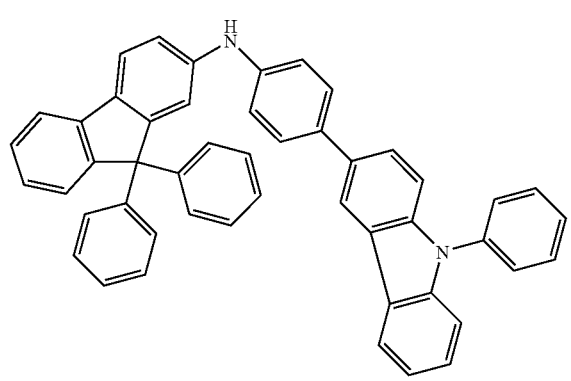
(218)
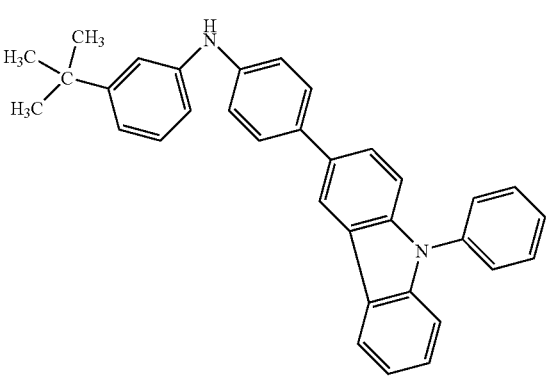

(219)
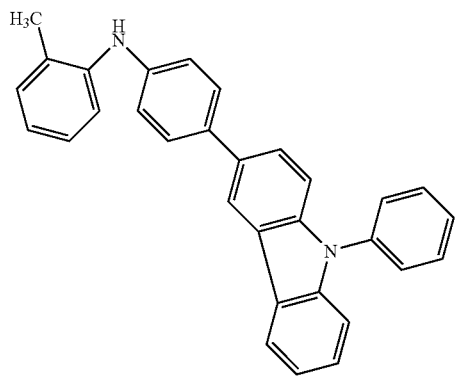
(223)
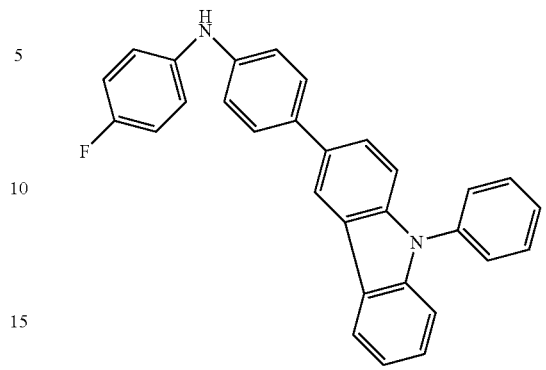
(220)
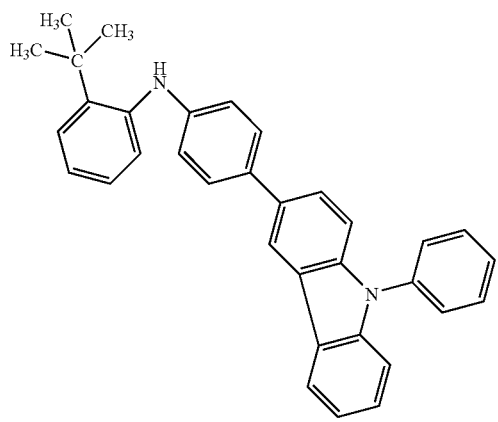
(224)
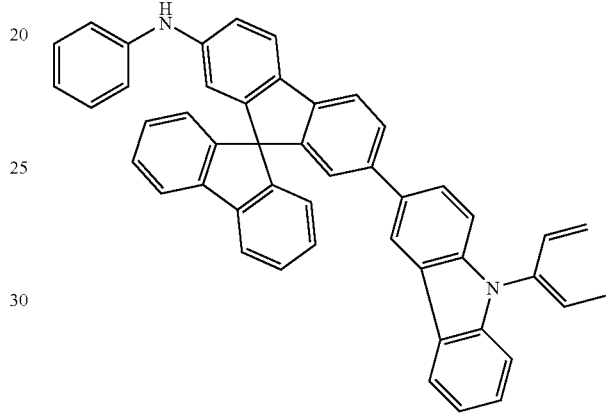
(221)
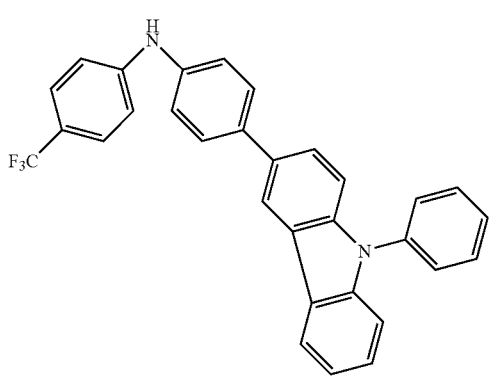
(225)
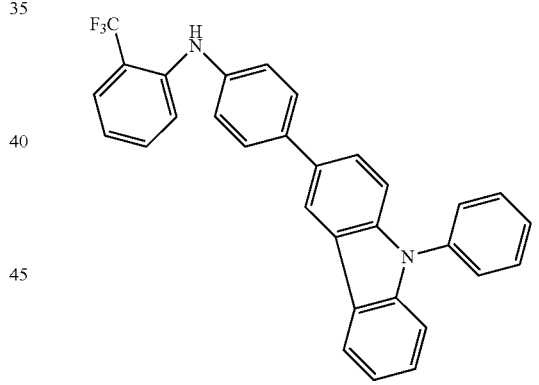
(222)
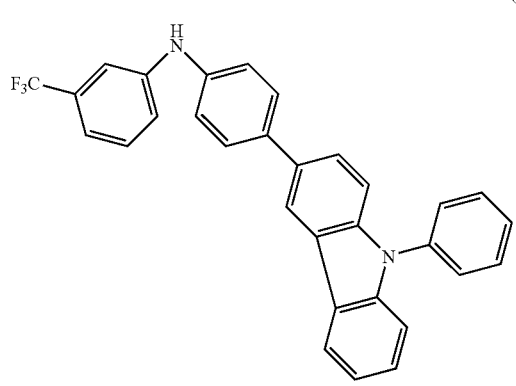
(226)
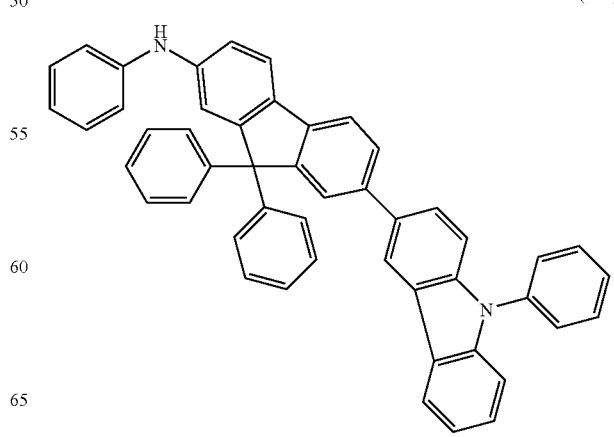

(227)
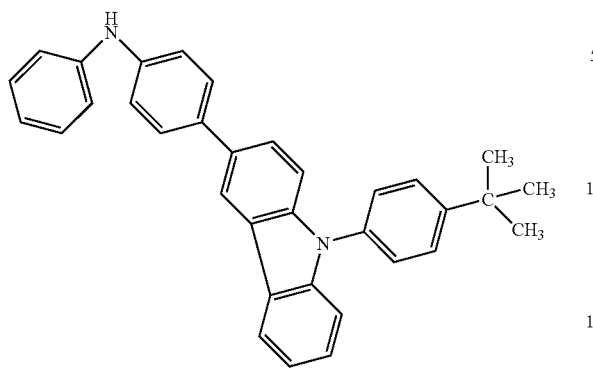
(228)
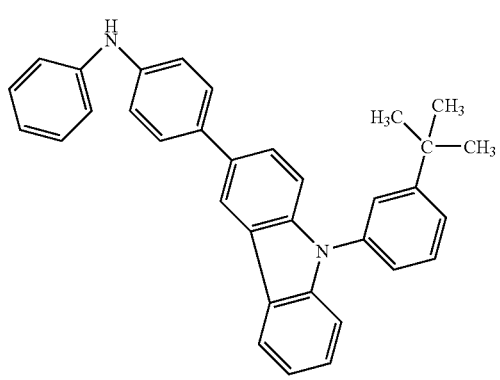
(229)
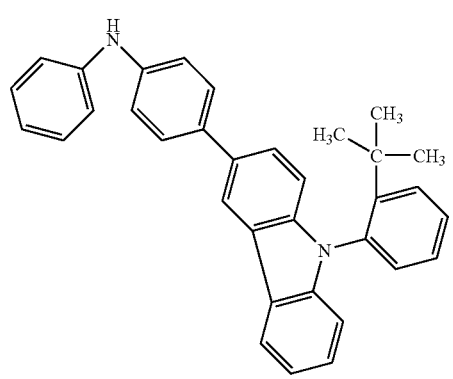
(230)
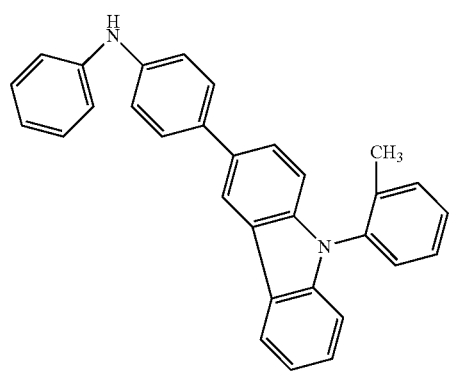
(231)
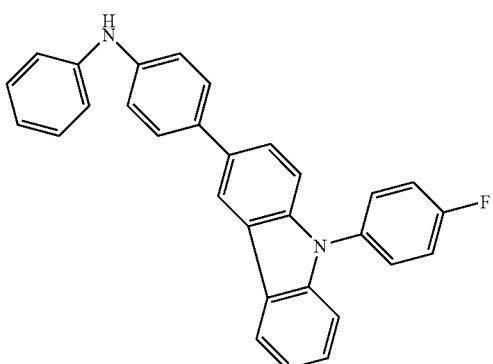
(232)
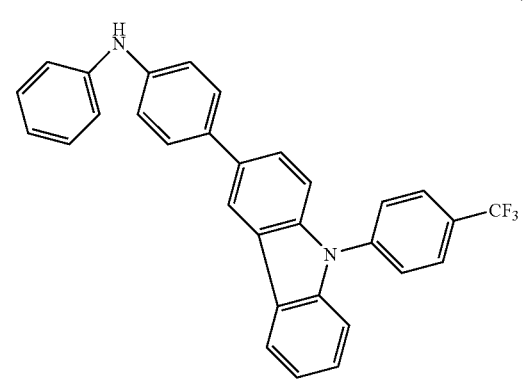
(234)
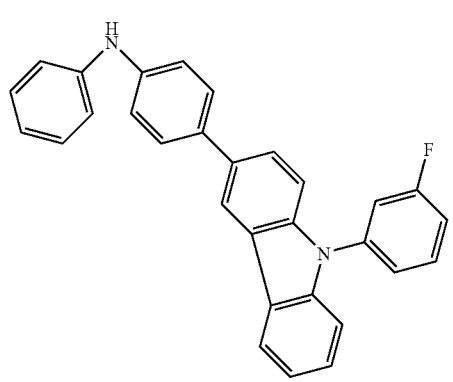
(235)
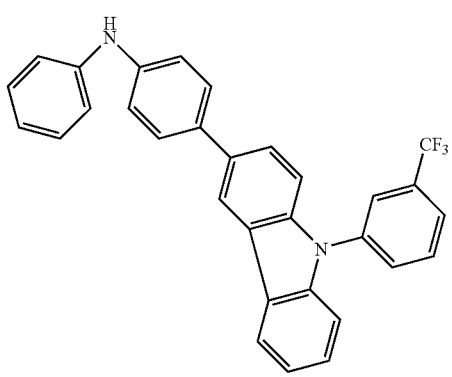

(236)
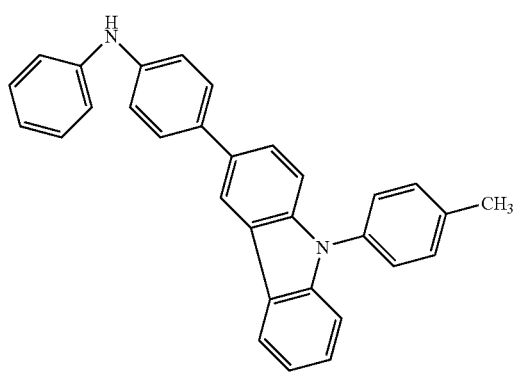
(237)
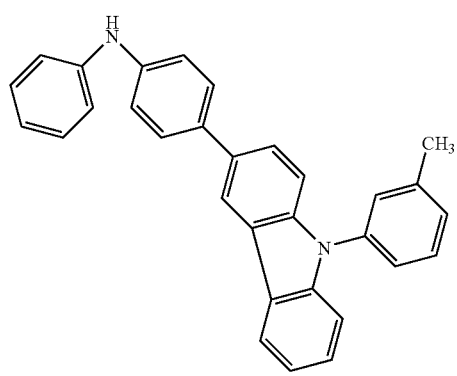
(238)
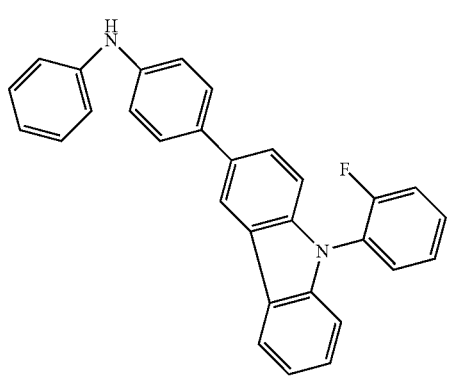
(239)
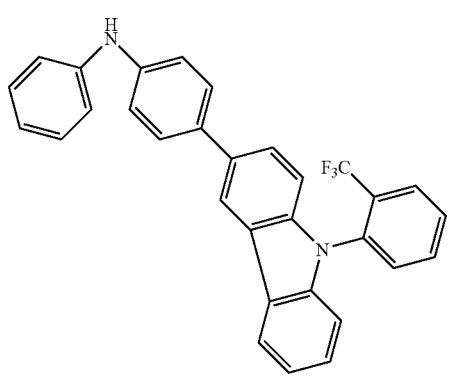
(240)
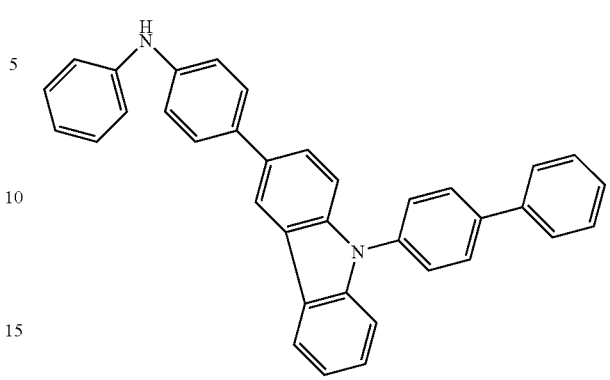
(241)
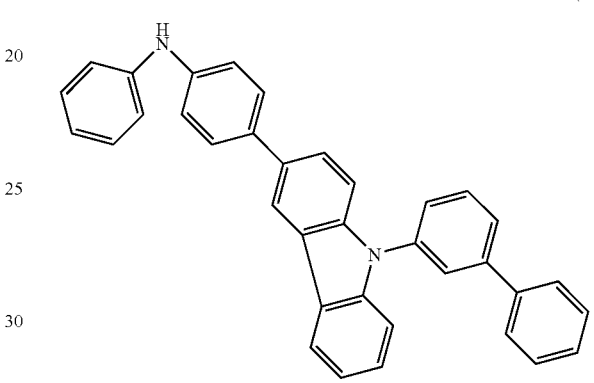
(242)
(243)
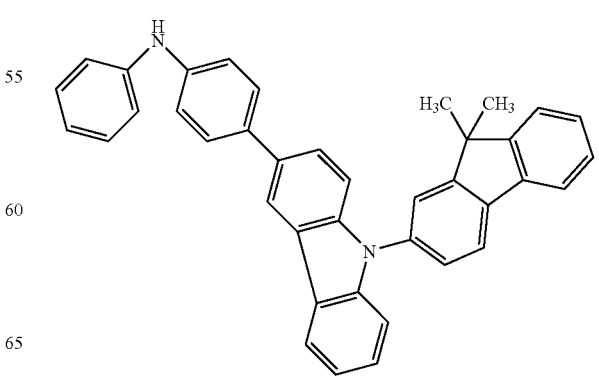

-continued
(244)
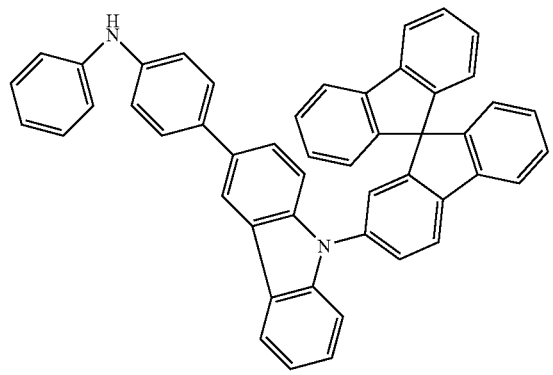
(245)
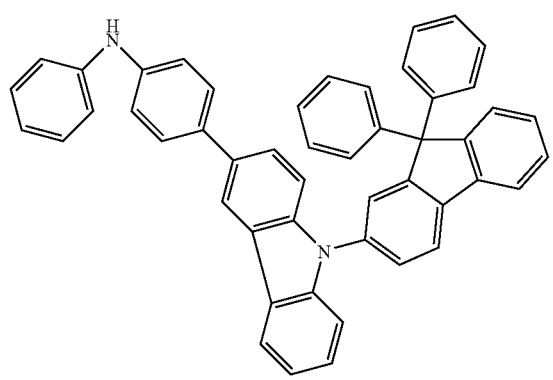
(246)
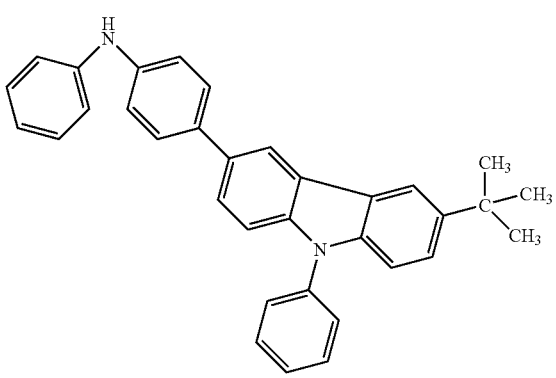
(247)
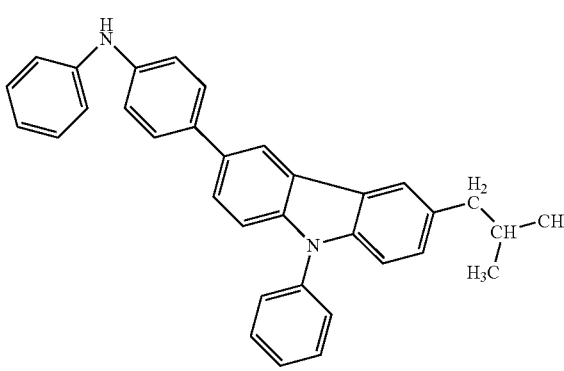
-continued
(248)
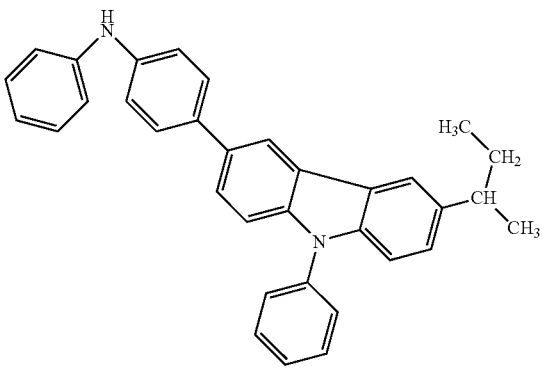
(249)
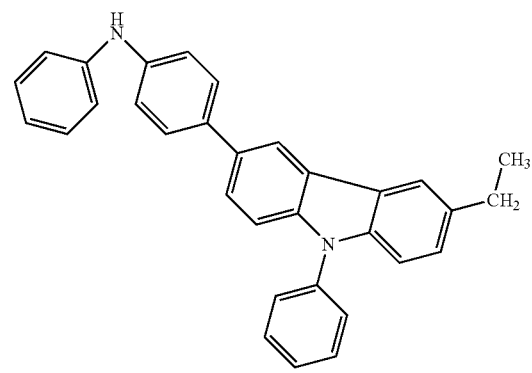
(250)
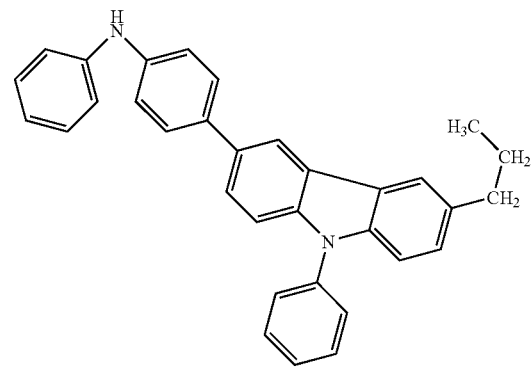
(251)
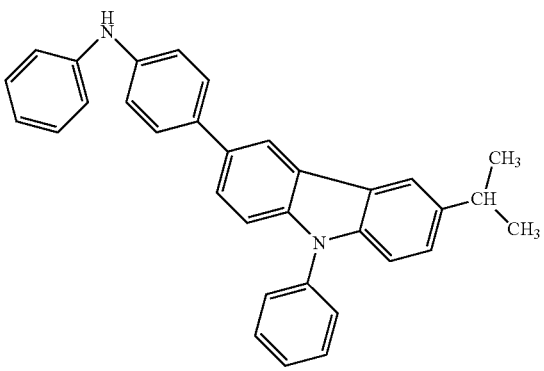

(252)
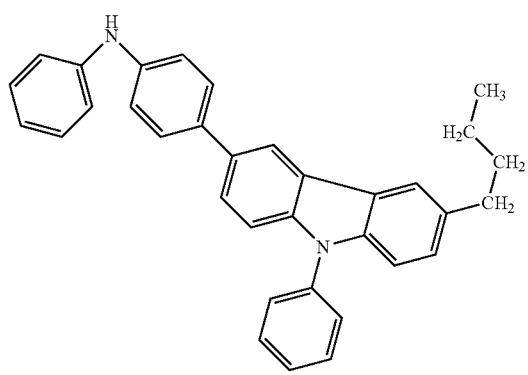
(253)
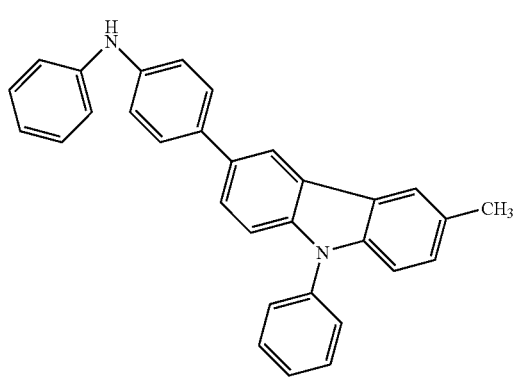
(254)
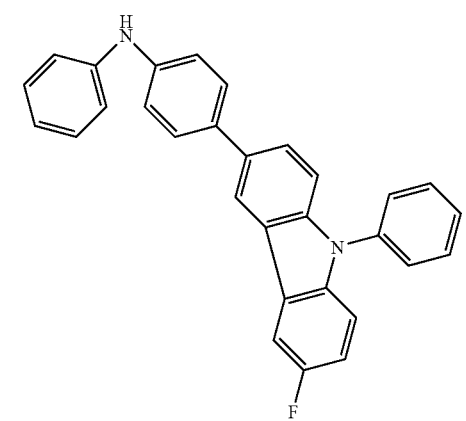
(255)
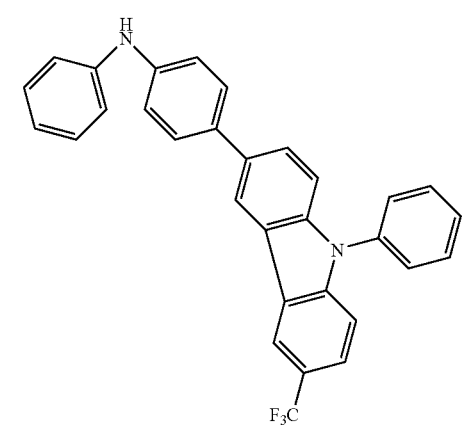
(256)
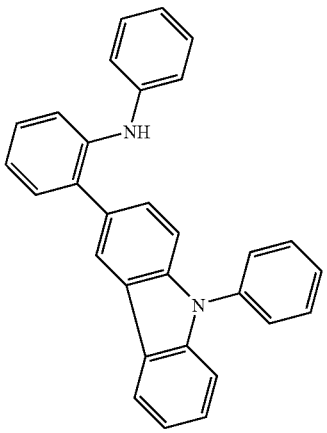
(257)
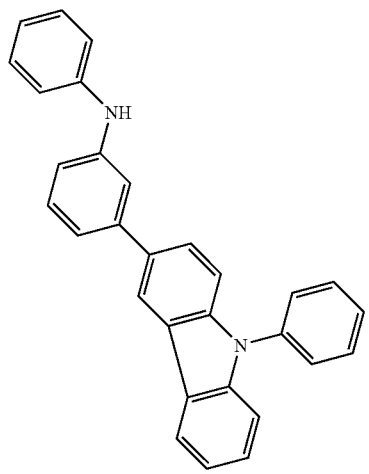
(258)
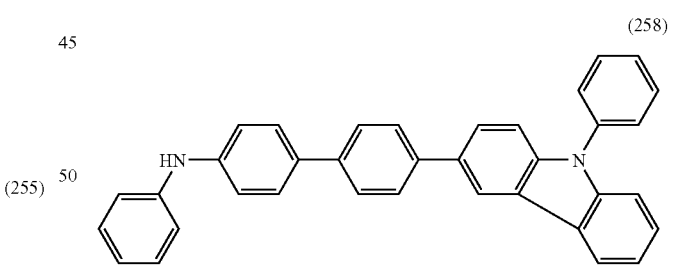
(259)
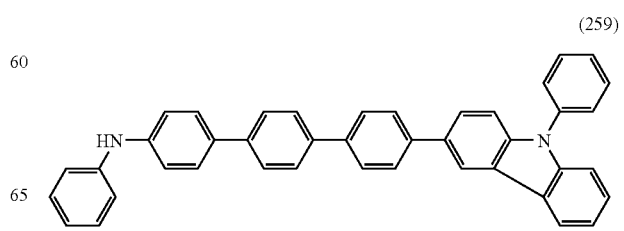

(260)

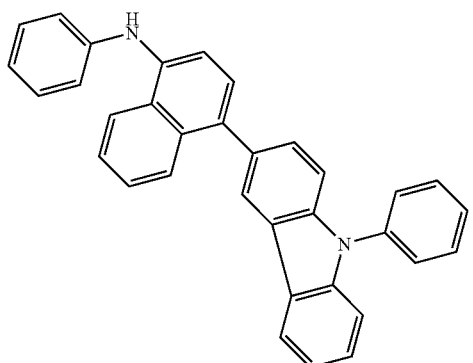

(261)

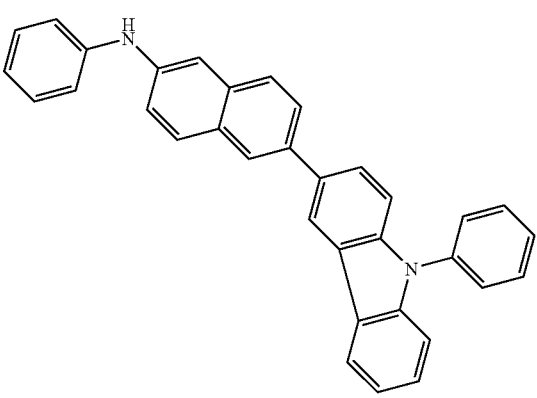

(262)

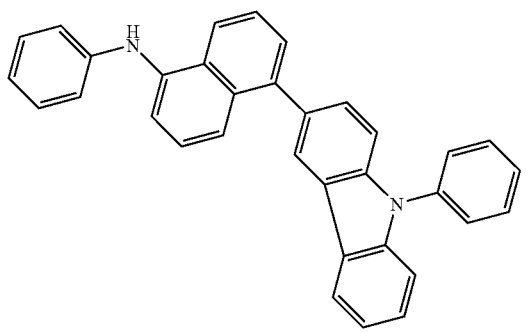

(263)

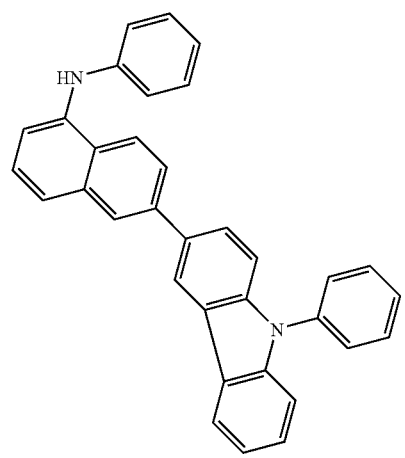

(264)

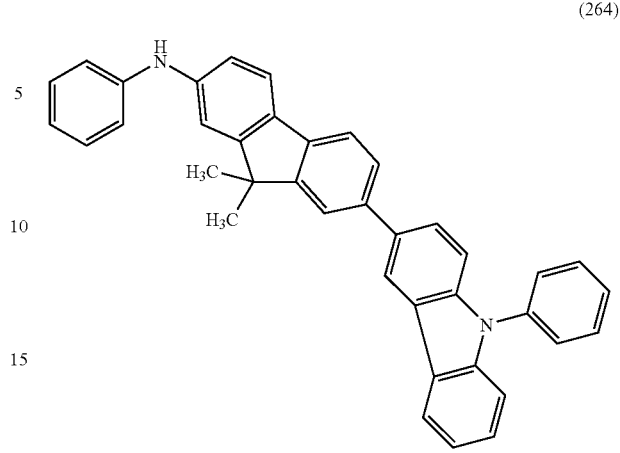

Any of a variety of reactions can be employed for a synthesis method of the above organic compounds of the present invention. For example, the synthesis can be performed by a synthesis method that is similar to that of the compound 5 described in Embodiment Mode 1 (the synthesis scheme (a-2)).

[Embodiment Mode 3]

In this embodiment mode, one mode of a light-emitting element in which any of the anthracene derivatives of the present invention is used is described below using FIG. 1.

The light-emitting element of the present invention includes a plurality of layers between a pair of electrodes. For the plurality of layers, layers that each contain a substance having a high carrier-injecting property or a substance having a high carrier-transporting property are combined and stacked so that a light-emitting region is formed apart from the electrodes, in other words, carriers are recombined in a portion apart from the electrodes.

In this embodiment mode, the light-emitting element includes a first electrode 101, a second electrode 103, and a layer 102 that contains an organic compound formed between the first electrode 101 and the second electrode 103. It is to be noted that, in this embodiment mode, it is assumed that the first electrode 101 serves as an anode and the second electrode 103 serves as a cathode. In other words, in the description below, it is assumed that light emission can be obtained when a voltage is applied to the first electrode 101 and the second electrode 103 so that the potential of the first electrode 101 is higher than that of the second electrode 103.

A substrate 100 is used as a support of the light-emitting element. For the substrate 100, glass, plastic, or the like can be used. It is to be noted that any material other than these can be used as long as it can function as a support in a fabrication process of a light-emitting element.

It is preferred that the first electrode 101 be formed using any of metals, alloys, and conductive compounds with a high work function (specifically, 4.0 eV or higher), a mixture thereof, or the like. Specifically, indium tin oxide (ITO), indium tin oxide containing silicon or silicon oxide, indium zinc oxide (IZO), indium oxide containing tungsten oxide and zinc oxide (IWZO), or the like can be used. Such conductive metal oxide films are typically formed by sputtering, but may also be formed by application of a sol-gel method or the like. For example, a film of indium zinc oxide (IZO) can be formed using a target in which 1 wt % to 20 wt % of zinc oxide is added to indium oxide by a sputtering method. A film of indium oxide containing tungsten oxide and zinc oxide (IWZO) can be formed using a target in which 0.5 wt % to 5 wt % of tungsten oxide and 0.1 wt % to 1 wt % of zinc oxide are added to indium oxide by a sputtering method. Furthermore, gold (Au), platinum (Pt), nickel (Ni), tungsten (W), chromium (Cr), molybdenum (Mo), iron (Fe), cobalt (Co), copper (Cu), palladium (Pd), nitride of a metal material (e.g., titanium nitride), or the like can be used.

When a layer containing a composite material that is described later is used as a layer in contact with the first electrode 101, the first electrode 101 can be formed using any of a variety of metals, alloys, electrically conductive compounds, a mixture thereof or the like regardless of their work functions. For example, aluminum (Al), silver (Ag), an alloy containing aluminum (AlSi), or the like can be used. Alternatively, any of the following materials with a low work function can be used. Group 1 and Group 2 elements of the periodic table, that is, alkali metals such as lithium (Li) and cesium (Cs) and alkaline-earth metals such as magnesium (Mg), calcium (Ca), or strontium (Sr), or alloys thereof (e.g., MgAg and AlLi); rare earth metals such as europium (Eu) or ytterbium (Yb), and alloys thereof; or the like. A film containing an alkali metal, an alkaline earth metal, or an alloy thereof can be formed by a vacuum evaporation method. Alternatively, a film containing an alloy of an alkali metal or an alkaline earth metal can be formed by a sputtering method. Further alternatively, such a film can be formed using a silver paste or the like by an inkjet method or the like.

There is no particular limitation on a stacked structure of a layer 102 containing an organic compound. It is acceptable as long as the layer 102 containing an organic compound is formed by any appropriate combination of a light-emitting layer described in this embodiment mode and layers that each contain a substance having a high electron-transporting property, a substance having a high hole-transporting property, a substance having a high electron-injecting property, a substance having a high hole-injecting property, a bipolar substance (a substance having a high electron-transporting property and a high hole-transporting property), or the like. For example, a hole-injecting layer, a hole-transporting layer, a light-emitting layer, an electron-transporting layer, an electron-injecting layer, and the like can be combined. In this embodiment mode, the layer 102 containing an organic compound has a structure in which a hole-injecting layer 111, a hole-transporting layer 112, a light-emitting layer 113, and an electron-transporting layer 114 are sequentially stacked over the first electrode 101. A material of each layer is described in specific terms below.

The hole-injecting layer 111 is a layer that contains a substance having a high hole-injecting property. Molybdenum oxide, vanadium oxide, ruthenium oxide, tungsten oxide, manganese oxide, or the like can be used. Alternatively, the hole-injecting layer 111 can also be formed using any of phthalocyanine based compounds such as phthalocyanine (abbreviated to H$_2$PC) or copper phthalocyanine (abbreviated to CuPc), aromatic amine compounds such as 4,4'-bis[N-(4-diphenylaminophenyl)-N-phenylamino]biphenyl (abbreviated to DPAB) or 4,4'-bis(N-{4-[N-(3-methylphenyl)-N'-phenylamino]phenyl}-N-phenylamino)biphenyl (abbreviated to DNTPD), compounds with a high molecular weight such as poly(3,4-ethylenedioxythiophene)/poly(styrenesulfonic acid) (abbreviated to PEDOT/PSS), or the like.

Alternatively, for the hole-injecting layer 111, a composite material in which an acceptor substance is mixed into a substance having a high hole-transporting property can be used. It is to be noted that a material of the electrode can be selected regardless of its work function by use of the composite material in which an acceptor substance is mixed into a substance having a high hole-transporting property. That is, not only a material with a high work function, but also a material with a low work function can be used for the first electrode 101. Examples of the acceptor substance include 7,7,8,8-tetracyano-2,3,5,6-tetrafluoroquinodimethane (abbreviated to F$_4$-TCNQ), chloranil, transition metal oxide, oxide of metals that belong to Group 4 to Group 8 of the periodic table, and the like. Specifically, vanadium oxide, niobium oxide, tantalum oxide, chromium oxide, molybdenum oxide, tungsten oxide, manganese oxide, or rhenium oxide is preferably used because of their high electron accepting properties. In particular, use of molybdenum oxide is more preferable because of its stability in the atmosphere, a low hygroscopic property, and easily handling.

As the substance having a high hole-transporting property used for the composite material, any of a variety of compounds such as aromatic amine compounds, carbazole derivatives, aromatic hydrocarbons, compounds with a high molecular weight (such as oligomers, dendrimers, or polymers), or the like can be used. It is to be noted that a substance having a hole mobility of greater than or equal to $10^{-6}$ cm$^2$/(V·s) is preferably used as the substance having a high hole-transporting property. However, any substance other than the above substances may also be used as long as it is a substance in which the hole-transporting property is higher than the electron-transporting property. The organic compounds each of which can be used for the composite material are described in specific terms below.

Examples of the aromatic amine compounds each of which can be used for the composite material include N,N'-bis(4-methylphenyl)(p-tolyl)-N,N'-diphenyl-p-phenylenediamine (abbreviated to DTDPPA), 4,4'-bis[N-(4-diphenylaminophenyl)-N-phenylamino]biphenyl (DPAB), 4,4'-bis(N-{4-[N'-(3-methylphenyl)-N'-phenylamino]phenyl}-N-phenylamino)biphenyl (DNTPD), 1,3,5-tris[N-(4-diphenylaminophenyl)-N-phenylamino]benzene (abbreviated to DPA3B), and the like Specific examples of the carbazole derivatives each of which can be used for the composite material include 3-[N-(9-phenylcarbazol-3-yl)-N-phenylamino]-9-phenylcarbazole (abbreviated to PCzPCA1); 3,6-bis[N-(9-phenylcarbazol-3-yl)-N-phenylamino]-9-phenylcarbazole (abbreviated to PCzPCA2), 3-[N-(1-naphtyl)-N-(9-phenylcarbazol-3-yl)amino]-9-phenylcarbazole (abbreviated to PCzPCN1), and the like.

Moreover, examples of the carbazole derivatives that can be used for the composite material also include 4,4'-di(N-carbazolyl)biphenyl (abbreviated to CBP), 1,3,5-tris[4-(N-carbazolyl)phenyl]benzene (abbreviated to TCPB), 9-[4-(10-phenyl-9-anthryl)phenyl]-9H-carbazole (abbreviated to CzPA), 1,4-bis[4-(N-carbazolyl)phenyl]-2,3,5,6-tetraphenylbenzene, and the like.

Examples of the aromatic hydrocarbons each of which can be used for the composite material include 2-tert-butyl-9,10-di(2-naphthyl)anthracene (abbreviated to t-BuDNA), 2-tert-butyl-9,10-di(1-naphthyl)anthracene, 9,10-bis(3,5-diphenylphenyl)anthracene (abbreviated to DPPA), 2-tert-butyl-9,10-bis(4-phenylphenyl)anthracene (abbreviated to t-BuAnth), 9,10-di(2-naphthyl)anthracene (abbreviated to DNA), 9,10-diphenylanthracene (abbreviated to DPAnth), 2-tert-butylanthracene (abbreviated to t-BuAnth), 9,10-bis(4-methyl-1-naphthyl)anthracene (abbreviated to DMNA), 9,10-bis[2-(1-naphthyl)phenyl]-2-tert-butylanthracene, 9,10-bis[2-(1-naphthyl)phenyl]anthracene, 2,3,6,7-tetramethyl-9,10-di(1-naphthyl)anthracene, 2,3,6,7-tetramethyl-9,10-di(2-naphthyl)anthracene, 9,9'-bianthryl, 10,10'-diphenyl-9,9'-bianthryl, 10,10'-bis(2-phenylphenyl)-9,9'- bianthryl, 10,10'-bis[(2,3,4,5,6-pentaphenyl)phenyl]-9,9'-bianthryl, anthracene, tetracene, rubrene, perylene, 2,5,8,11-tetra(tert-butyl)perylene, and the like. Besides these compounds, pentacene, coronene, or the like can also be used. In particular, use of an aromatic hydrocarbon that has a hole mobility of greater than or equal to $1 \times 10^{-6}$ cm$^2$/(V·s) and has 14 to 42 carbon atoms is more preferable.

It is to be noted that the aromatic hydrocarbons each of which can be used for the composite material may have a vinyl skeleton. Examples of the aromatic hydrocarbons having a vinyl skeleton include 4,4'-bis(2,2-diphenylvinyl)biphenyl (abbreviated to DPVBi), 9,10-bis[4-(2,2-diphenylvinyl)phenyl]anthracene (abbreviated to DPVPA), and the like.

For the hole-injecting layer 111, any of compounds with a high molecular weight (such as oligomers, dendrimers, or polymers) can be used. For example, any of compounds with a high molecular weight such as poly(N-vinylcarbazole) (abbreviated to PVK), poly(4-vinyltriphenylamine) (abbreviated to PVTPA), poly[A-(4-{N'-[4-(4-diphenylamino)phenyl]phenyl-N'-phenylamino}phenyl)methacryla mide] (abbreviated to PTPDMA), and poly[N,N'-bis(4-butylphenyl)-N,N'-bis(phenyl)benzidine] (abbreviated to Poly-TPD) can be given. Further, compounds with a high molecular weight, which is mixed with acid, such as poly(3,4-ethylenedioxythiophene)/poly(styrenesulfonic acid) (PEDOT/PSS) or polyaniline/poly(styrenesulfonic acid) (abbreviated to PAni/PSS) can be used.

Alternatively, for forming the hole-injecting layer 111, the above-described compounds with a high molecular weight, such as PVK, PVTPA, PTPDMA, or Poly-TPD, may be combined with the above-described acceptor substance to form a composite material.

The hole-transporting layer 112 is a layer that contains a substance having a high hole-transporting property. Examples of the substance having a high hole-transporting property include aromatic amine compounds such as 4,4'-bis[N-(1-naphthyl)-N-phenylamino]biphenyl (abbreviated to NPB), N,N'-bis(3-methylphenyl)-N,N'-diphenyl-[1,1'-biphenyl]-4,4'-diamine (abbreviated to TPD), 4,4',4''-tis(N,N-diphenylamino)triphenylamine (abbreviated to TDATA), 4,4',4''-tris[N-(3-methylphenyl)-N-phenylamino]triphenylamine (abbreviated to m-MTDATA), and 4,4'-bis[N-(spiro-9,9'-bifluoren-2-yl)-N-phenylamino]-1,1'-biphenyl (abbreviated to BSPB), and the like. These substances described here mainly are substances each having a hole mobility of greater than or equal to $10^{-6}$ cm$^2$/(V·s). However, any substance other than the above substances may also be used as long as it is a substance in which the hole-transporting property is higher than the electron-transporting property. It is to be noted that the layer that contains a substance having a high hole-transporting property is not limited to a single layer and may be a stack of two or more layers each containing the aforementioned substance.

For the hole-transporting layer 112, compounds with a high molecular weight such as PVK, PVTPA, PTPDMA, or Poly-TPD can also be used.

The light-emitting layer 113 is a layer that contains a substance having a high light-emitting property. In the light-emitting element of this embodiment mode, the light-emitting layer 113 contains any of the anthracene derivatives of the present invention that are described in Embodiment Mode 1. The anthracene derivatives of the present invention are suitable for use in a light-emitting element as a substance having a high light-emitting property because the anthracene derivatives of the present invention exhibit high emission efficiency.

The electron-transporting layer 114 is a layer that contains a substance having a high electron-transporting property. For example, metal complexes having a quinoline or benzoquinoline skeleton, such as tris(8-quinolinolato)aluminum (abbreviated to Alq), tris(4-methyl-8-quinolinolato)aluminum (abbreviated to Almq$_3$), bis(10-hydroxybenzo[h]quinolinato)beryllium (abbreviated to BeBq$_2$), or bis(2-methyl-8-quinolinolato)(4-phenylphenolato)aluminum (abbreviated to BAlq) or the like can be used. Alternatively, metal complexes having an oxazole-based or thiazole-based ligand, such as bis[2-(2-hydroxyphenyl)benzoxazolato]zinc (abbreviated to Zn(BOX)$_2$) or bis[2-(2-hydroxyphenyl)-benzothiazolato]zinc (abbreviated to Zn(BTZ)$_2$) or the like can be used. Instead of the metal complexes, 2-(4-biphenylyl)-5-(4-tert-butylphenyl)-1,3,4-oxadiazole (abbreviated to PBD), 1,3-bis[5-(p-tert-butylphenyl)-1,3,4-oxadiazol-2-yl]benzene (abbreviated to OXD-7), 3-(4-biphenylyl)-4-phenyl-5-(4-tert-butylphenyl)-1,2,4-triazole (abbreviated to TAZ), bathophenanthroline (abbreviated to BPhen), bathocuproine (abbreviated to BCP), or the like can also be used. The substances described here mainly are substances each having an electron mobility of greater than or equal to $10^{-6}$ cm$^2$/(V·s). It is to be noted that any substance other than the above substances may also be used as long it is a substance in which the electron-transporting property is higher than the hole-transporting property. Furthermore, the electron-transporting layer is not limited to a single layer and may be a stack of two or more layers each containing the aforementioned substance.

For the electron-transporting layer 114, any of compounds with a high molecular weight can be used. For example, poly[(9,9-dihexylfluorene-2,7-diyl)-co-(pyridin-3,5-diyl)] (abbreviated to PF-Py), poly[(9,9-dioctylfluorene-2,7-diyl)-co-(2,2'-bipyridin-6,6'-diyl)] (abbreviated to PF-BPy), or the like can be used.

An electron-injecting layer may be provided between the electron-transporting layer 114 and the second electrode 103. The electron-injecting layer can be formed using an alkali metal compound or an alkaline earth metal compound such as lithium fluoride (LiF), cesium fluoride (CsF), or calcium fluoride (CaF$_2$). Furthermore, a layer in which a substance having an electron-transporting property is combined with an alkali metal or an alkaline earth metal can be employed. For example, it is possible to use a layer made of Alq containing magnesium (Mg). It is more preferable to use the layer in which a substance having an electron-transporting property is combined with an alkali metal or an alkaline earth metal as the electron-injecting layer because electron injection from the second electrode 103 efficiently proceeds by the use of such a layer The second electrode 103 can be formed using a metal, an alloy, or a conductive compound with a low work function (specifically, 3.8 eV or lower), a mixture of them, or the like. Specific examples of such cathode materials include elements belonging to Group 1 and Group 2 of the periodic table, that is, alkali metals such as lithium (Li) and cesium (Cs) and alkaline earth metals such as magnesium (Mg), calcium (Ca), and strontium (Sr); alloys of them (e.g., MgAg and AlLi); rare earth metals such as europium (Eu) and ytterbium (Yb), alloys of them; and the like. A film containing an alkali metal, an alkaline earth metal, or an alloy thereof can be formed by a vacuum evaporation method. Alternatively, a film containing an alkali metal, an alkaline earth metal, or an alloy thereof can be formed by a sputtering method. Further alternatively, such a film can be formed using a silver paste or the like by an inkjet method or the like.

Further, when the electron-injecting layer is provided between the second electrode 103 and the electron-transporting layer 114, any of a variety of conductive materials such as Al, Ag, ITO, and ITO containing silicon or silicon oxide can be used for the second electrode 103 regardless of its work function. Films of these conductive materials can be formed by a sputtering method, an inkjet method, a spin coating method, or the like.

In the light-emitting element having the above structure which is described in this embodiment mode, application of a voltage between the first electrode 101 and the second electrode 103 makes current flow, whereby holes and electrons are recombined in the light-emitting layer 113 which is a layer that contains a substance having a high light-emitting property, and light is emitted. That is, a light-emitting region is formed in the light-emitting layer 113.

Light is extracted outside through one or both of the first electrode 101 and the second electrode 103. Thus, one or both of the first electrode 101 and the second electrode 103 are light-transmissive electrodes. When only the first electrode 101 is a light-transmissive electrode, light is extracted from the substrate side through the first electrode 101. In contrast, when only the second electrode 103 is a light-transmissive electrode, light is extracted from a side opposite to the substrate side through the second electrode 103. When both the first electrode 101 and the second electrode 103 are light-transmissive electrodes, light is extracted from both the substrate side and the side opposite to the substrate side through the first electrode 101 and the second electrode 103.

Although FIG. 1 shows a structure in which the first electrode 101 that functions as an anode is provided on the substrate 100 side, the second electrode 103 that functions as a cathode may be provided on the substrate 100 side.

Any of a variety of methods can be employed for forming the layer 102 that contains an organic compound regardless of whether the method is a dry process or a wet process. Further, different deposition methods may be employed for each electrode or layer. A vacuum evaporation method, a sputtering method, or the like can be employed as a dry process. An inkjet method, a spin-coating method, or the like can be employed as a wet process.

Similarly, the electrodes may be formed by a wet process such as a sol-gel process or formed using a metal paste by a wet process. Alternatively, the electrodes may be formed by a dry process such as a sputtering method or a vacuum evaporation method.

Hereinafter, a specific fabrication method of a light-emitting element is described. When a light-emitting element of the present invention is applied to a display device and light-emitting layers are formed separately for each color, it is preferable to form the light-emitting layer by a wet process. The use of a wet process such as an inkjet method makes it easier to form light-emitting layers separately for each color even if a large substrate is employed, whereby productivity is improved.

For example, in the structure described in this embodiment mode, the first electrode may be formed by a sputtering method which is a dry process; the hole-injecting layer may be formed by an inkjet method or a spin coating method which is a wet process; the hole-transporting layer may be formed by a vacuum evaporation method which is a dry process; the light-emitting layer may be formed by an inkjet method which is a wet process; the electron-injecting layer may be formed by a co-deposition method which is a dry process; and the second electrode may be formed by an inkjet method or a spin coating method which is a wet process. Alternatively, the first electrode may be formed by an inkjet method which is a wet process; the hole-injecting layer may be formed by a vacuum evaporation method which is a dry process; the hole-transporting layer may be formed by an inkjet method or a spin coating method which is a wet process; the light-emitting layer may be formed by an inkjet method which is a wet process; the electron-injecting layer may be formed by an inkjet method or a spin coating method which is a wet process; and the second electrode may be formed by an inkjet method or a spin coating method which is a wet process. It is to be noted that there is no limitation on the above methods and a wet process and that a dry process can be combined as appropriate.

Further alternatively, for example, the first electrode can be formed by a sputtering method which is a dry process; the hole-injecting layer and the hole-transporting layer can be formed by an inkjet method or a spin coating method which is a wet process; the light-emitting layer can be formed by an inkjet method which is a wet process; the electron-injecting layer can be formed by a vacuum evaporation method which is a dry process; and the second electrode can be formed by a vacuum evaporation method which is a dry process. In other words, on a substrate on which the first electrode having a desired shape is formed, a wet process can be employed in the formation of the hole-injecting layer to the light-emitting layer, and a dry process can be employed in the formation of the electron-injecting layer to the second electrode. In this method, the formation of the hole-injecting layer to the light-emitting layer can be performed at atmospheric pressure, and the light-emitting layers can be easily formed separately for each color. In addition, the formation of the electron-injecting layer to the second electrode can be performed in vacuum consistently. Thus, the process can be simplified, and productivity can be improved.

In the light-emitting element of the present invention having the structure as described above, the potential difference generated between the first electrode 101 and the second electrode 103 makes current flow, whereby holes and electrons are recombined in the light-emitting layer 113 that is a layer containing a high light-emitting property, and thus light is emitted. That is, a light-emitting region is formed in the light-emitting layer 113.

It is to be noted that the structure of the layers provided between the first electrode 101 and the second electrode 103 is not limited to the above one and may employ any structure as long as the light-emitting region for the recombination of holes and electrons is positioned away from the first electrode 101 and the second electrode 103 so as to prevent quenching caused by the light-emitting region being close to a metal.

The anthracene derivatives have high emission efficiency; therefore, as described in this embodiment mode, any of the anthracene derivatives of the present invention can be used for a light-emitting layer without any need for any other light-emitting substance. Furthermore, since the anthracene derivatives of the present invention have high emission efficiency, a light-emitting element with high emission efficiency can be obtained.

The anthracene derivatives of the present invention emit blue light with high color purity, and thus a light-emitting element that emits blue light with high color purity can be obtained.

Furthermore, the anthracene derivatives of the present invention emit blue light with high color purity at high efficiency, and thus a light-emitting element that can emit blue light with high luminous efficiency can be obtained.

Furthermore, by use of any of the anthracene derivatives of the present invention, a light-emitting element with a long life can be obtained.

Further, since the light-emitting element in which any of the anthracene derivatives of the present invention is used can emit blue light at high efficiency the light-emitting element is suitable for use in a full-color display. Furthermore, the light-emitting element can emit blue light for a long period of time; therefore, the light-emitting element is suitable for use in a full-color display. In particular, the development of blue light-emitting elements lags behind that of red or green light-emitting elements in terms of life and efficiency, and blue light-emitting elements having good characteristics are desired. Since the light-emitting element in which any of the anthracene derivatives of the present invention is used can emit blue light at high efficiency for a long period of time, the light-emitting element is suitable for use in a full-color display.

[Embodiment Mode 4]

In this embodiment mode, a light-emitting element having a structure that is different from that described in Embodiment Mode 3 is described.

In the light-emitting layer 113 described in Embodiment Mode 3, any of the anthracene derivatives of the present invention is dispersed into another substance, whereby light emission from the anthracene derivative of the present invention can be obtained. Since the anthracene derivatives of the present invention emit blue light, a light-emitting element that emits blue light can be obtained.

In this embodiment mode, any of a variety of materials can be used as the substance in which one of the anthracene derivatives of the present invention is dispersed. In addition to the substance having a high hole-transporting property and the substance having a high electron-transporting property, which are described in Embodiment Mode 2, 4,4'-di(N-carbazolyl)-biphenyl (CBP), 2,2',2"-(1,3,5-benzenetriyl)-tris[1-phenyl-1H-benzimidazole] (abbreviated to TPBI), 9,10-di(2-naphthyl)anthracene (DNA), 2-tert-butyl-9,10-di(2-naphthyl)anthracene (t-BuDNA), 9-[4-(10-phenyl-9-anthryl)phenyl]-9H-carbazole (CzPA), or the like can be used. Further, as the substance in which one of the anthracene derivatives of the present invention is dispersed, any of compounds with a high molecular weight can be used. For example, poly(N-vinylcarbazole) (PVK), poly(4-vinyltriphenylamine) (PVTPA), poly[N-(4-{N'-[4-(4-diphenylamino)phenyl]phenyl-N'-phenylamino}phenyl)methacryla mide] (PTPDMA), poly[N,N'-bis(4-butylphenyl)-N,N'-bis(phenyl)benzidine] (Poly-TPD), poly[(9,9-dihexylfluorene-2,7-diyl)-co-(pyridine-3,5-diyl)] (PF-Py), poly[(9,9-dioctylfluorene-2,7-diyl)-co-(2,2'-bipyridin-6,6'-diyl)] (PF-BPy), or the like can be used.

Since the anthracene derivatives of the present invention have high emission efficiency, by use of any of the anthracene derivatives of the present invention in a light-emitting element, a light-emitting element with high emission efficiency can be obtained.

Since the anthracene derivatives of the present invention emit blue light with high color purity, a light-emitting element that emits blue light with high color purity can be obtained.

Furthermore, since the anthracene derivatives of the present invention emit light at high efficiency, a light-emitting element that can emit blue light with high luminous efficiency can be obtained.

Furthermore, by use of any of the anthracene derivatives of the present invention, a light-emitting element with a long life can be obtained.

Since the light-emitting element in which any of the anthracene derivatives of the present invention is used can emit blue light with high color purity at high efficiency, the light-emitting element is suitable for use in a full-color display. Further, since the light-emitting element can emit blue light for a long period of time, the light-emitting element is suitable for use in a full-color display.

It is to be noted that, except for the light-emitting layer 113, the structure described in Embodiment Mode 3 can be used as appropriate.

[Embodiment Mode 5]

In this embodiment mode, a light-emitting element having a structure that is different from the structures described in Embodiment Modes 3 and 4 is described.

In the light-emitting layer 113 described in Embodiment Mode 3, a light-emitting substance is dispersed into any of the anthracene derivatives of the present invention, whereby light emission from the light-emitting substance can be obtained.

When any of the anthracene derivatives of the present invention is used as a material in which another light-emitting substance is dispersed, a color generated by the light-emitting substance can be obtained. Further, a mixture of colors generated by the anthracene derivative of the present invention and the light-emitting substance dispersed in the anthracene derivative can also be obtained.

In this case, any of a variety of materials can be used as the light-emitting substance dispersed in the anthracene derivative of the present invention. Specifically, it is possible to use any of fluorescent substances that emit fluorescence, such as N,N'-diphenylquinacridon (abbreviated to DPQd), coumarin 6, coumarin 545T, 4-(dicyanomethylene)-2-methyl-6-(p-dimethylaminostyryl)-4H-pyran (abbreviated to DCM1), 4-(dicyanomethylene)-2-methyl-6-(julolidin-4-yl-vinyl)-4H-pyran (abbreviated to DCM2), N,N-dimethylquinacridone (abbreviated to DMQd), {2-(1,1-dimethylethyl)-6-[2-(2,3,6,7-tetrahydro-1,1,7,7-tetramethyl-1H,5H-benzo[ij]quinolizin-9-yl)ethenyl]-4H-pyran-4-ylidene}propanedinitrile (abbreviated to DCJTB), 5,12-diphenyltetracene (abbreviated to DPT), 4-(9H-carbazol-9-yl)-4'-(10-phenyl-9-anthryl)triphenylamine (abbreviated to YGAPA), 4,4'-(2-tert-butylanthracen-9,10-diyl)bis{N-[4-(9H-carbazol-9-yl)phenyl]-N-phenylanili ne} (abbreviated to YGABPA), N,9-diphenyl-N-[4-(10-phenyl-9-anthryl)phenyl]-9H-carbazol-3-amine (abbreviated to PCAPA), N,N'''-(2-tert-butylanthracene-9,10-diyldi-4,1-phenylene)bis[N,N',N'-triphenyl-1,4-pheny lenediamine] (abbreviated to DPABPA), N,N'-bis[4-(9H-carbazol-9-yl)phenyl]-N,N'-diphenylstilbene-4,4'-diamine (abbreviated to YGA2S), N-[4-(9H-carbazol-9-yl)phenyl]-N-phenylstilben-4-amine (abbreviated to YGAS), N,N'-diphenyl-N,N'-bis(9-phenylcarbazol-3-yl)stilbene-4,4'-diamine (abbreviated to PCA2S), 4,4'-bis(2,2-diphenylvinyl)biphenyl (DPVBi), 2,5,8,11-tetra(tert-butyl)perylene (abbreviated to TBP), perylene, rubrene, and 1,3,6,8-tetraphenylpyrene. Moreover, any of phosphorescent substances that emit phosphorescence such as (acetylacetonato)bis[2,3-bis(4-fluorophenyl)quinoxalinato]iridium(III) (abbreviated to Ir(Fdpq)2(acac)), and (2,3,7,8,12,13,17,18-octaethyl-21H,23H-porphyrinato)platinum(II) (abbreviated to PtOEP) can be used.

It is to be noted that, except for the light-emitting layer 113, the structure described in Embodiment Mode 3 can be employed as appropriate.

[Embodiment Mode 6]

Figure 2:
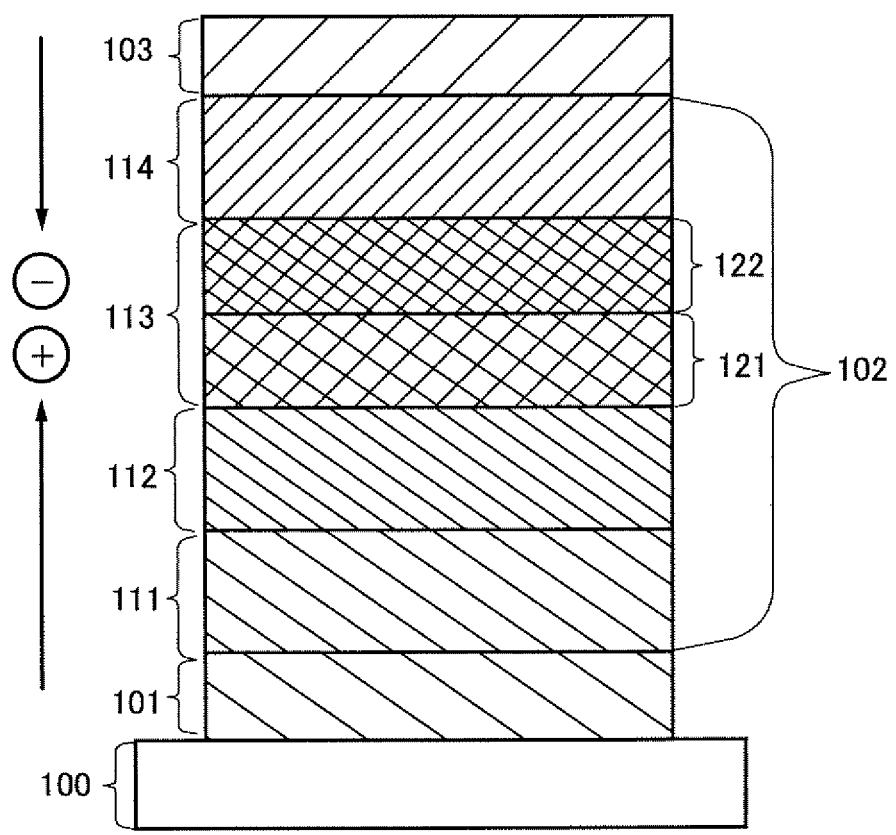
FIG. 2 illustrates a light-emitting element of the present invention.

In this embodiment mode, a light-emitting element having a structure that is different from the structures described in Embodiment Modes 3 to 5 is described using FIG. 2.

In the light-emitting element described in this embodiment mode, a first layer 121 and a second layer 122 are provided in the light-emitting layer 113 of the light-emitting element described in Embodiment Mode 3.

The light-emitting layer 113 is a layer that contains a substance having a high light-emitting property. In the light-emitting element of the present invention, the light-emitting layer 113 has the first layer 121 and the second layer 122. The first layer 121 contains a first organic compound and an organic compound having a hole-transporting property, and the second layer 122 contains a second organic compound and an electron-transporting organic compound. The first layer 121 is provided on the first electrode side of the second layer 122, in other words, in contact with an anode side of the second layer 122.

Each of the first organic compound and the second organic compound is a substance having a high light-emitting property. In the light-emitting element described in this embodiment mode, the first organic compound or the second organic compound contains any of the anthracene derivatives of the present invention which are described in Embodiment Mode 1. Since the anthracene derivatives of the present invention emit blue light with high color purity, the anthracene derivatives are each suitable for use as a substance having a high light-emitting property in the light-emitting element described in this embodiment mode. The first organic compound and the second organic compound may be the same or different from each other.

When any of the anthracene derivatives of the present invention is used as one of the first organic compound and the second organic compound, as the other one thereof, it is possible to use substances that emit bluish light, such as 4-(9H-carbazol-9-yl)-4'-(10-phenyl-9-anthryl)triphenylamine (YGAPA), 4,4'-(2-tert-butylanthracen-9,10-diyl)bis{N-[4-(9H-carbazol-9-yl)phenyl]-N-phenylanili ne} (YGABPA), N,9-diphenyl-N-[4-(10-phenyl-9-anthryl)phenyl]-9H-carbazol-3-amine (PCAPA), N,N''-(2-tert-butylanthracene-9,10-diyldi-4,1-phenylene)bis[N,N',N'-triphenyl-1,4-phen ylenediamine] (DPABPA), N,N'-bis[4-(9H-carbazol-9-yl)phenyl]-N,N'-diphenylstilbene-4,4'-diamine (YCA2S), N-[4-(9H-carbazol-9-yl)phenyl]-N-phenylstilbene-4-amine (YGAS), N,N'-diphenyl-N,N'-bis(9-phenylcarbazol-3-yl)stilbene-4,4'-diamine (PCA2S), 4,4'-bis(2,2-diphenylvinyl)biphenyl (DPVBi), 2,5,8,11-tetra(tert-butyl)perylene (TBP), perylene, rubrene, and 1,3,6,8-tetraphenylpyrene. Since each of these substances exhibits light of a color that is similar to that of each anthracene derivatives of the present invention, they are suitable for use in the light-emitting element of this embodiment mode.

The organic compound having a hole-transporting property, which is contained in the first layer 121, is a substance in which the hole-transporting property is higher than the electron-transporting property. The organic compound having an electron-transporting property, which is contained in the second layer 122, is a substance in which the electron-transporting property is higher than the hole-transporting property.

The light-emitting element of the present invention having the above-described structure is described using FIG. 2 in accordance with the principle below.

In FIG. 2, holes injected from the first electrode 101 are injected into the first layer 121. The holes injected into the first layer 121 are transported through the first layer 121 and further injected into the second layer 122. At this time, since the organic compound having an electron-transporting property, which is contained in the second layer 122, is a substance in which the electron-transporting property is higher than the hole-transporting property, the holes injected into the second layer 122 have difficulty moving. Consequently, a large number of holes come to be present near the interface between the first layer 121 and the second layer 122. In addition, occurrence of a phenomenon in which holes reach the electron-transporting layer 114 without recombining with electrons can be suppressed.

On the other hand, electrons injected from the second electrode 103 are injected into the second layer 122. The electrons injected into the second layer 122 are transported through the second layer 122 and further injected into the first layer 121. At this time, since the organic compound having a hole-transporting property, which is contained in the first layer 121, is a substance in which the hole-transporting property is higher than the electron-transporting property, the electrons injected into the first layer 121 have difficulty moving. Consequently, a large number of electrons come to be present near the interface between the first layer 121 and the second layer 122. In addition, occurrence of a phenomenon in which electrons reach the hole-transporting layer 112 without recombining with holes can be suppressed.

As described above, a large number of holes and electrons come to be present in a region in the vicinity of the interface between the first layer 121 and the second layer 122, and thus, the probability of recombination in the region in the vicinity of the interface can be increased. That is, the light-emitting region is formed in the vicinity of the center of the light-emitting layer 113. As a result, occurrence of a phenomenon in which holes reach the electron-transporting layer 114 without recombining with electrons or electrons reach the hole-transporting layer 112 without recombining with holes can be suppressed, whereby a reduction in the probability of recombination can be prevented. Since a reduction of carrier balance over time can thus be prevented, an improvement in reliability is promoted.

In order that holes and electrons be injected into the first layer 121, it is preferred that the organic compound having a hole-transporting property be an organic compound which can be oxidized and reduced and has a highest occupied molecular orbital level (HOMO level) of greater than or equal to −6.0 eV and less than or equal to −5.0 eV as well as a lowest unoccupied molecular orbital level (LUMO level) of greater than or equal to −3.0 eV and less than or equal to −2.0 eV.

As such an organic compound that can be oxidized and reduced, use of anthracene derivatives is particularly preferable among tricyclic polyacene derivatives, tetracyclic polyacene derivatives, pentacyclic polyacene derivatives, and hexacyclic polyacene derivatives. Specific examples of the organic compound having an hole-transporting property, which is contained in the first layer 121, include 9,10-diphenylanthracene (DPAnth), N,N-diphenyl-9-[4-(10-phenyl-9-anthryl)phenyl]-9H-carbazol-3-amine (abbreviated to CzA1PA), 4-(10-phenyl-9-anthryl)triphenylamine (abbreviated to DPhPA), N,9-diphenyl-N-[4-(10-phenyl-9-anthryl)phenyl]-9H-carbazol-3-amine (PCAPA), N,9-diphenyl-N-{4-[4-(10-phenyl-9-anthryl)phenyl]phenyl}-9H-carbazol-3-amine (abbreviated to PCAPBA), and the like.

Similarly, in order that holes and electrons be injected into the second layer 122, it is preferred that the organic compound having an electron-transporting property be an organic compound which can be oxidized and reduced and has a HOMO level of greater than or equal to −6.0 eV and less than or equal to −5.0 eV.

As such an organic compound which can be oxidized and reduced, any of tricyclic polyacene derivatives, tetracyclic polyacene derivatives, pentacyclic polyacene derivatives, or hexacyclic polyacene derivatives can be given. Specifically, any of anthracene derivatives, phenanthrene derivatives, pyrene derivatives, chrysene derivatives, dibenzo[g,p]chrysene derivatives, or the like can be given. For example, as a compound having an electron-transporting property, which can be used for the second layer, 9-[4-(10-phenyl-9-anthryl)phenyl]-9H-carbazole (CzPA), 3,6-diphenyl-9-[4-(10-phenyl-9-anthryl)phenyl]-9H-carbazole (abbreviated to DPCzPA), 9,10-bis(3,5-diphenylphenyl)anthracene (DPPA), 9,10-di(2-naphthyl)anthracene (DNA), 2-tert-butyl-9,10-di(2-naphthyl)anthracene (abbreviated to t-BuDNA), 9,9'-bianthryl (abbreviated to BANT), 9,9'-(stilbene-3,3'-diyl)diphenanthrene (abbreviated to DPNS), 9,9'-(stilbene-4,4'-diyl)diphenanthrene (abbreviated to DPNS2), 3,3',3"-(benzene-1,3,5-triyl)tripyrene (abbreviated to TPB3), and the like can be given.

As described above using FIG. 2, the light-emitting element of the present invention has a structure in which holes are injected into the second layer 122 from the first layer 121. Therefore, it is preferable that the difference in HOMO level between that of the organic compound having a hole-transporting property and that of the organic compound having an electron-transporting property be small. Further, since the light-emitting element of the present invention has a structure in which electrons are injected into the first layer 121 from the second layer 122, it is preferable that the difference in LUMO level between that of the organic compound having a hole-transporting property and that of the organic compound having an electron-transporting property be small. If the difference in HOMO level between that of organic compound having a hole-transporting property and that of the organic compound having an electron-transporting property is large, the light-emitting region is formed more on the first layer side or on the second layer side. Similarly, if the difference in LUMO level between that of the organic compound having a hole-transporting property and that of the organic compound having an electron-transporting property is large, the light-emitting region is formed more on the first layer side or on the second layer side. Accordingly, the difference between the HOMO level of the organic compound having a hole-transporting property and that of the organic compound having an electron-transporting property is preferably 0.3 eV or less, and more preferably, 0.1 eV or less. The difference between the LUMO level of the organic compound having a hole-transporting property and that of the organic compound having an electron-transporting property is preferably 0.3 eV or less, and more preferably, 0.1 eV or less.

Since light can be emitted from the light-emitting element by recombination of electrons and holes, it is preferable that the organic compound used for the light-emitting layer 113 be stable with respect to repetitive redox reactions. In other words, it is preferable that the organic compound be able to be reversibly oxidized and reduced. In particular, it is preferable that the organic compound having a hole-transporting property and the organic compound having an electron-transporting property be stable with respect to repetitive redox reactions. Whether the organic compounds are stable with respect to repetitive redox reactions or not can be confirmed by cyclic voltammetry (CV) measurements.

Specifically, whether the organic compounds are stable with respect to repetitive redox reactions or not can be confirmed by measurement of changes in the value of an oxidation peak potential ($E_{pa}$) of an oxidation reaction of the organic compound and the value of a reduction peak potential ($E_{pc}$) of a reduction reaction, changes in the shape of the peaks, and the like. In the organic compound having a hole-transporting property and the organic compound having an electron-transporting property which are used for the light-emitting layer 113, the amount of change in the intensity of the oxidation peak potential or the intensity of the reduction peak potential is preferably less than 50%, and more preferably, less than 30%. In other words, for example, where the oxidation peak decreases, the intensity of the peak is preferably kept at 50% or more, more preferably, 70%. In addition, the amount of change in the values of the oxidation peak potential and the reduction peak potential is preferably 0.05 V or lower, more preferably, 0.02 V or lower.

Furthermore, when the substance having a high light-emitting property contained in the first layer and the substance having a high light-emitting property contained in the second layer are different, there is a possibility that light is emitted from only one of the first layer and the second layer. When the substance having a high light-emitting property contained in the first layer and the substance having a high light-emitting property contained in the second layer are the same, light can be made to be emitted in the vicinity of the center of the light-emitting layer. Accordingly, it is preferred that the substance having a light-emitting property contained in the first layer and the substance having a light-emitting property contained in the second layer be the anthracene derivatives of the present invention. Since the anthracene derivatives of the present invention have high emission efficiency, by application thereof to the structure described in this embodiment mode, a light-emitting element with high emission efficiency and a long life can be obtained.

In the light-emitting element described in this embodiment mode, a light-emitting region is formed in the vicinity of the center of the light-emitting layer, not at the interface between the light-emitting layer and the hole-transporting layer or at the interface between the light-emitting layer and the electron-transporting layer. Accordingly, the light-emitting element is not affected by deterioration caused by the light-emitting region being close to the hole-transporting layer or the electron-transporting layer. Therefore, the light-emitting element with little deterioration and a long life can be obtained. Furthermore, since the light-emitting layer in the light-emitting element of the present invention contains the compound that is stable with respect to repetitive redox reactions, there is little deterioration in the light-emitting layer even if light emission by recombination of holes and electrons are repeated. Therefore, a light-emitting element with a longer life can be obtained.

Since the first organic compound and the second organic compound emit light of similar colors, light with high color purity can be obtained with the light-emitting element described in this embodiment mode even if not only the first organic compound but also the second organic compound emits light. Further, since each of the anthracene derivatives of the present invention is a substance having a high light-emitting element property which emits blue light the element structure described in this embodiment mode is particularly effective for use in a light-emitting element of bluish color and a light-emitting element of blue-greenish color. Blue color is needed for the fabrication of a full-color display, and the amount of deterioration can be reduced by application of the present invention. It is natural that the anthracene derivatives of the present invention may be used for a light-emitting element of green or red color, as well. This embodiment mode can be combined with any other embodiment mode as appropriate.

[Embodiment Mode 7]

In this embodiment mode, a light-emitting element in which a plurality of light-emitting units according to the present invention is stacked (hereinafter, referred to as a stacked type element) is described using FIG. 3. This light-emitting element is a stacked type light-emitting element that has a plurality of light-emitting units between a first electrode and a second electrode. Each light-emitting unit can have a structure similar to that of the layer 102 that contains an organic compound described in Embodiment Mode 2. In other words, the light-emitting element described in Embodiment Mode 2 is a light-emitting element that has one light-emitting unit. In this embodiment mode, a light-emitting element that has a plurality of light-emitting units is described.

Figure 3:
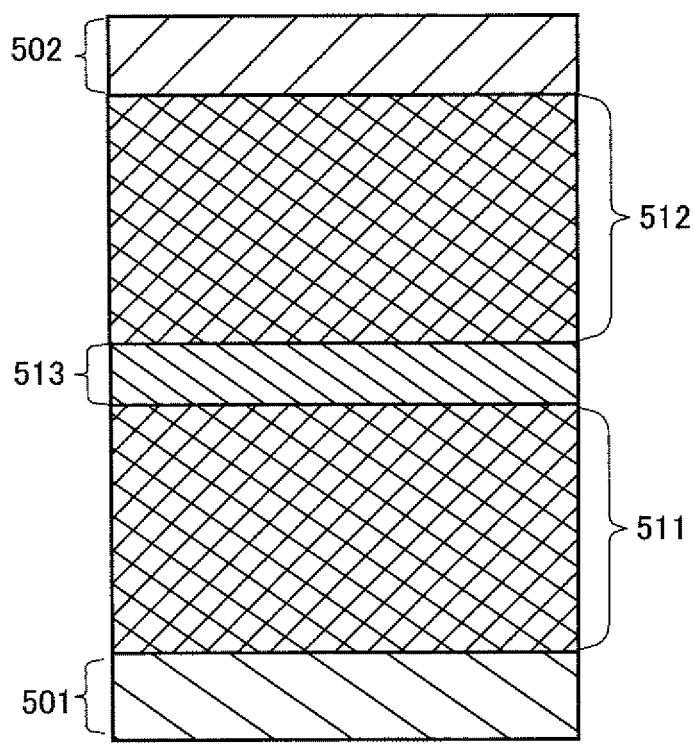
FIG. 3 illustrates a light-emitting element of the present invention.

In FIG. 3, a first light-emitting unit 511 and a second light-emitting unit 512 are stacked between a first electrode 501 and a second electrode 502, and a charge generation layer 513 is provided between the first light-emitting unit 511 and the second light-emitting unit 512. Electrodes similar to those described in Embodiment Mode 2 can be applied for the first electrode 501 and the second electrode 502. The first light-emitting unit 511 and the second light-emitting unit 512 may have structures that are the same or different from each other, and a structure similar to those described in any of Embodiment Modes 2 to 6 can be employed.

The charge generation layer 513 contains a composite material of an organic compound and a metal oxide. The composite material of an organic compound and a metal oxide is described in Embodiment Modes 2 or 5 and contains an organic compound and a metal oxide such as vanadium oxide, molybdenum oxide, or tungsten oxide. As the organic compound, a variety of compounds such as aromatic amine compounds, carbazole derivatives, aromatic hydrocarbons, or compounds with a high molecular weight (such as oligomers, dendrimers, or polymers) can be used. It is to be noted that an organic compound having a hole mobility of greater than or equal to $10^{-6}$ cm$^2$/(V·s) is preferably applied as the organic compound. However, a substance other than these compounds may also be used as long as it is a substance in which the hole-transporting property is higher than the electron-transporting property. Since the composite material of an organic compound and a metal oxide is superior in carrier-injecting property and carrier-transporting property, low-voltage driving and low-current driving can be realized.

It is to be noted that the charge generation layer 513 may be formed by a combination of a composite material of an organic compound and a metal oxide with another material. For example, the charge generation layer 513 may be formed by a combination of a layer containing the composite material of an organic compound and a metal oxide with a layer containing one compound selected from among electron-donating substances and a compound having a high electron-transporting property. Further, the charge generation layer 513 may be formed by a combination of a layer containing the composite material of an organic compound and a metal oxide with a transparent conductive film.

In any case, any structure for the charge generation layer 513 interposed between the first light-emitting unit 511 and the second light-emitting unit 512 is acceptable as long as it is one by which electrons are injected into one light-emitting unit and holes are injected into the other light-emitting unit when a voltage is applied between the first electrode 501 and the second electrode 502. For example, an acceptable structure is one in which, in FIG. 3, the charge generation layer 513 injects electrons into the first light-emitting unit 511 and injects holes into the second light-emitting unit 512 when a voltage is applied so that the potential of the first electrode is higher than that of the second electrode.

In this embodiment mode, the light-emitting element having two light-emitting units is described; however, the present invention can be applied in a similar manner to a light-emitting element in which three or more light-emitting units are stacked. When a plurality of light-emitting units are arranged to be partitioned from each other with a charge generation layer between a pair of electrodes, like the light-emitting element according to this embodiment mode, emission from a region of high luminance can be realized at a low current density, and thus, an element with a long life can be achieved. For example, when the light-emitting element is applied to a lighting device, a drop in voltage due to the resistance of an electrode material can be suppressed, and thus, uniform emission in a large area can be achieved. In other words, a light-emitting device that can be driven at low voltage and has low power consumption can be realized.

When the emission color is different for each light-emitting unit, a desired emission color can be obtained from the whole light-emitting element. For example, when an emission color of the first light-emitting unit and an emission color of the second light-emitting unit are complementary colors, it is possible to obtain a light-emitting element having two light-emitting units, from which white light is emitted from the whole element. It is to be noted that the complementary colors refer to colors that can produce an achromatic color when they are mixed. That is, white light emission can be obtained by mixture of light from substances whose emission colors are complementary colors. Similarly in a light-emitting element having three light-emitting units, for example, white light can be obtained from the whole light-emitting element when emission colors of the first, second, and third light-emitting units are red, green, and blue, respectively.

This embodiment mode can be combined with any other embodiment mode as appropriate.

[Embodiment Mode 8]

In this embodiment mode, a light-emitting device manufactured using any of the anthracene derivatives of the present invention is described.

In this embodiment mode, a light-emitting device manufactured using any of the anthracene derivatives of the present invention is described using FIGS. 4A and 4B. FIG. 4A is a top view of a light-emitting device, and FIG. 4B is a cross-sectional view taken along lines A-A' and B-B' of FIG. 4A. The light-emitting device has a driver circuit portion (a source side driver circuit) 401, a pixel portion 402, and a driver circuit portion (a gate side driver circuit) 403 which are indicated by dotted lines to control the light-emitting device. Reference numerals 404 and 405 denote a sealing substrate and a sealing material, respectively. A portion enclosed by the sealing material 405 corresponds to a space 407.

A lead wiring 408 is a wiring used to transmit signals to be inputted to the source side driver circuit 401 and the gate side driver circuit 403 and receives a video signal, a clock signal, a start signal, a reset signal, and the like from a flexible printed circuit (FPC) 409 which is an external input terminal. It is to be noted that only the FPC is illustrated in this case; however the FPC may be provided with a printed wiring board (PWB). The category of the light-emitting device in this specification includes not only a light-emitting device itself but also a light-emitting device to which an FPC or a PWB is attached with.

Next, a cross-sectional structure is described using FIG. 4B. The driver circuit portion and the pixel portion are formed over an element substrate 410. In this case, one pixel in the pixel portion 402 and the source side driver circuit 401 which is the driver circuit portion are illustrated.

A CMOS circuit, which is a combination of an n-channel TFT 423 and a p-channel TFT 424, is formed as the source side driver circuit 401. Each driver circuit portion may be any of a variety of circuits such as a CMOS circuit, a PMOS circuit, or an NMOS circuit. Although a driver-integration type device, in which a driver circuit is formed over the substrate over which the pixel portion is provided, is described in this embodiment mode, a driver circuit needed not necessarily be formed over the substrate over which the pixel portion is provided but can be formed externally from a substrate.

The pixel portion 402 is formed of a plurality of pixels each of which includes a switching TFT 411, a current control TFT 412, and a first electrode 413 which is electrically connected to a drain of the current control TFT 412. It is to be noted that an insulator 414 is formed to cover end portions of the first electrode 413. In this case, the insulator 414 is formed using a positive photosensitive acrylic resin film.

The insulator 414 is formed so as to have a curved surface having curvature at an upper end portion or a lower end portion thereof in order to make the coverage favorable. For example, in the case of using positive photosensitive acrylic as a material for the insulator 414, it is preferable that the insulator 414 be formed so as to have a curved surface with radius of curvature (0.2 µm to 3 µm) only at the upper end portion thereof. The insulator 414 can be formed using either a negative type which becomes insoluble in an etchant by light irradiation or a positive type which becomes soluble in an etchant by light irradiation.

A layer 416, which contains an organic compound, and a second electrode 417 are formed over the first electrode 413. In this case, it is preferred that the first electrode 413 serving as an anode be formed using a material with a high work function. For example, the first electrode 413 can be formed using a single-layer film of an ITO film, an indium tin oxide film containing silicon, an indium oxide film containing 2 wt % to 20 wt % of zinc oxide, a titanium nitride film, a chromium film, a tungsten film, a Zn film, a Pt film, or the like; a stack of a titanium nitride film and a film containing aluminum as its main component; or a stacked film such as a film having a three-layer structure of a titanium nitride film, a film containing aluminum as its main component, and another titanium nitride film. When the first electrode 413 has a stacked structure, resistance as a wiring is low, a good ohmic contact is formed, and further, the first electrode 413 can be made to function as an anode.

The layer 416 containing an organic compound is formed by any of a variety of methods such as a deposition method using a deposition mask, an inkjet method, and a spin coating method. The layer 416 containing an organic compound contains any of the anthracene derivatives of the present invention which are described in Embodiment Mode 1. Further, another material of the layer 416 containing an organic compound be any of compounds with a low molecular weight or compounds with a high molecular weight (the category of the compounds with a high molecular weight includes oligomers and dendrimers). Further, the material of the layer containing an organic compound may be not only an organic compound but also an inorganic compound.

As a material used for the second electrode 417 which is formed over the layer 416 containing an organic compound and serves as a cathode, it is preferable to use a material with a low work function (e.g., Al, Mg, Li, Ca, or an alloy or compound thereof such as MgAg, Mg—In, Al—Li, LiF, or $CaF_2$). When light generated in the layer 416 containing an organic compound is transmitted through the second electrode 417, the second electrode 417 may be formed of a stack of a metal thin film and a transparent conductive film (e.g., a film of ITO, indium oxide containing 2 wt% to 20 wt % of zinc oxide, indium tin oxide containing silicon or silicon oxide, or zinc oxide (ZnO)).

The sealing substrate 404 is attached using the sealing material 405 to the element substrate 410; thus, a light-emitting element 418 is provided in the space 407 enclosed by the element substrate 410, the sealing substrate 404, and the sealing material 405. It is to be noted that the space 407 is filled with a filler The space 407 is filled with an inert gas (e.g., nitrogen or argon) or the sealing material 405 in some cases.

It is preferable that an epoxy-based resin be used to form the sealing material 405 and that such a material permeate little moisture and oxygen as much as possible. In addition to a glass substrate or a quartz substrate, the sealing substrate 404 can be formed of a plastic substrate made of fiberglass-reinforced plastic (FRP), polyvinyl fluoride (PVF), polyester, acrylic, or the like.

Accordingly, a light-emitting device manufactured using any of the anthracene derivatives of the present invention can be obtained.

Since any of the anthracene derivatives described in Embodiment Mode 1 is used in the light-emitting device of the present invention, a light-emitting device having favorable characteristics can be obtained. Specifically, a light-emitting device that has a long life can be obtained.

Further, since the anthracene derivatives of the present invention have high emission efficiency, a light-emitting device having low power consumption can be provided.

Further, since the light-emitting element in which any of the anthracene derivatives of the present invention is used can emit blue light with high color purity at high efficiency, the anthracene derivatives are suitable for use in full-color displays. Further, since the light-emitting element in which any of the anthracene derivatives of the present invention is used can emit blue light for a long period of time and has low power consumption, the anthracene derivatives are suitable for use in full-color displays.

Figure 5A:
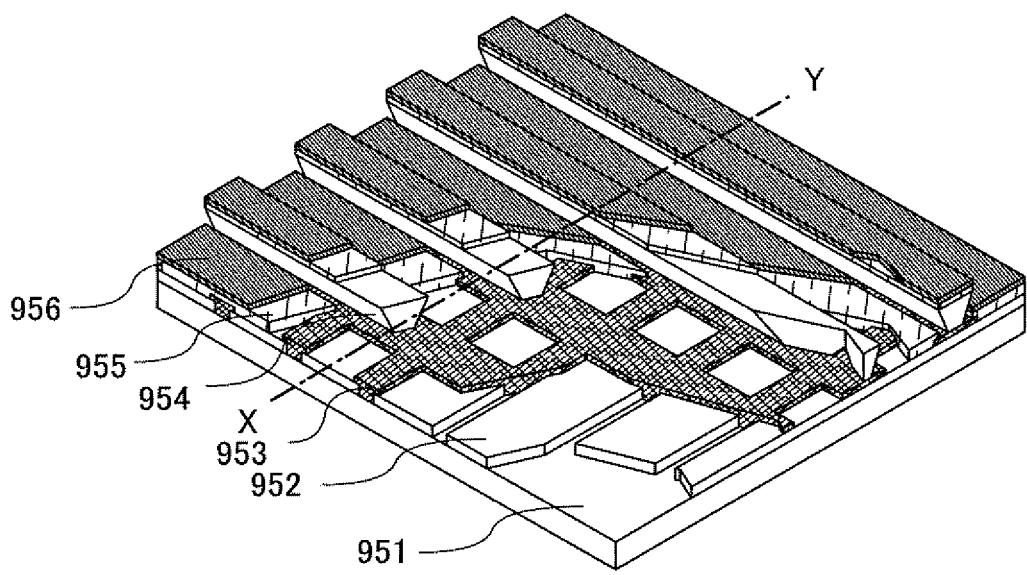
FIGS. 5A and 5B illustrate a light-emitting device of the present invention.
Figure 5B:
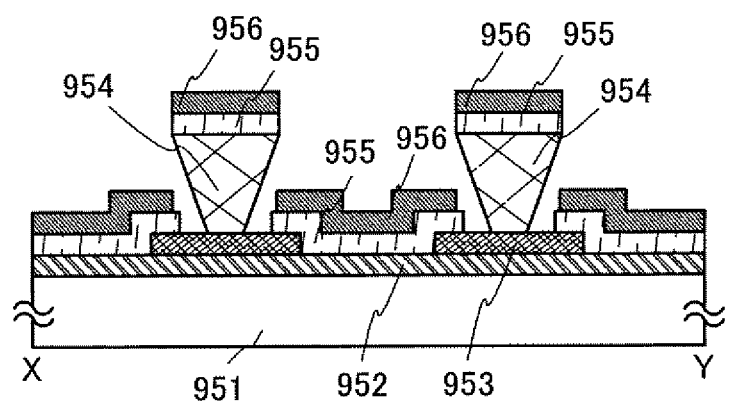

Although as described above, an active matrix light-emitting device in which driving of a light-emitting element is controlled by transistors is described in this embodiment, the light-emitting device may also be a passive matrix light-emitting device. FIGS. 5A and 5B show a passive matrix light-emitting device to which the present invention is applied. FIG. 5A is a perspective view of the light-emitting device, and FIG. 5B is a cross-sectional view taken along a line X-Y of FIG. 5A. In FIGS. 5A and 5B, a layer 955 containing an organic compound is provided between an electrode 952 and an electrode 956 over a substrate 951. End portions of the electrode 952 are covered by an insulating layer 953. Then, a partition layer 954 is provided over the insulating layer 953. A sidewall of the partition layer 954 slopes so that the distance between one sidewall and another sidewall becomes narrower toward the substrate surface. In other words, a cross section taken in the direction of the short side of the partition layer 954 is trapezoidal and the base of the cross-section (a side facing in the same direction as a plane direction of the insulating layer 953 and in contact with the insulating layer 953) is shorter than the upper side thereof (a side facing in the same direction as the plane direction of the insulating layer 953 and not in contact with the insulating layer 953). The partition layer 954 provided in this manner can be used to prevent the light-emitting element from being defective due to static electricity or the like. Even in the case of a passive matrix light-emitting device, when the light-emitting device includes the light-emitting element of the present invention, a light-emitting device with a long life can be obtained, and a light-emitting device having low power consumption can also be obtained.

[Embodiment Mode 9]

In this embodiment mode, electronic devices of the present invention that include the light-emitting device described in Embodiment Mode 8 are described. The electronic devices of the present invention each contain any of the anthracene derivatives described in Embodiment Mode 1 and have a display portion that has a long life. Further, the electronic devices of the present invention each have a display portion in which power consumption is reduced.

Examples of electronic devices that include light-emitting elements fabricated using any of the anthracene derivatives of the present invention include cameras such as video cameras or digital cameras, goggle type displays, navigation systems, audio playback devices (e.g., car audio systems and audio systems), computers, game machines, portable information terminals (e.g., mobile computers, cellular phones, portable game machines, and electronic books), image playback devices in which a recording medium is provided (devices that are capable of playing back recording media such as digital versatile discs (DVDs) and equipped with a display device that can display the image), and the like. Specific examples of these electronic devices are shown in FIGS. 6A to 6D.

Figure 6A:
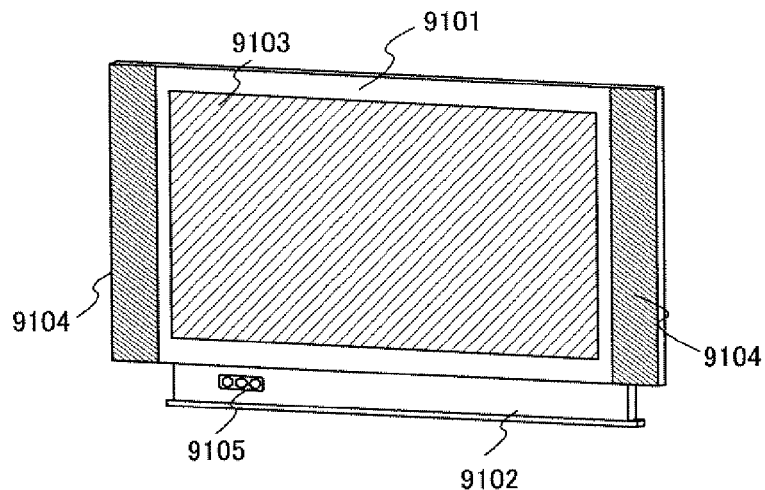
FIGS. 6A to 6D illustrate electronic devices of the present invention.

FIG. 6A shows a television device according to the present invention which includes a housing 9101, a support stand 9102, a display portion 9103, a speaker portion 9104, a video input terminal 9105, and the like. In the television device, the display portion 9103 has light-emitting elements similar to those described in Embodiment Modes 2 to 7 arranged in matrix form. The light-emitting element is characterized by having high emission efficiency and a long life. Since the display portion 9103 formed of the light-emitting elements has similar characteristics, image quality does not deteriorate much and lower power consumption is achieved in the television device. Such characteristics contribute to a significant reduction in size and number of the deterioration compensation function circuits and power supply circuits in the television device, whereby the size and weight of the housing 9101 and support stand 9102 can be reduced. In the television device according to the present invention, lower power consumption, a higher image quality, a smaller size, and a lighter weight are achieved; therefore, products suitable for a residence can be provided. Also, since the anthracene derivatives described in Embodiment Mode 1 can emit blue light with high color purity, full-color display is possible, and a television device having a display portion with a long life can be obtained.

Figure 6B:
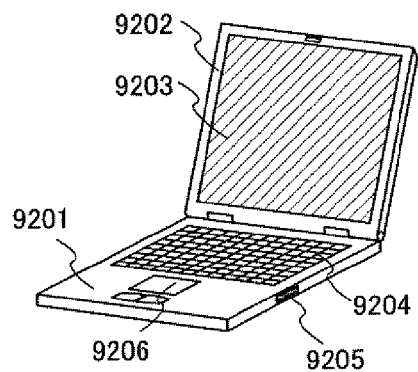

FIG. 6B shows a computer according to the present invention which includes a main body 9201, a housing 9202, a display portion 9203, a keyboard 9204, an external connection port 9205, a pointing device 9206, and the like. In the computer, the display portion 9203 has light-emitting elements similar to those described in Embodiment Modes 2 to 7 arranged in matrix form. The light-emitting element is characterized by having high emission efficiency and a long life. Since the display portion 9203 formed of the light-emitting elements has similar characteristics, image quality does not deteriorate much and lower power consumption is achieved in the computer. Such characteristics contribute to a significant reduction in size and number of the deterioration compensation function circuits and power supply circuits in the computer, whereby the size and weight of the main body 9201 and the housing 9202 can be reduced. In the computer according to the present invention, lower power consumption, a higher image quality, a smaller size, and a lighter weight are achieved; therefore, products suitable for the environment can be supplied. Further, since the anthracene derivatives described in Embodiment Mode 1 can emit blue light with high color purity, full-color display is possible, and a computer having a display portion with a long life can be obtained.

Figure 6C:
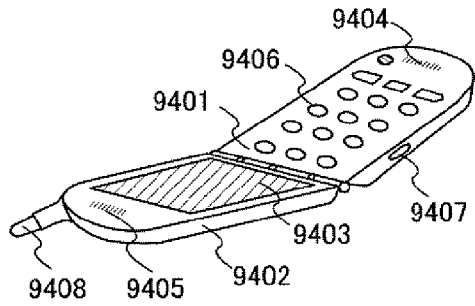

FIG. 6C shows a cellular phone according to the present invention which includes a main body 9401, a housing 9402, a display portion 9403, an audio input portion 9404, an audio output portion 9405, operation keys 9406, an external connection port 9407, an antenna 9408, and the like. In the cellular phone, the display portion 9403 has light-emitting elements similar to those described in Embodiment Modes 2 to 7 arranged in matrix form. The light-emitting element is characterized by high emission efficiency and a long life. Since the display portion 9403 formed of the light-emitting elements has similar characteristics, image quality does not deteriorate much and lower power consumption is achieved in the cellular phone. Such characteristics contribute to a significant reduction in size and number of the deterioration compensation function circuits and power supply circuits in the cellular phone, whereby the size and weight of the main body 9401 and the housing 9402 can be reduced. In the cellular phone according to the present invention, lower power consumption, a higher image quality, a smaller size, and a lighter weight are achieved; therefore, products suitable for portability can be provided. Since the anthracene derivatives described in Embodiment Mode 1 can emit blue light with high color purity, full-color display is possible, and a cellular phone having a display portion with a long life can be obtained.

Figure 6D:
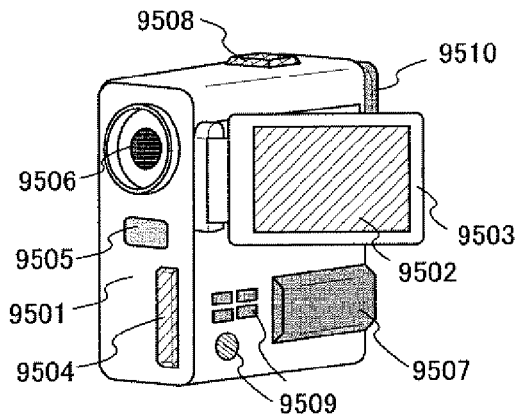

FIG. 6D shows a camera according to the present invention which includes a main body 9501, a display portion 9502, a housing 9503, an external connection port 9504, a remote control receiver 9505, an image receiver 9506, a battery 9507, an audio input portion 9508, operation keys 9509, an eye piece portion 9510, and the like. In the camera, the display portion 9502 has light-emitting elements similar to those described in Embodiment Modes 2 to 7 arranged in matrix form. Some features of the light-emitting element are its high emission efficiency and a long life. Since the display portion 9502 formed of the light-emitting elements has similar characteristics, image quality does not deteriorate much and lower power consumption can be achieved in the camera. Such characteristics contribute to a significant reduction in size and number of the deterioration compensation function circuits and power supply circuits in the camera, whereby the size and weight of the main body 9501 can be reduced. In the camera according to the present invention, lower power consumption, a higher image quality, a smaller size, and a lighter weight are achieved; therefore, products suitable for being carried can be provided. Since the anthracene derivatives described in Embodiment Mode 1 can emit blue light with high color purity, full-color display is possible, and a camera having a display portion with a long life can be obtained.

As described above, the applicable range of the light-emitting device of the present invention is extremely wide so that this light-emitting device can be applied to electronic devices of a variety of fields. By use of the anthracene derivatives of the present invention, an electronic device that has a display portion with a long life can be obtained. Furthermore, by use of the anthracene derivatives of the present invention, an electronic device that has a display portion in which power consumption is reduced can be obtained.

Such a light-emitting device of the present invention can also be used as a lighting device. One mode in which the light-emitting device of the present invention is used as a lighting device is described using FIG. 7.

Figure 7:
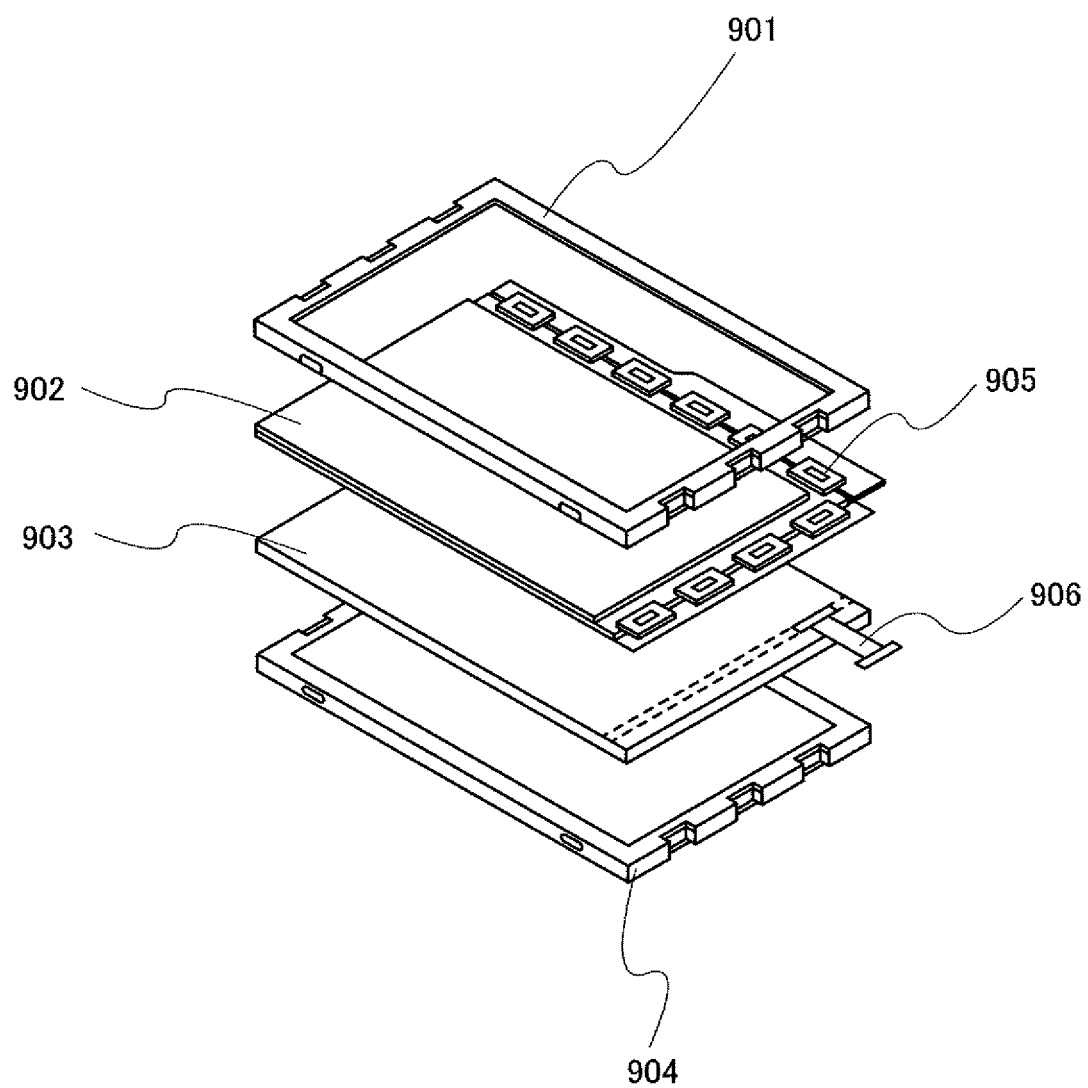
FIG. 7 illustrates a lighting device of the present invention.

FIG. 7 shows an example of a liquid crystal display in which the light-emitting device of the present invention is used as a backlight. The liquid crystal display device shown in FIG. 7 includes a housing 901, a liquid crystal layer 902, a backlight 903, and a housing 904. The liquid crystal layer 902 is connected to a driver IC 905. The light-emitting device of the present invention is used as the backlight 903, and current is supplied through a terminal 906.

By use of the light-emitting device of the present invention as the backlight of the liquid crystal display device, a backlight with high emission efficiency and lower power consumption and can be obtained. Since the light-emitting device of the present invention is a lighting device with plane light emission and can have a larger area, the backlight can have a larger area, and a liquid crystal display device can also have a larger area. Furthermore, since the light-emitting device of the present invention is thin and has low power consumption, a thinner shape and lower power consumption can also be achieved in a display device. Since the light-emitting device of the present invention has a long life, a liquid crystal display device in which the light-emitting device of the present invention is used can also have a long life.

Figure 8:
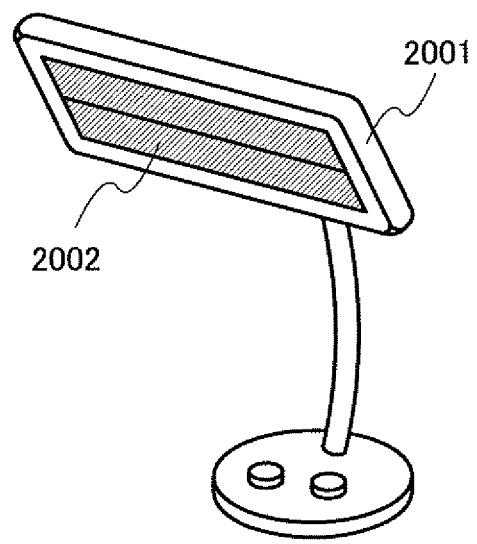
FIG. 8 illustrates a lighting device of the present invention.

FIG. 8 shows an example in which the light-emitting device to which the present invention is applied is used as a table lamp that is a lighting device. The table lamp shown in FIG. 8 has a housing 2001 and a light source 2002. The light-emitting device of the present invention is used as the light source 2002. Since the light-emitting device of the present invention has high emission efficiency and a long life, the table lamp also has high emission efficiency and a long life.

Figure 9:
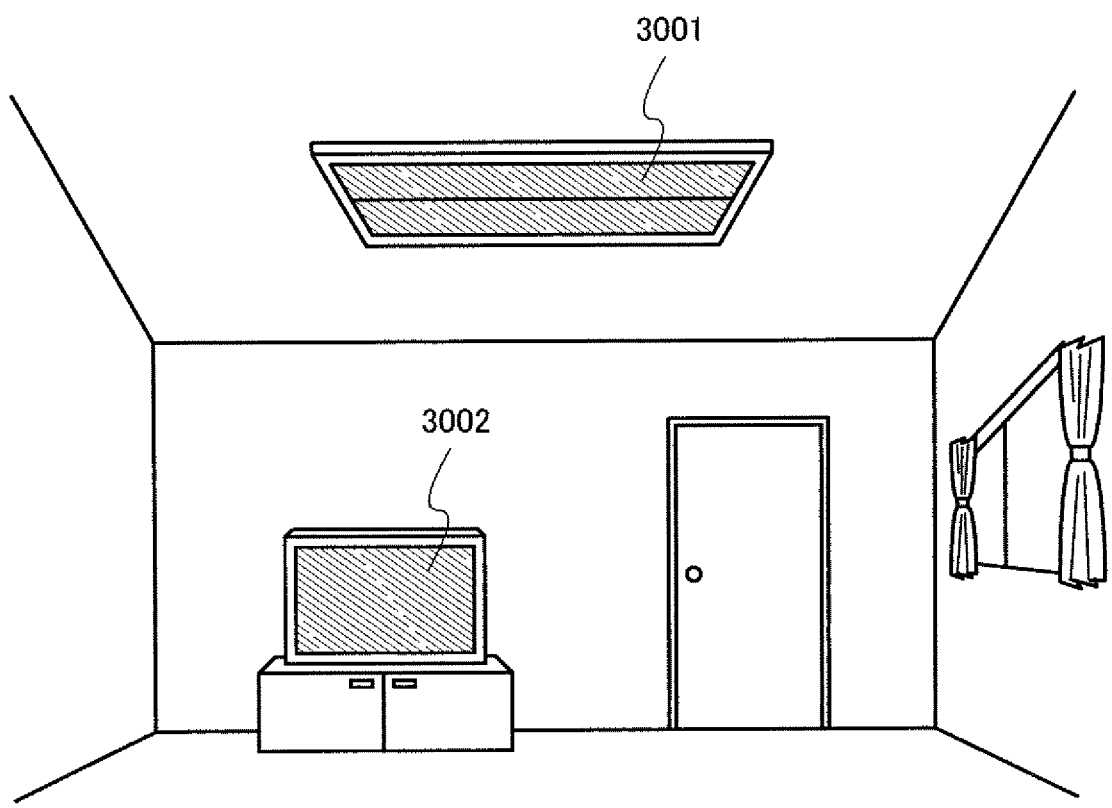
FIG. 9 illustrates a lighting device of the present invention.

FIG. 9 shows an example in which a light-emitting device to which the present invention is applied is used as an indoor lighting device 3001. Since the light-emitting device of the present invention can also have a larger area, the light-emitting device of the present invention can be used as a lighting device having a large emission area. Further, since the light-emitting device of the present invention is thin and has low power consumption, the light-emitting device of the present invention can be used as a lighting device with a thinner shape and lower power consumption. A television device 3002 according to the present invention as described in FIG. 6A is placed in a room in which a light-emitting device to which the present invention is applied is used as the indoor lighting device 3001, and public broadcasting and movies can be enjoyed. In such a case, since power consumption is low in both devices, a powerful image can be watched in a bright room without any concern about charges for electricity.

[Example 1]

In this synthesis example, a synthesis method of an anthracene derivative 4-(10-phenyl-9-anthryl)-4'-(9-phenyl-9H-carbazol-3-yl)triphenylamine (PCBAPA) of the present invention represented by a structural formula (100) is described in specific terms.

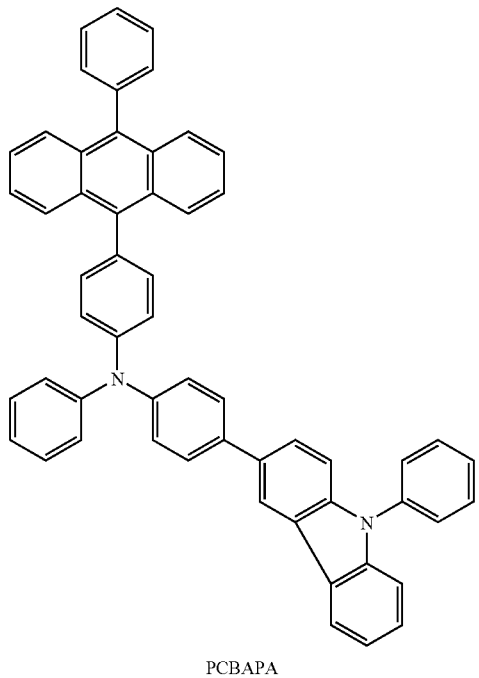

PCBAPA

Step 1: Synthesis of
9-phenyl-9H-carbazole-3-boronic acid

Into a 500 mL three-neck flask were put 10 g (31 mmol) of 3-bromo-9-phenyl-9H-carbazole. The air in the flask was replaced with nitrogen. 150 mL of tetrahydrofuran (THF) were put into the flask, and 3-bromo-9-phenyl-9H-carbazole was dissolved therein. This solution was cooled to −80° C. Into this solution were dripped 20 mL (32 mmol) of n-butyl-lithium (a 1.58 mol/L hexane solution) with the use of a syringe. After the dripping was completed, this solution was stirred at the same temperature for 1 hour. After the stirring, 3.8 mL (34 mmol) of trimethyl borate were added to the solution, and the solution was stirred for about 15 hours while the temperature of the solution was being brought back to room temperature. Thereafter, about 150 mL (1.0 mol/L) of dilute hydrochloric acid were added to the solution, and then the solution was stirred for 1 hour. After the stirring, an aqueous layer of the mixture was extracted with ethyl acetate. The extract was combined with an organic layer and then washed with a saturated sodium hydrogen carbonate solution. The organic layer was dried with magnesium sulfate. After the drying, the mixture was subjected to gravity filtration. The obtained filtrate was condensed to give an oily light brown substance. The obtained oily substance was dried under reduced pressure to give 7.5 g of a light brown solid, which was the object of the synthesis, at a yield of 86%. A synthesis scheme of Step 1 is shown in (b-1) given below.

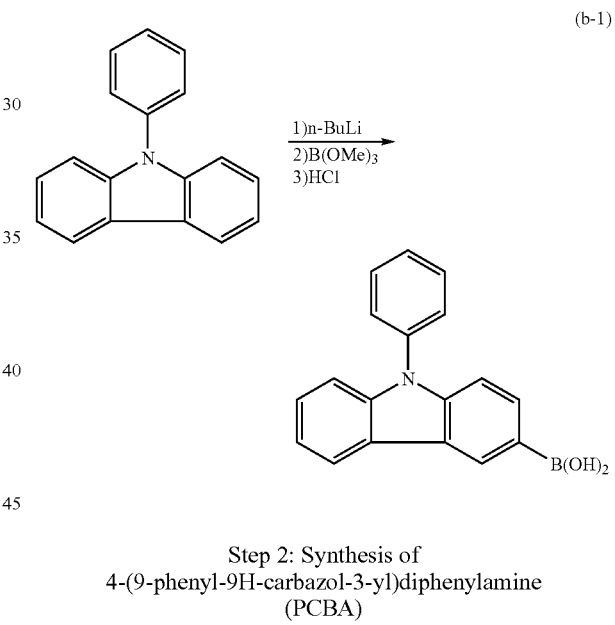

Step 2: Synthesis of
4-(9-phenyl-9H-carbazol-3-yl)diphenylamine
(PCBA)

Into a 500 mL three-neck flask were put 6.5 g (26 mmol) of 4-bromo-diphenylamine, 7.5 g (26 mmol) of 9-phenyl-9H-carbazole-3-boronic acid, and 400 mg (1.3 mmol) of tri(o-tolyl)phosphine. The air in the flask was replaced with nitrogen. To the mixture were added 100 mL of toluene, 50 mL of ethanol, and 14 mL (0.2 mol/L) of an aqueous solution of potassium carbonate. Under reduced pressure, this mixture was degassed while being stirred. After the degassing, 67 mg (30 mmol) of palladium(II) acetate were added to the mixture. This mixture was refluxed at 100° C. for 10 hours. After the reflux, an aqueous layer of the mixture was extracted with toluene, and the extract was combined with an organic layer and then washed with a saturated saline solution. The organic layer was dried with magnesium sulfate. After the drying, this mixture was subjected to gravity filtration. The obtained filtrate was condensed to give an oily light brown substance. This oily substance was purified by silica gel column chromatography (a developing solvent was a mixed solvent of hexane:toluene=4:6). A white solid obtained after the purification was recrystallized with dichloromethane/hexane to give 4.9 g of a white solid, which was the object of the synthesis, at a yield of 45%. A synthesis scheme of Step 2 is shown in (b-2) given below.

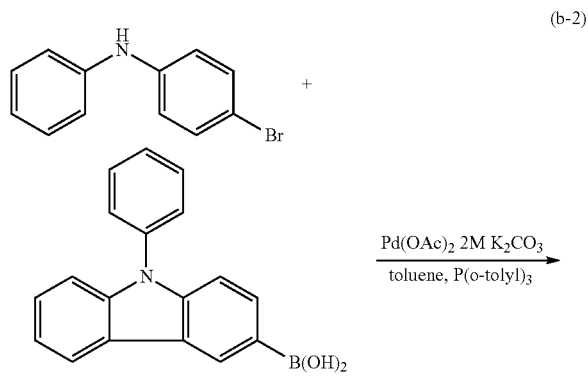

(b-2)

Figure 10A:
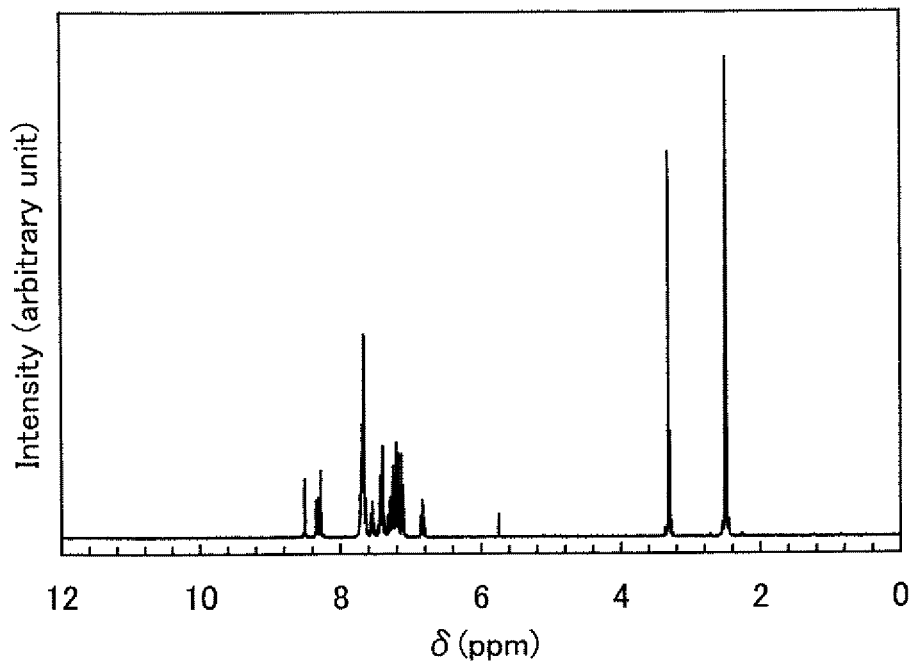
FIGS. 10A and 10B are $^1$H-NMR charts of 4-(9-phenyl-9H-carbazol-3-yl)diphenylamine (abbreviated to PCBA).
Figure 10B:
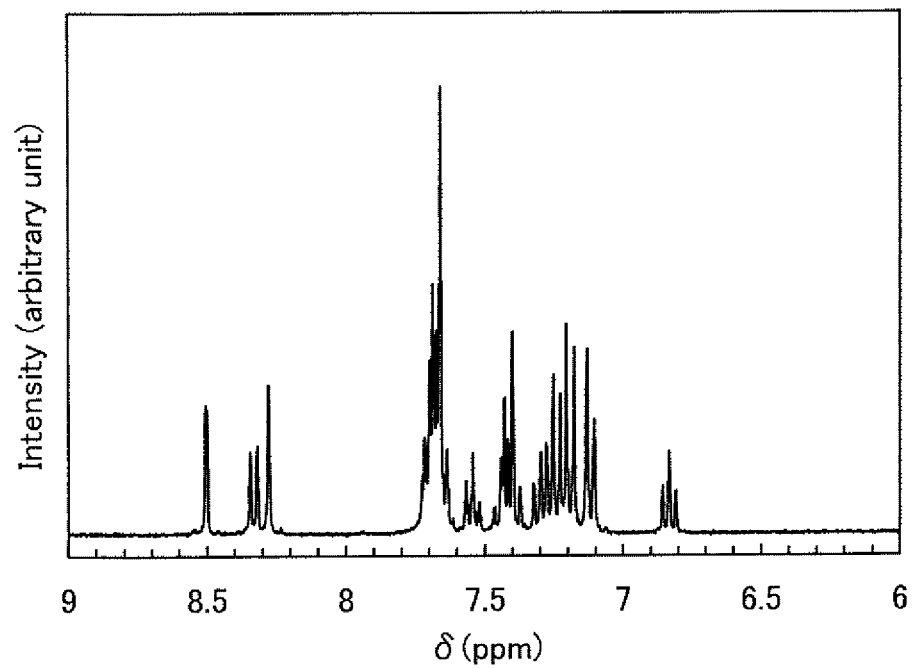

The solid obtained in the above Step 2 was analyzed by nuclear magnetic resonance measurements ($^1$H NMR). The measurement results are described below, and the $^1$H NMR chart is shown in FIGS. 10A and 10B. It is to be noted that FIG. 10B is a chart showing an enlarged view of the range of 6.0 ppm to 9.0 ppm in FIG. 10A. From the measurement results, it can be seen that the organic compound PCBA of the present invention which is a source material used for the synthesis of the anthracene derivative of the present invention represented by the above structural formula (100) was obtained.

$^1$H NMR (DMSO-d$_6$, 300 MHz): δ=6.81-6.86 (m, 1H), 7.12 (dd, J$_1$=0.9 Hz, J$_2$=8.7 Hz, 2H), 7.19 (d, J=8.7 Hz, 2H), 7.23-7.32 (m, 3H), 7.37-7.47 (m, 3H), 7.51-7.57 (m, 1H), 7.61-7.73 (m, 7H) 8.28 (s, 1H), 8.33 (d, J=7.2 Hz, 1H), 8.50 (d, J=1.5 Hz, 1H)

Step 3: Synthesis of PCBAPA

Into a 300 mL three-neck flask were put 7.8 g (12 mmol) of 9-(4-bromophenyl)-10-phenylanthracene, 4.8 g (12 mmol) of PCBA, and 5.2 g (52 mmol) of sodium tert-butoxide. The air in the flask was replaced with nitrogen. To the mixture were added 60 mL of toluene and 0.30 mL of tri(tert-butyl)phosphine (a 10 wt % hexane solution). Under reduced pressure, this mixture was degassed while being stirred. After the degassing, 136 mg (0.24 mmol) of bis(dibenzylideneacetone) palladium(0) were added to the mixture. This mixture was stirred at 100° C. for 3 hours. After the stirring, about 50 mL of toluene were added to this mixture. The mixture was subjected to suction filtration through celite (produced by Wako Pure Chemical Industries, Ltd., Catalog No. 531-16855), alumina, and Florisil (produced by Wako Pure Chemical Industries, Ltd., Catalog No. 540-00135). The obtained filtrate was condensed to give a yellow solid. This solid was recrystallized with toluene/hexane to give 6.6 g of a light yellow powdered solid PCBAPA, which was the object of the synthesis, at a yield of 75%. Then, 3.0 g of the obtained light yellow powdered solid were purified by train sublimation. For sublimation purification conditions, PCBAPA was heated at 350° C. under a pressure of 8.7 Pa with a flow rate of argon gas of 3.0 mL/min. After the sublimation purification, 2.7 g of a light yellow solid PCBAPA was obtained at a yield of 90%. A synthesis scheme of Step 3 is shown in (b-3) given below.

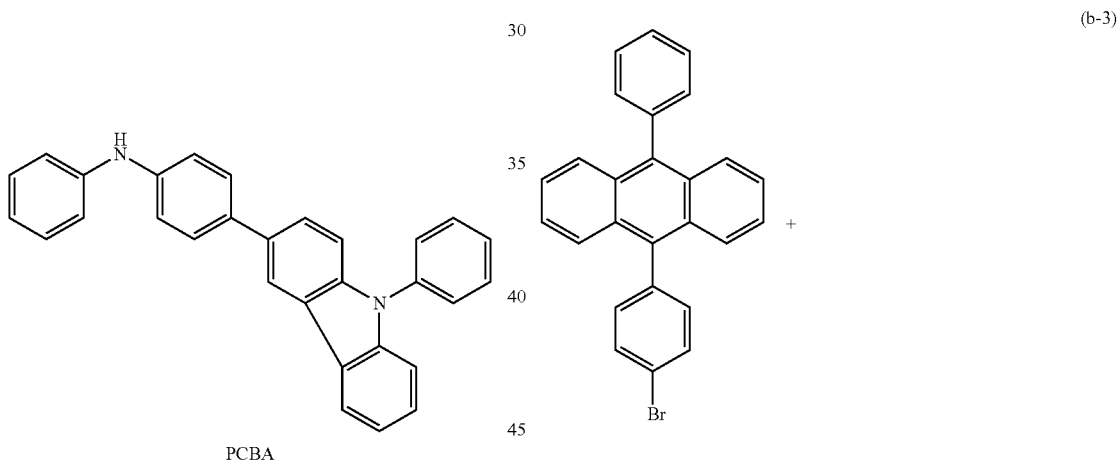

(b-3)

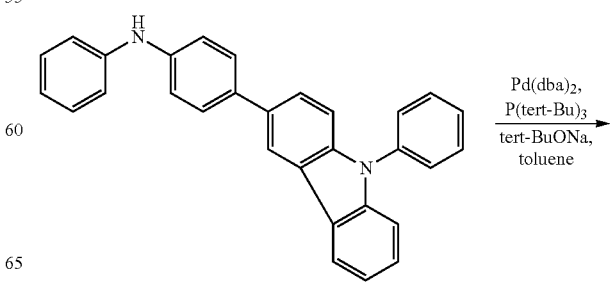

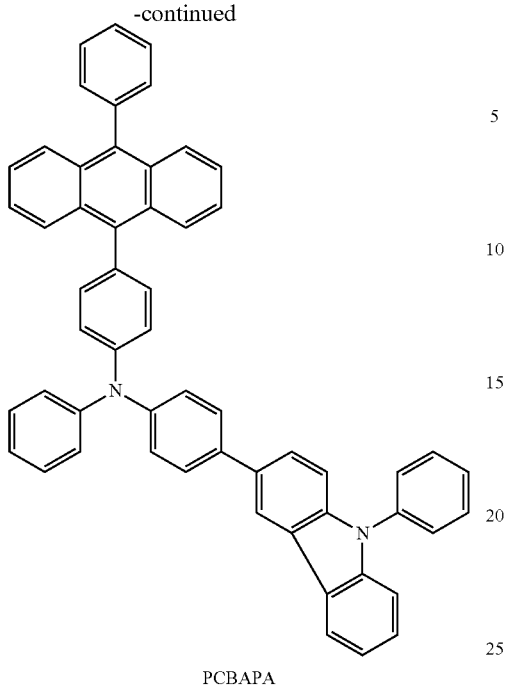

PCBAPA

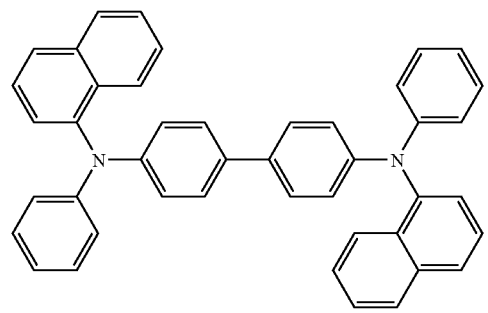

NPB

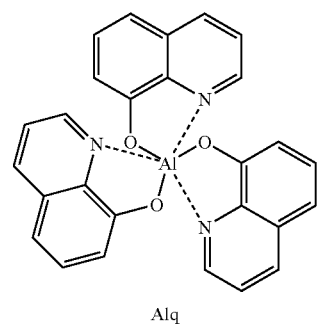

Alq

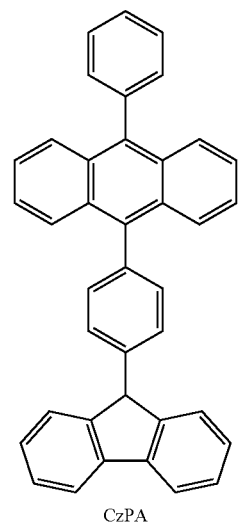 [SMILES: c1ccc(-c2c3ccccc3c(-c3ccc(C4c5ccccc5-c5ccccc54)cc3)c3ccccc23)cc1]

CzPA

Figure 11A:
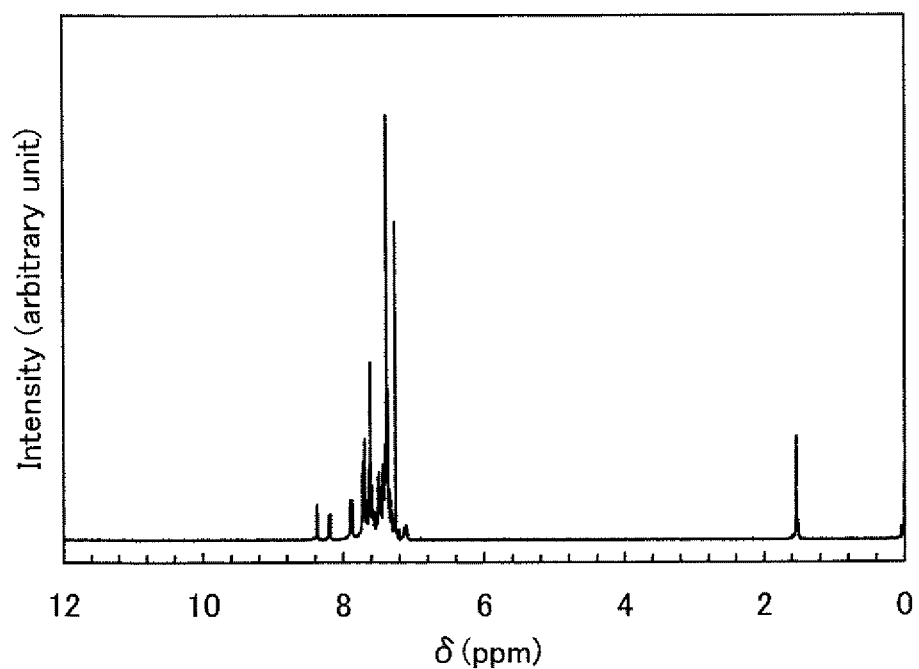
FIGS. 11A and 11B are $^1$H-NMR charts of 4-(10-phenyl-9-anthryl)-4'-(9-phenyl-9H-carbazol-3-yl)triphenylamine (abbreviated to PCBAPA).
Figure 11B:
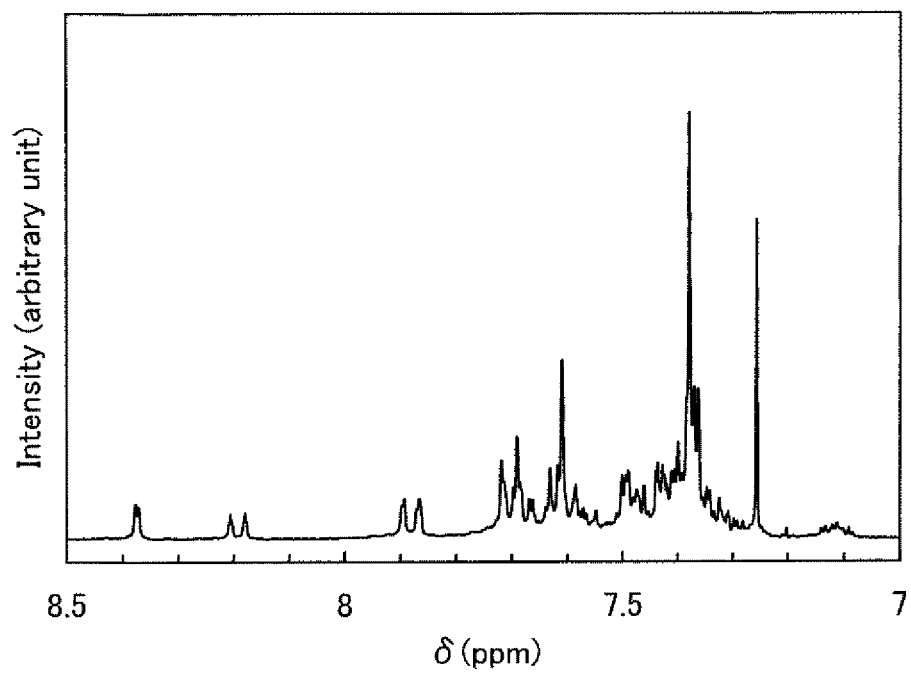

The solid obtained in the above Step 3 was analyzed by $^1$H NMR. The measurement results are described below, and the $^1$H NMR chart is shown in FIGS. 11A and 11B. It is to be noted that FIG. 11B is a chart showing an enlarged view of the range of 7.0 to 8.5 ppm in FIG. 11A. From the measurement results, it can be seen that the anthracene derivative PCBAPA of the present invention represented by the above structural formula (100) was obtained.

$^1$H NMR (CDCl$_3$, 300 MHz): δ=7.09-7.14 (m, 1H), 7.28-7.72 (m, 33H), 7.88 (d, J=8.4 Hz, 2H), 8.19 (d, J=7.2 Hz, 1H), 8.37 (d, J=1.5 Hz, 1H)

Figure 12:
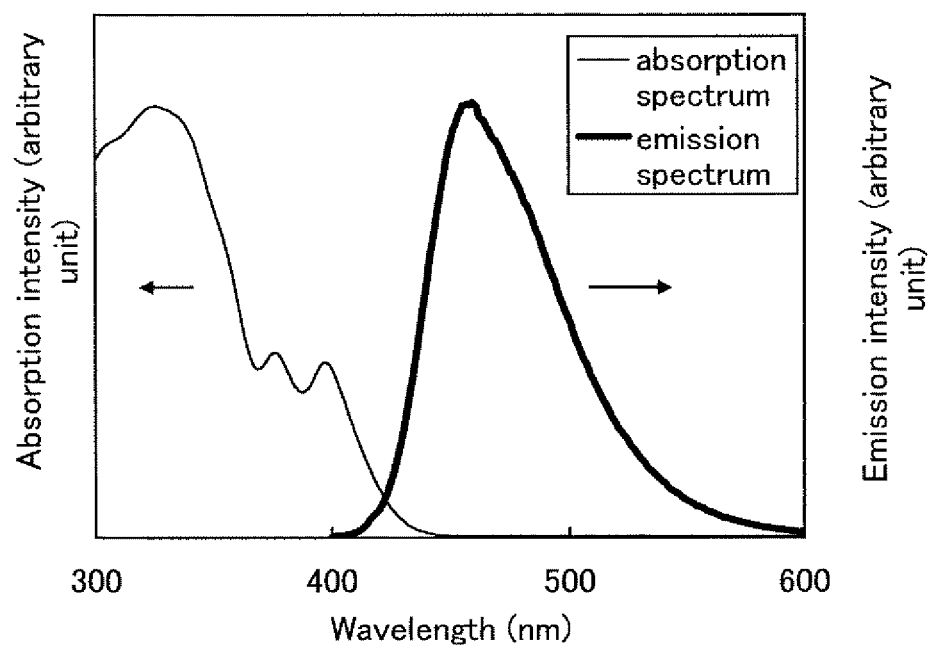
FIG. 12 illustrates an absorption spectrum and an emission spectrum of a toluene solution of 4-(10-phenyl-9-anthryl)-4'-(9-phenyl-9H-carbazol-3-yl)triphenylamine (PCBAPA).
Figure 13:
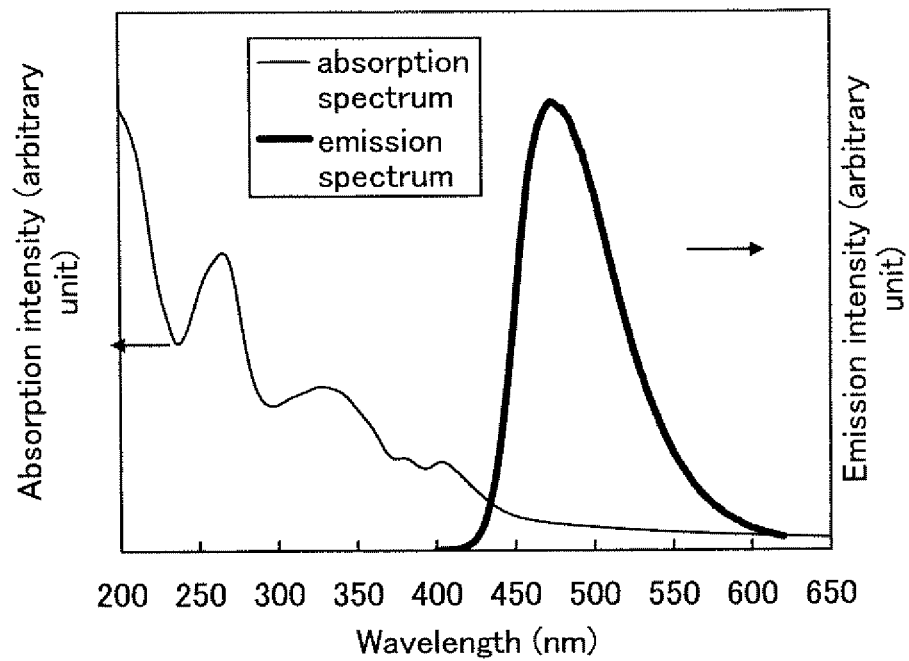
FIG. 13 illustrates an absorption spectrum and an emission spectrum of a thin film of 4-(10-phenyl-9-anthryl)-4'-(9-phenyl-9H-carbazol-3-yl)triphenylamine (PCBAPA).

Next, an absorption spectrum of PCBAPA was measured using an ultraviolet-visible spectrophotometer (V-550,manufactured by JASCO Corporation) at room temperature with the use of a toluene solution. Further, an emission spectrum of PCBAPA was measured using a fluorescence spectrophotometer (FS920,manufactured by Hamamatsu Photonics Corporation) at room temperature with the use of a toluene solution. The measurement results are shown in FIG. 12. Further, PCBAPA was deposited by a deposition method, and a thin film of PCBAPA was measured in a similar manner. The measurement results are shown in FIG. 13. In each of FIG. 12 and FIG. 13, the horizontal axis indicates the wavelength (nm), and the vertical axis indicates the absorption intensity (arbitrary unit) and the emission intensity (arbitrary unit).

From FIG. 12 and FIG. 13, it can be seen that the toluene solution of PCBAPA has an emission peak at 459 nm, and the thin film thereof has an emission peak at 473 nm. Thus, it is found that PCBAPA emits blue light with high color purity.

[Example 2]

Figure 14:
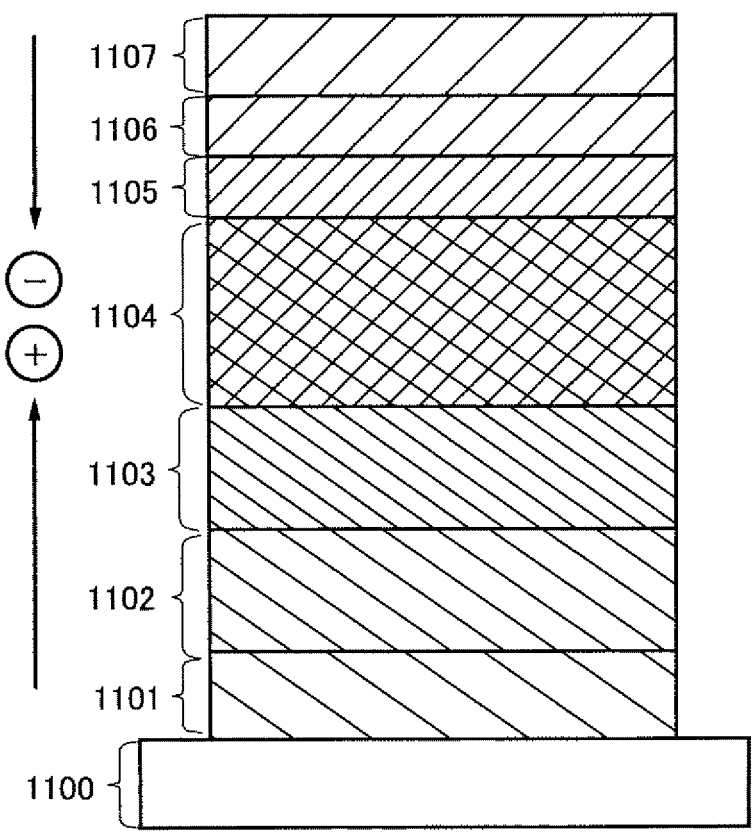
FIG. 14 illustrates a light-emitting element of Example 2.
Figure 15:
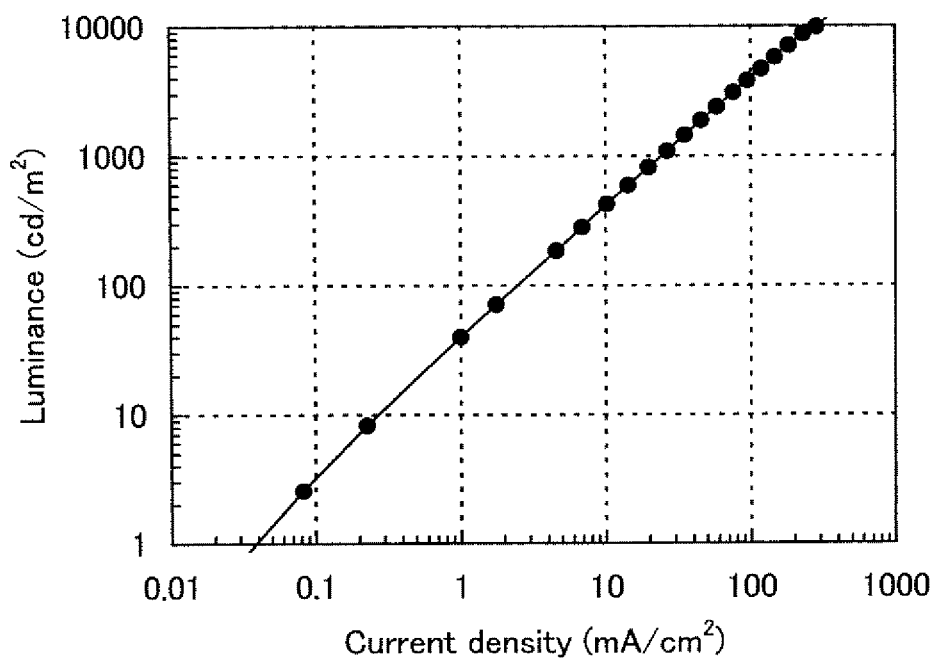
FIG. 15 illustrates current density-luminance characteristics of a light-emitting element fabricated in Example 2.
Figure 16:
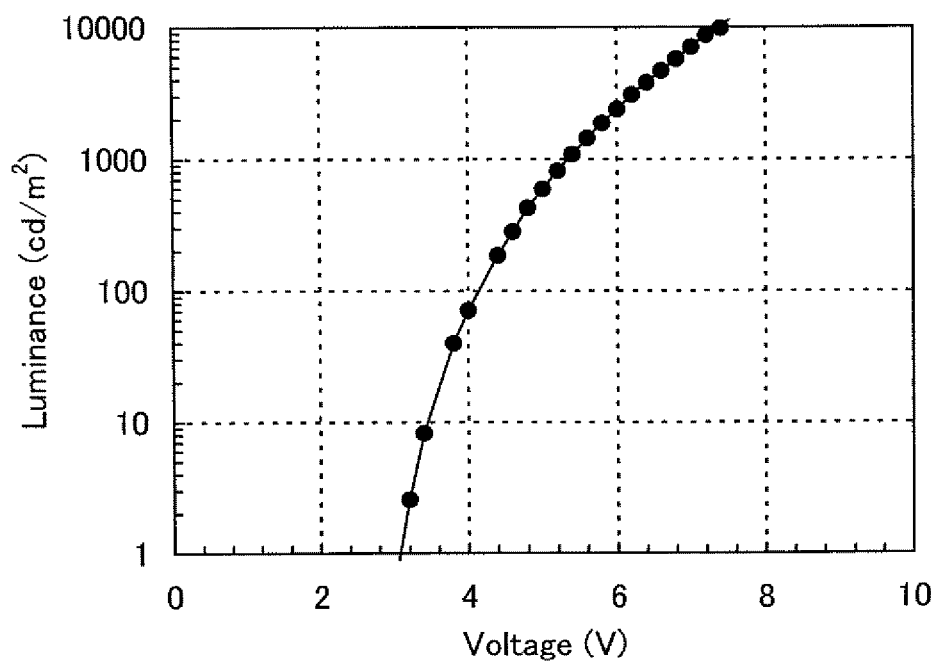
FIG. 16 illustrates voltage-luminance characteristics of a light-emitting element fabricated in Example 2.
Figure 17:
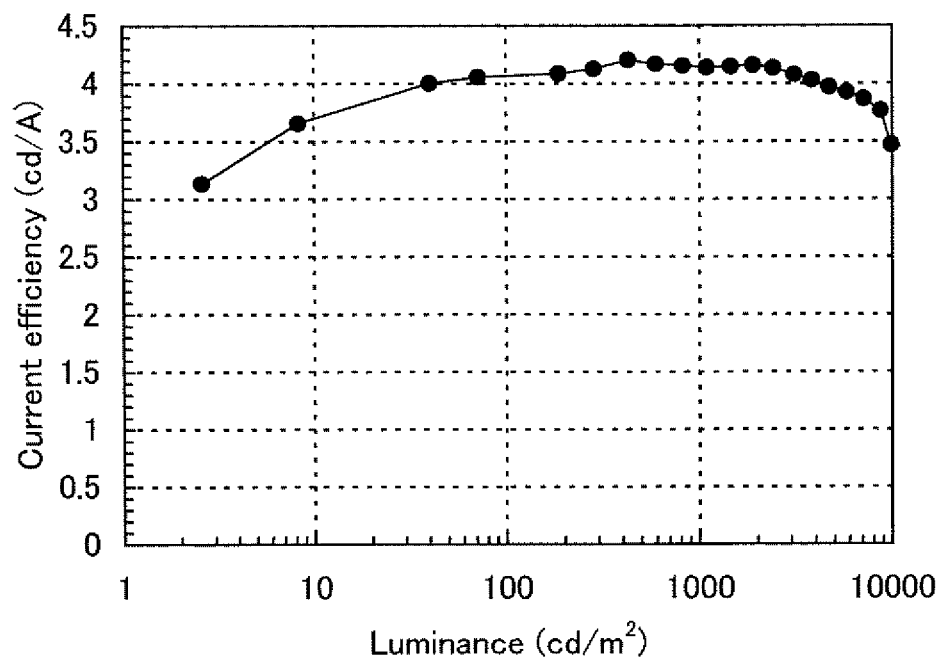
FIG. 17 illustrates luminance-current efficiency characteristics of a light-emitting element fabricated in Example 2.
Figure 18:
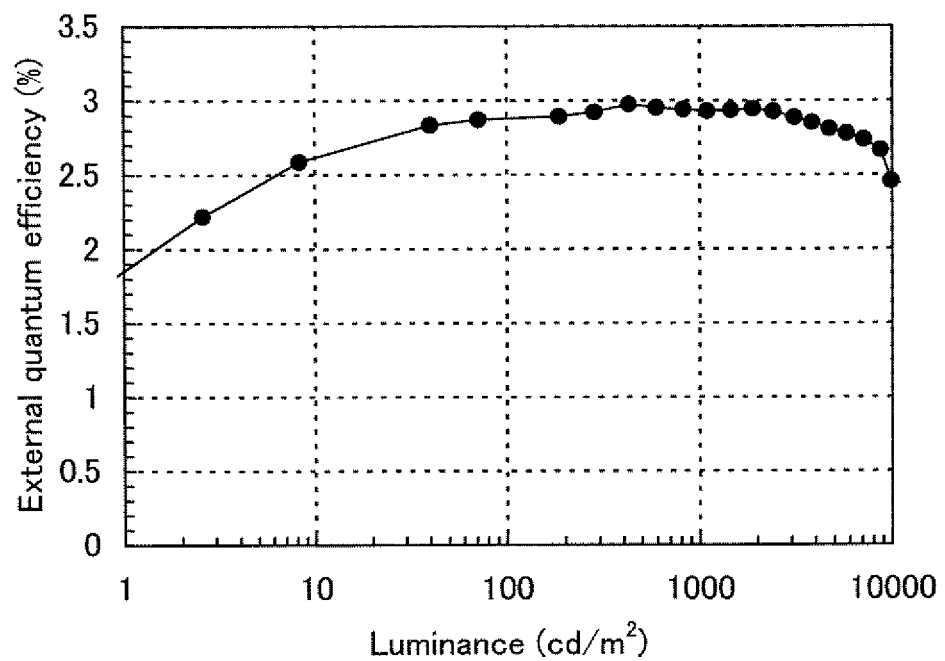
FIG. 18 illustrates luminance-external quantum efficiency characteristics of a light-emitting element fabricated in Example 2.

In this example, a light-emitting element of the present invention is described using FIG. 14. Chemical formulae of materials used in this example are shown below.

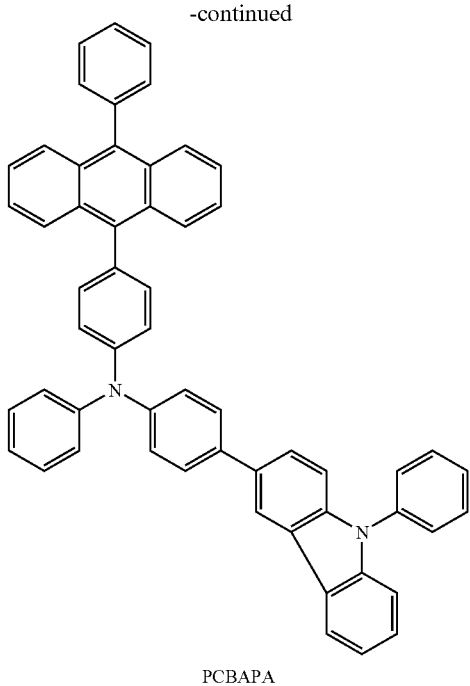

PCBAPA (Light-Emitting Element 1)

First, indium tin oxide containing silicon oxide was deposited over a glass substrate 1100 by a sputtering method, whereby a first electrode 1101 was formed. It is to be noted that the film thickness of the first electrode was set to be 110 nm and that the area of the electrode was set to be 2 mm×2 mm.

Next, the substrate over which the first electrode was formed was fixed to a substrate holder provided in a vacuum deposition apparatus so that a surface on which the first electrode was formed faced downward. After the pressure of the vacuum deposition apparatus was reduced to about $10^{-4}$ Pa, a layer 1102 containing a composite material of an organic compound and an inorganic compound was formed over the first electrode 1101 by co-deposition of NPB and molybdenum(VI) oxide. The film thickness of the layer 1102 was set to be 50 nm, and the weight ratio of NPB and molybdenum (VI) oxide was adjusted so as to be 4:1(=NPB:molybdenum oxide). It is to be noted that the co-deposition method is a deposition method in which deposition is performed from a plurality of evaporation sources at the same time in one treatment chamber.

Next, NPB was deposited to a thickness of 10 nm over the layer 1102 containing a composite material by a deposition method using resistive heating, whereby a hole-transporting layer 1103 was formed.

Further, by co-deposition of 9-[4-(10-phenyl-9-anthryl)phenyl]-9H-carbazole (CzPA) and PCBAPA, a light-emitting layer 1104 was formed over the hole-transporting layer 1103 to a thickness of 30 nm. The weight ratio of CzPA and PCBAPA was adjusted so as to be 1:0.10(=CzPA:PCBAPA).

Thereafter, tris(8-quinolinolato)aluminum (Alq) was deposited to a thickness of 10 nm over the light-emitting layer 1104 by a deposition method using resistive heating, whereby an electron-transporting layer 1105 was formed.

Further, by co-deposition of tris(8-quinolinolato)aluminum (Alq) and lithium, an electron-injecting layer 1106 was formed to a thickness of 20 nm over the electron-transporting layer 1105. The weight ratio of Alq and lithium was adjusted so as to be 1:0.01(=Alq:lithium).

Lastly, aluminum was deposited to a thickness of 200 nm over the electron-injecting layer 1106 by a deposition method using resistive heating, whereby a second electrode 1107 was formed. Accordingly, a light-emitting element 1 was fabricated.

Figure 19:
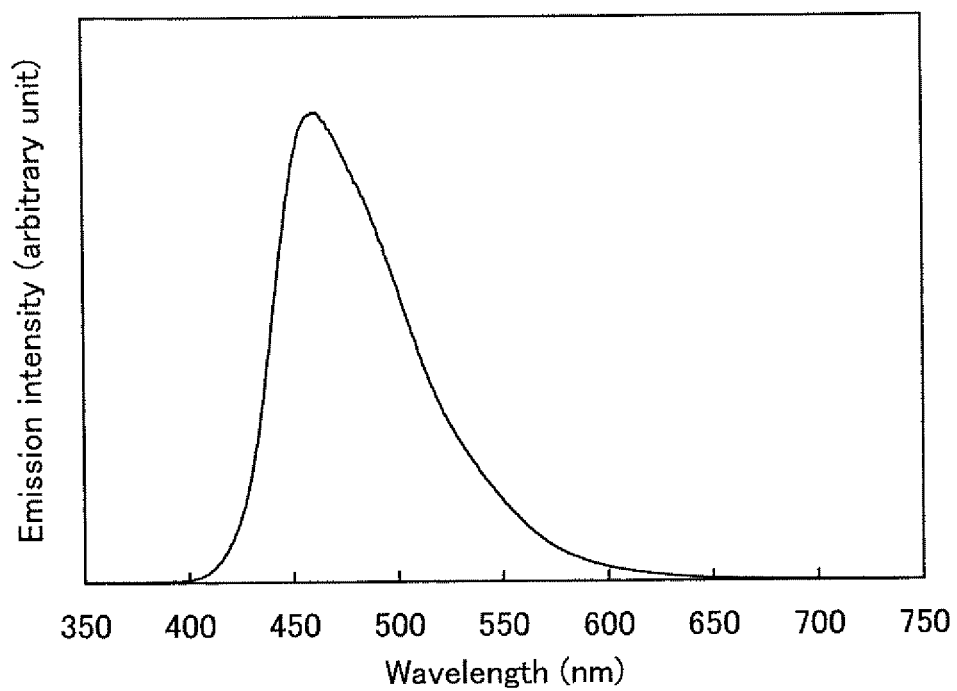
FIG. 19 illustrates an emission spectrum of a light-emitting element fabricated in Example 2.

Current density-luminance characteristics, voltage-luminance characteristics, luminance-current efficiency characteristics, and luminance-external quantum efficiency of the light-emitting element 1 are shown in FIG. 15, FIG. 16, FIG. 17, and FIG. 18, respectively. Also, the emission spectrum measured at a current of 1 mA is shown in FIG. 19. From FIG. 19, it can be seen that light emitted from the light-emitting element was from PCBAPA. A CIE chromaticity coordinates of the light-emitting element 1 at luminance of 820 cd/n² were (x, y)=(0.16, 0.19), which are indicative of blue light with high color purity. As can be seen from FIG. 18, the external quantum efficiency of the light-emitting element 1 measured at luminance of 820 cd/m² was 2.9%, which is indicative of high external quantum efficiency. Thus, the light-emitting element 1 has high emission efficiency. From FIG. 17, it can be seen that the current efficiency of the light-emitting element 1 measured at luminance of 820 cd/m² was 4.2 cd/A, which is indicative of high luminous efficiency. From FIG. 16, the driving voltage of the light-emitting element 1 measured at luminance of 820 cd/m² was 5.2 V, and a voltage needed to obtain a given luminance is low. Thus, it is found that power consumption for the light-emitting element 1 is low.

Figure 26:
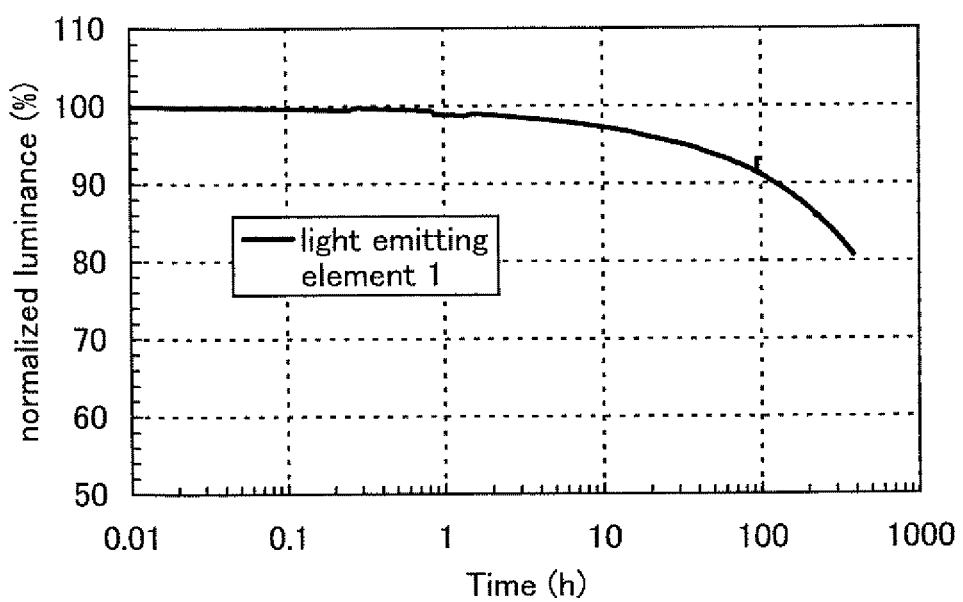
FIG. 26 illustrates a result of a continuous lighting test of a light-emitting element fabricated in Example 2.

In addition, when the light-emitting element 1 of this example was driven under conditions of an initial luminance set to 1000 cd/m2 and a constant instant current density, luminance after 380 hours was retained at 81% of the initial luminance. The results are shown in FIG. 26. In FIG. 26, the horizontal axis indicates time (h), and the vertical axis indicates normalized luminance where the initial luminance was 100%. Consequently, it is found that a light-emitting element with little deterioration and a long life can be obtained by application of the present invention.

[Example 3]

Figure 20:
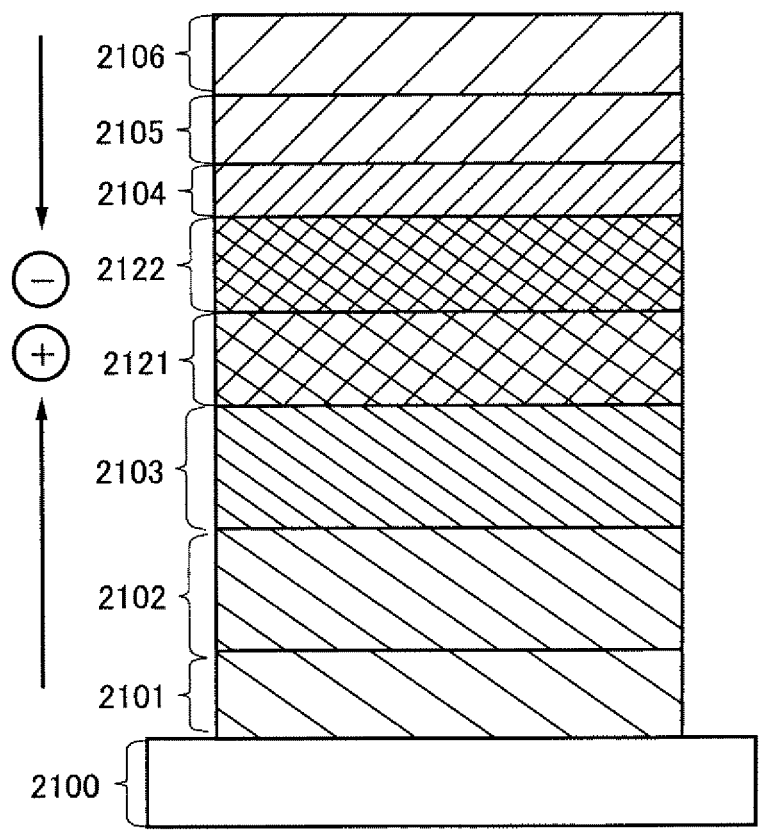
FIG. 20 illustrates a light-emitting element of Example 3.
Figure 21:
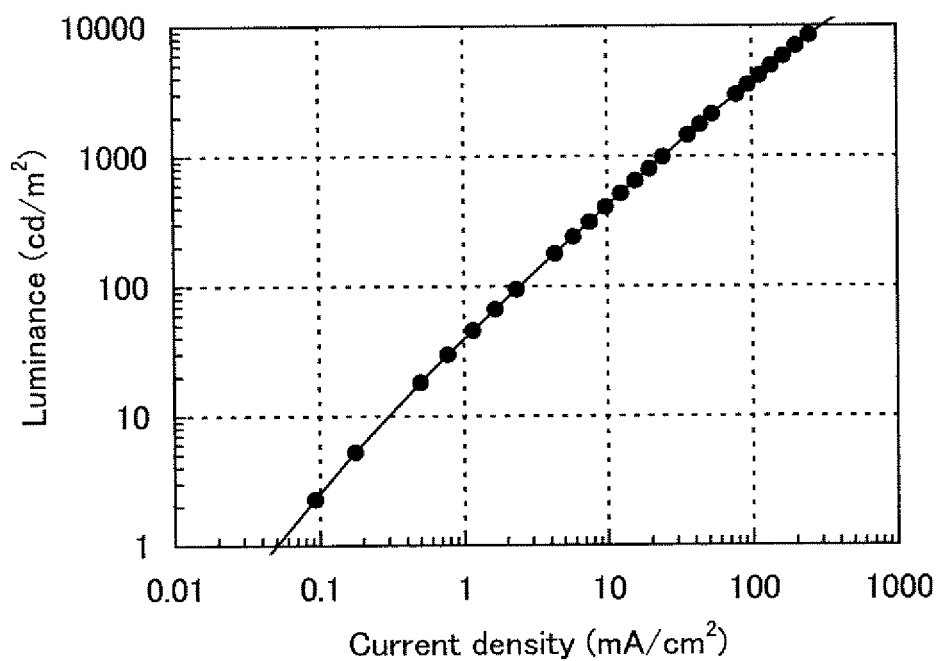
FIG. 21 illustrates current density-luminance characteristics of a light-emitting element fabricated in Example 3.
Figure 22:
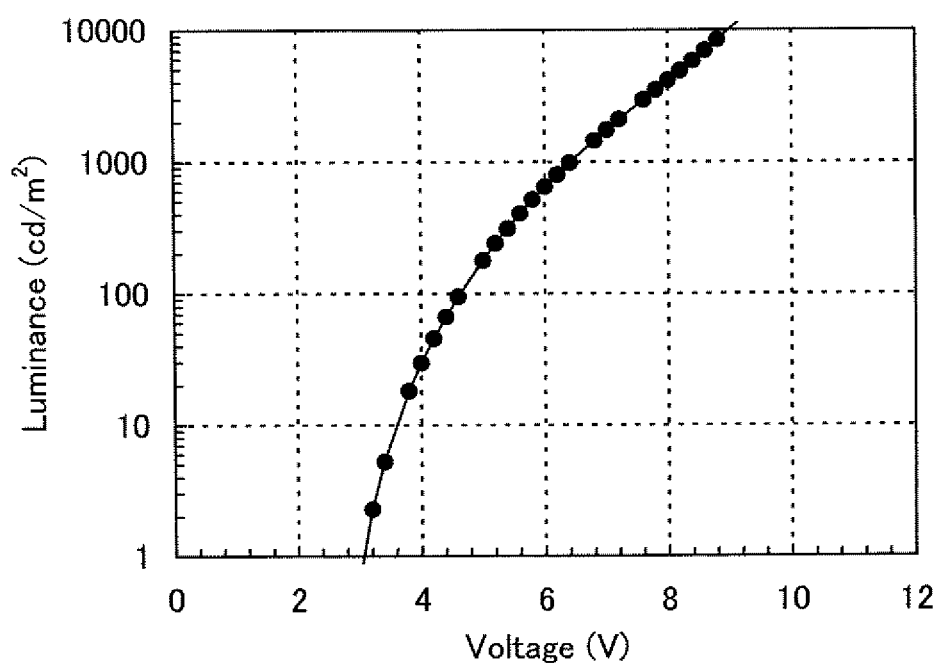
FIG. 22 illustrates voltage-luminance characteristics of a light-emitting element fabricated in Example 3.
Figure 23:
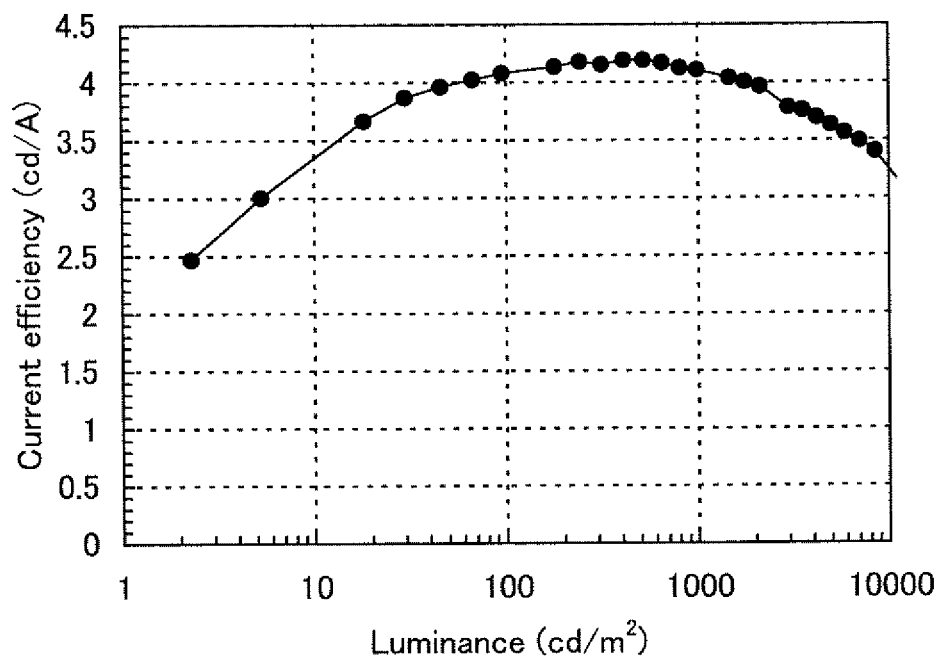
FIG. 23 illustrates luminance-current efficiency characteristics of a light-emitting element fabricated in Example 3.
Figure 24:
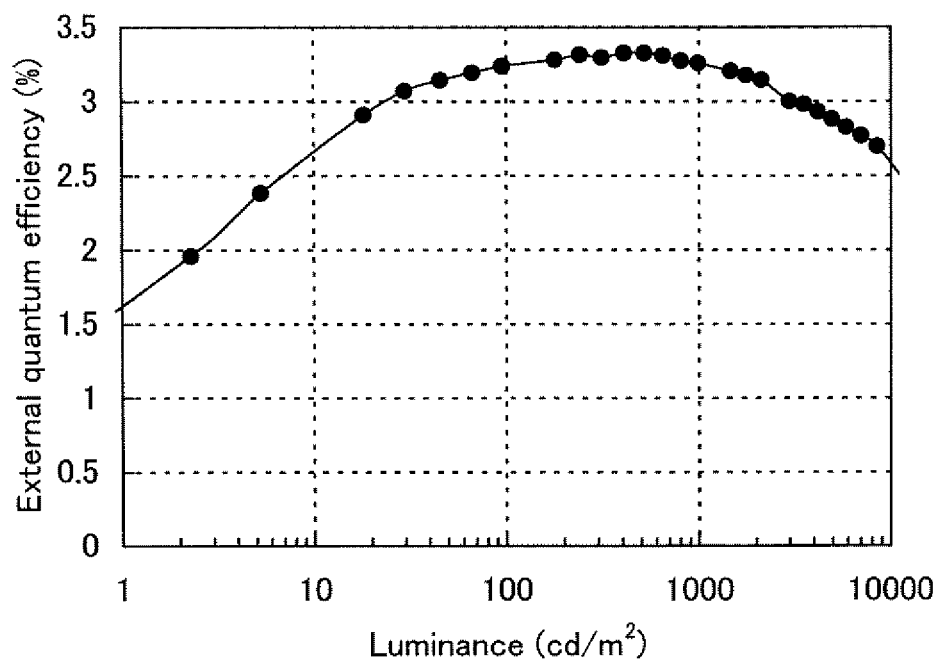
FIG. 24 illustrates luminance-external quantum efficiency characteristics of a light-emitting element fabricated in Example 3.

In this example, a light-emitting element of the present invention is described using FIG. 20. Chemical formulae of materials used in this example are shown below.

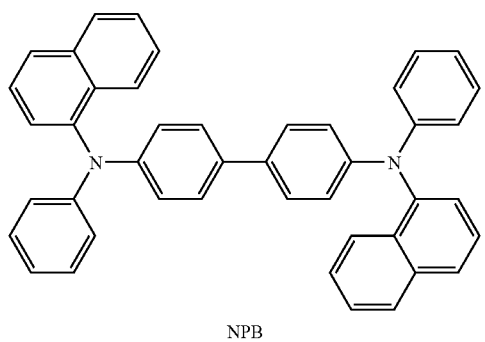

NPB

-continued

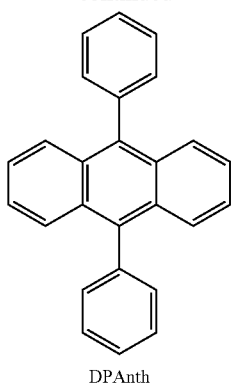
DPAnth

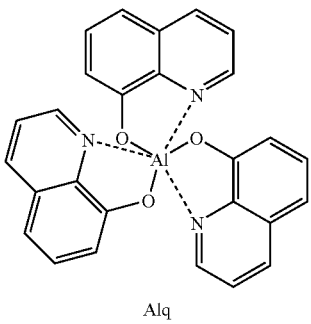
Alq

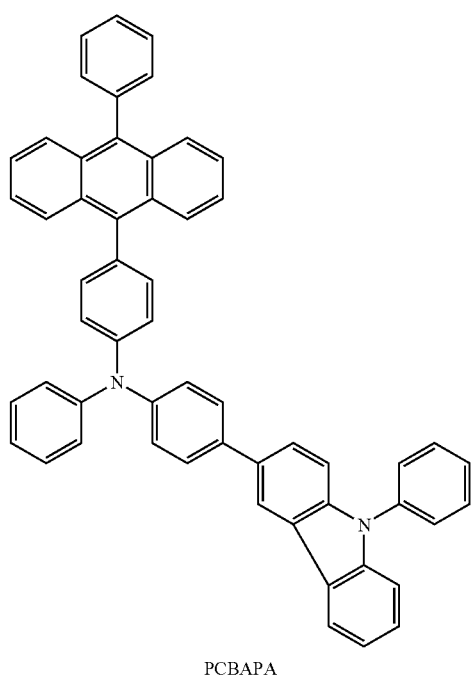
PCBAPA

-continued

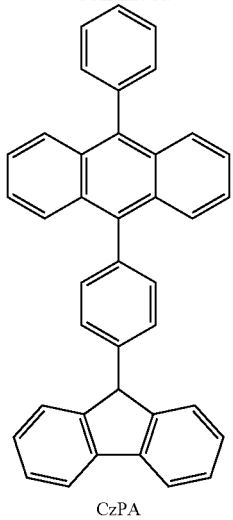
CzPA (Light-Emitting Element 2)

First, indium tin oxide containing silicon oxide was deposited over a glass substrate 2100 by a sputtering method, whereby a first electrode 2101 was formed. It is to be noted that the film thickness of the first electrode was set to be 110 nm and that the area of the electrode was set to be 2 mm×2 mm.

Next, the substrate over which the first electrode was formed was fixed to a substrate holder provided in a vacuum deposition apparatus so that a surface on which the first electrode was formed faced downward. After the pressure of the vacuum deposition apparatus was reduced to about $10^{-4}$ Pa, a layer 2102 containing a composite material of an organic compound and an inorganic compound was formed over the first electrode 2101 by co-deposition of NPB and molybdenum(VI) oxide. The film thickness of the layer 2102 was set to be 50 nm, and the weight ratio of NPB and molybdenum(VI) oxide was adjusted so as to be 4:1(=NPB:molybdenum oxide). It is to be noted that the co-deposition method is a deposition method in which deposition is performed from a plurality of evaporation sources at the same time in one treatment chamber.

Next, NPB was deposited over the layer 2102 containing a composite material to a thickness of 10 nm by a deposition method using resistive heating, whereby a hole-transporting layer 2103 was formed.

Further, by co-deposition of 9,10-diphenylanthracene (DPAnth) and the anthracene derivative PCBAPA of the present invention, a first layer 2121 was formed over the hole-transporting layer 2103 to a thickness of 30 nm. The weight ratio of DPAnth and PCBAPA was adjusted so as to be 1:0.05(=DPAnth:PCBAPA).

Further, by co-deposition of 9-[4-(10-phenyl-9-anthryl)phenyl]-9H-carbazole (CzPA) and the anthracene derivative PCBAPA of the present invention, a second layer 2122 was formed over the first layer 2121 to a thickness of 30 nm. The weight ratio of CzPA and PCBAPA was adjusted so as to be 1:0.10(=CzPA:PCBAPA).

Thereafter, tris(8-quinolinolato)aluminum (Alq) was deposited over the second layer 2122 to a thickness of 10 nm by a deposition method using resistive heating, whereby an electron-transporting layer 2104 was formed.

Further, by co-deposition of tris(8-quinolinolato)aluminum (Alq) and lithium, an electron-injecting layer 2105 was formed over the electron-transporting layer 2104 to a thickness of 20 nm. The weight ratio of Alq and lithium was adjusted so as to be 1:0.01(=Alq:lithium).

Lastly, aluminum was deposited over the electron-injecting layer 2105 to a thickness of 200 nm by a deposition method using resistive heating, whereby a second electrode 2106 was formed. Accordingly, a light-emitting element 2 was fabricated.

Figure 25:
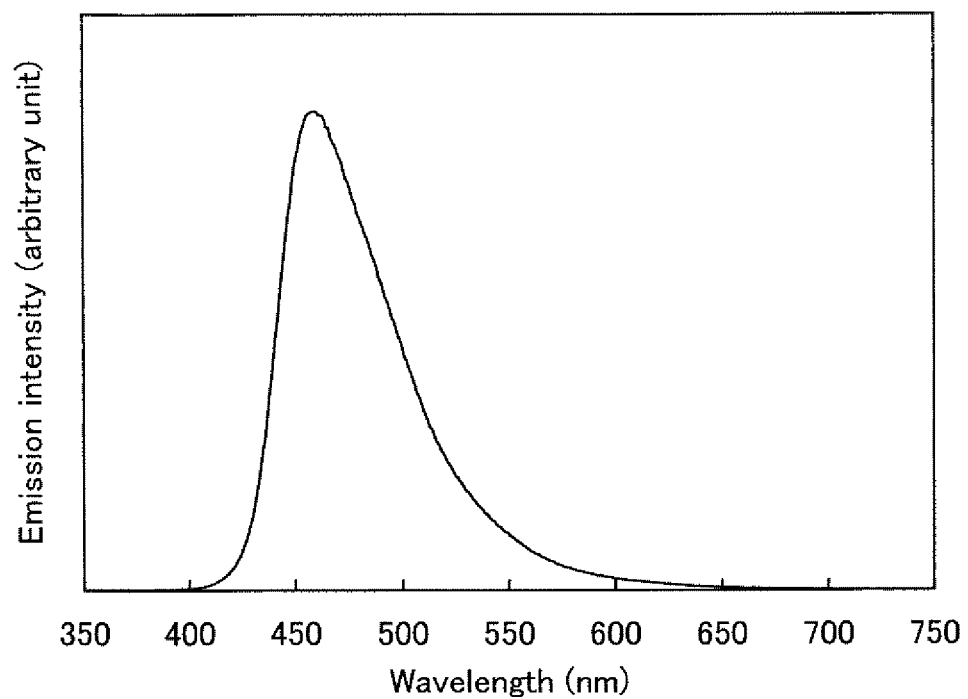
FIG. 25 illustrates an emission spectrum of a light-emitting element fabricated in Example 3.

Current density-luminance characteristics, voltage-luminance characteristics, luminance-current efficiency characteristics, and luminance-external quantum efficiency of the light-emitting element 2 are shown in FIG. 21, FIG. 22, FIG. 23, and FIG. 24, respectively. Also, the emission spectrum measured at a current of 1 mA is shown in FIG. 25. From FIG. 25, it can be seen that light emitted from the light-emitting element was from PCBAPA. A CIE chromaticity coordinates of the light-emitting element 2 at luminance of 990 cd/m$^2$ were (x, y)=(0.15, 0.17), which are indicative of blue light with high color purity. As can be seen from FIG. 24, the external quantum efficiency of the light-emitting element 2 measured at luminance of 990 cd/m$^2$ was 3.3%, which is indicative of high external quantum efficiency. Thus, the light-emitting element 2 has high emission efficiency. From FIG. 23, it can be seen that the current efficiency of the light-emitting element 2 measured at luminance of 990 cd/m$^2$ was 4.1 cd/A, which is indicative of high luminous efficiency. From FIG. 22, the driving voltage of the light-emitting element 2 measured at luminance of 990 cd/m$^2$ was 6.4 V, and a voltage needed to obtain a given luminance is low. Thus, it is found that power consumption for the light-emitting element 2 is low.

Figure 27:
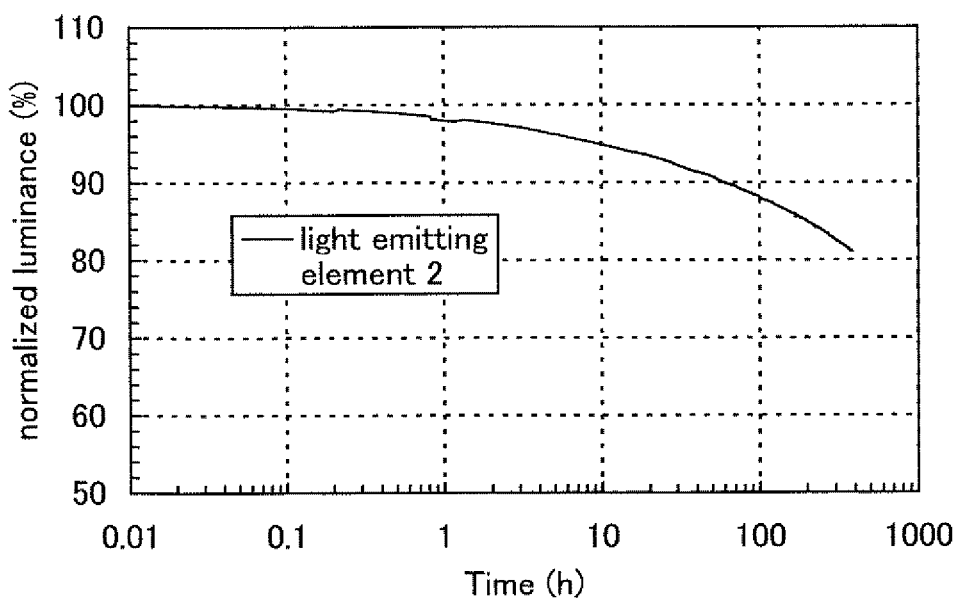
FIG. 27 illustrates a result of a continuous lighting test of a light-emitting element fabricated in Example 3.

In addition, when the light-emitting element 1 of this example was driven under conditions of an initial luminance set to 1000 cd/m2 and a constant instant current density, luminance after 380 hours was retained at 81% of the initial luminance. The results are shown in FIG. 27. In FIG. 27, the horizontal axis indicates time (h) and the vertical axis indicates normalized luminance where the initial luminance was 100%. Consequently, it is found that a light-emitting element with little deterioration and a long life can be obtained by application of the present invention.

[Example 4]

In this example, a synthesis method of an anthracene derivative 4-[4-(10-phenyl-9-anthryl)phenyl]-4'-(9-phenyl-9H-carbazol-3-yl)triphenylamine (PCBAPBA) of the present invention represented by a structural formula (300) is described in specific terms.

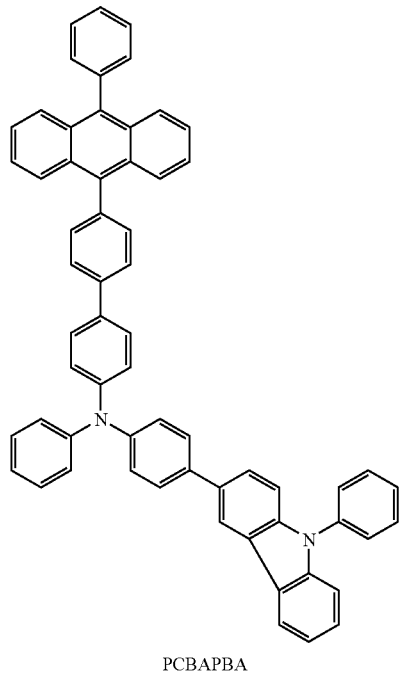

(300)

PCBAPBA

Step 1: Synthesis of 9-(4'-bromobiphenyl-4-yl)-10-phenylanthracene

Into a 100 mL three-neck flask were put 2.8 g (7.2 mmol) of 9-iodine-10-phenylanthracene and 1.5 g (7.2 mmol) of 4'-bromobiphenyl-4-boronic acid. The air in the flask was replaced with nitrogen. To the mixture were added 40 mL of toluene and 10 mL (2.0 mol/L) of an aqueous solution of sodium carbonate. This mixture was stirred to be degassed while the pressure was being reduced. After the degassing, 120 mg (0.10 mmol) of tetrakis(triphenylphosphine)palladium(0) were added to the mixture. This mixture was stirred at 90° C. for 4 hours. After the stirring, about 50 mL of toluene were added to this mixture. The mixture was subjected to suction filtration through alumina, celite (produced by Wako Pure Chemical Industries, Ltd., Catalog No. 531-16855), and Florisil (produced by Wako Pure Chemical Industries, Ltd., Catalog No. 540-00135). The solid obtained by condensation of the obtained filtrate was purified by high-performance liquid chromatography (a mobile phase: chloroform) to give a light yellow solid. The obtained solid was recrystallized with chloroform/hexane to give 1.4 g of a light yellow powdered solid, which was the object of the synthesis, at a yield of 40%. A synthesis scheme of Step 1 is shown in (c-1) given below.

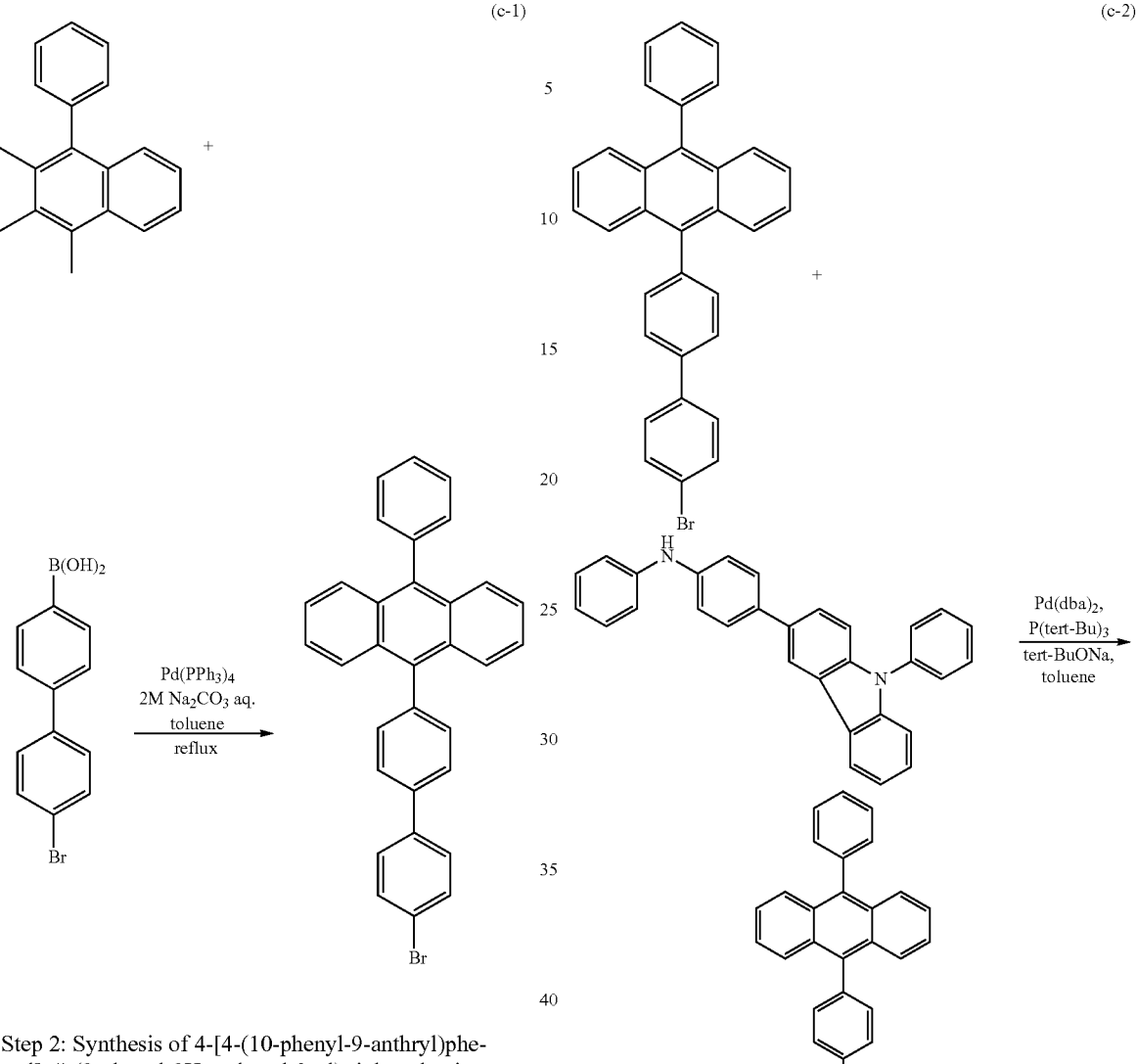

(c-1)

(c-2)

Step 2: Synthesis of 4-[4-(10-phenyl-9-anthryl)phenyl]-4'-(9-phenyl-9H-carbazol-3-yl)triphenylamine (PCBAPBA)

Into a 50 mL three-neck flask were put 1.0 g (2.1 mmol) of 9-(4'-bromobiphenyl-4-yl)-10-phenylanthracene, 845 mg (2.1 mmol) of 4-(9-phenyl-9H-carbazol-3-yl)diphenylamine (PCBA), and 1.0 g (10 mmol) sodium tert-butoxide. The air in the flask was replaced with nitrogen. To the mixture were added 15 mL of toluene and 0.10 mL of tri(tert-butyl)phosphine (a 10 wt % hexane solution). Under reduced pressure, this mixture was degassed while being stirred. After the degassing, 58 mg (0.10 mmol) of bis(dibenzylideneacetone)palladium(0) were added to the mixture. This mixture was stirred at 100° C. for 5 hours. After the stirring, the temperature of the mixture was cooled to room temperature, and then about 20 mL of toluene were added to the mixture. The mixture was subjected to filtration through Florisil (produced by Wako Pure Chemical Industries, Ltd., Catalog No. 540-00135), celite (produced by Wako Pure Chemical Industries, Ltd., Catalog No. 531-16855), and alumina. The obtained filtrate was condensed to give a light yellow solid. This obtained solid was recrystallized with toluene/hexane to give 1.5 g of a light yellow powdered solid, which was the object of the synthesis, at a yield of 90%. A synthesis scheme of Step 2 is shown in (c-2) given below.

Then, 1.1 g of the obtained light yellow powdered solid was purified by train sublimation. For sublimation purification conditions, PCBAPBA was heated at 380° C. under a pressure of 6.0 Pa with a flow rate of argon gas of 3.0 mL/min. After the sublimation purification, 1.0 g of a light yellow solid was obtained at a yield of 93%.

Figure 28A:
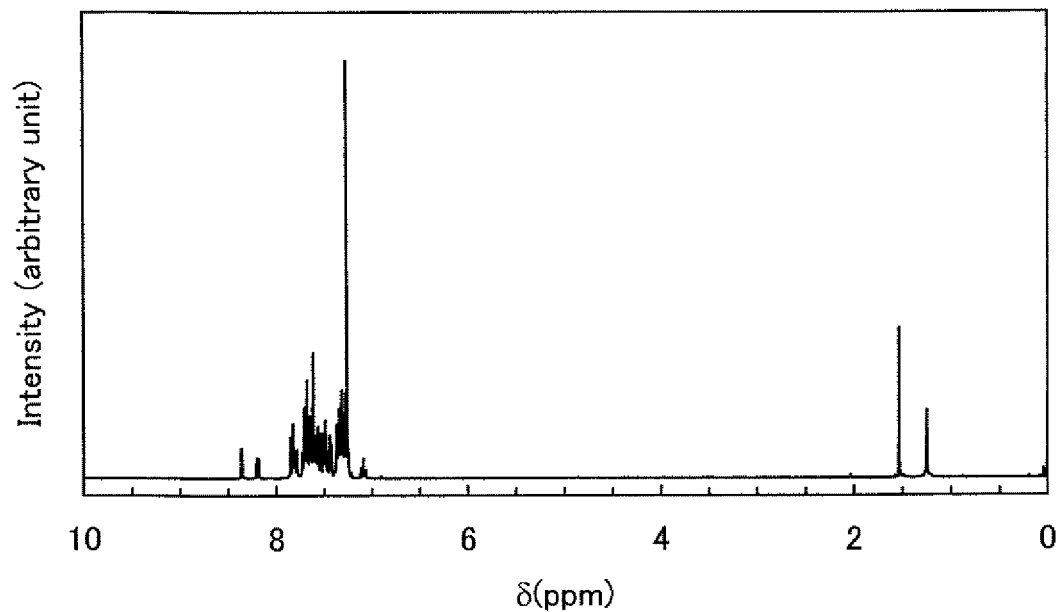
FIGS. 28A and 28B are $^1$H-NMR charts of 4-[4-(10-phenyl-9-anthryl)phenyl]-4'-(9-phenyl-9H-carbazol-3-yl)triphenylamine (abbreviated to PCBAPBA).
Figure 28B:
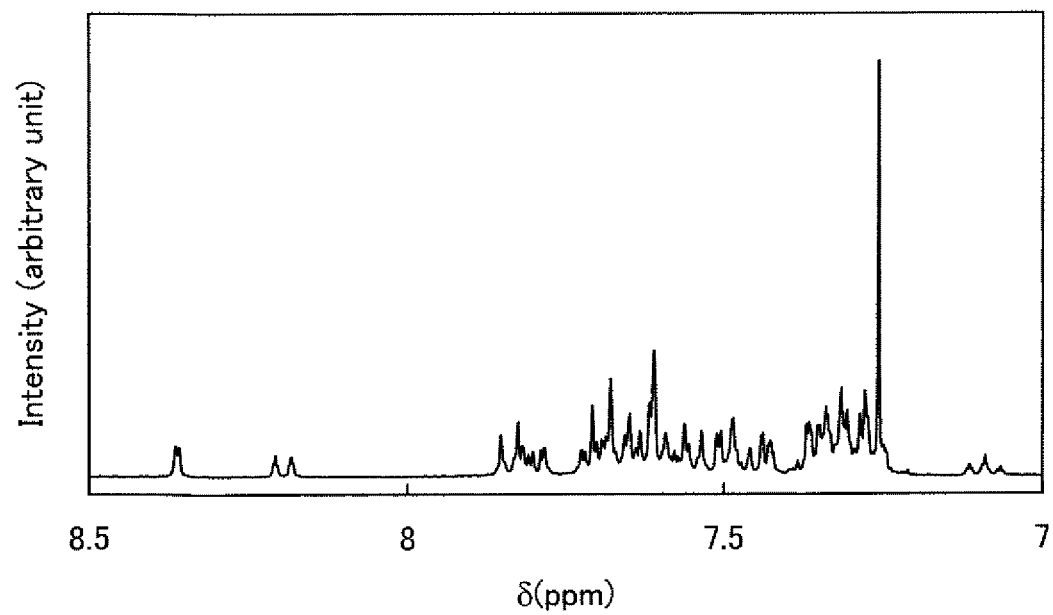

The obtained solid was analyzed by $^1$H NMR. The measurement results are described below, and the $^1$H NMR chart is shown in FIGS. 28A and 28B. It is to be noted that FIG. 28B is a chart showing an enlarged view of the range of 7.0 to 8.5 ppm in FIG. 28A. From the measurement results, it can be seen that the anthracene derivative PCBAPBA of the present invention represented by the above structural formula (300) was obtained.

$^1$H NMR (DMSO-d$_6$, 300 MHz): δ=7.09-7.12 (m, 1H), 7.25-7.31 (m, 12H), 7.34-7.79 (m, 23H), 7.80-7.85 (m, 4H), 8.20 (d, J=7.8 Hz, 1H), 8.36 (d, J=1.5 Hz, 1H)

Further, thermogravimetry-differential thermal analysis (TG-DTA) of PCBAPBA was carried out using a high vacuum differential type differential thermal balance (TG-DTA2410SA, manufactured by Bruker AXS K.K.). The measurement was performed under normal pressure in a stream of nitrogen (at a flow rate of 200 mL/min) at a rate of temperature increase of 10° C./min. From the relationship between the weight and the temperature (thermogravimetry), it was understood that a 5% weight reduction was seen at temperatures of more than 500° C., which is indicative of high thermal stability.

Figure 29:
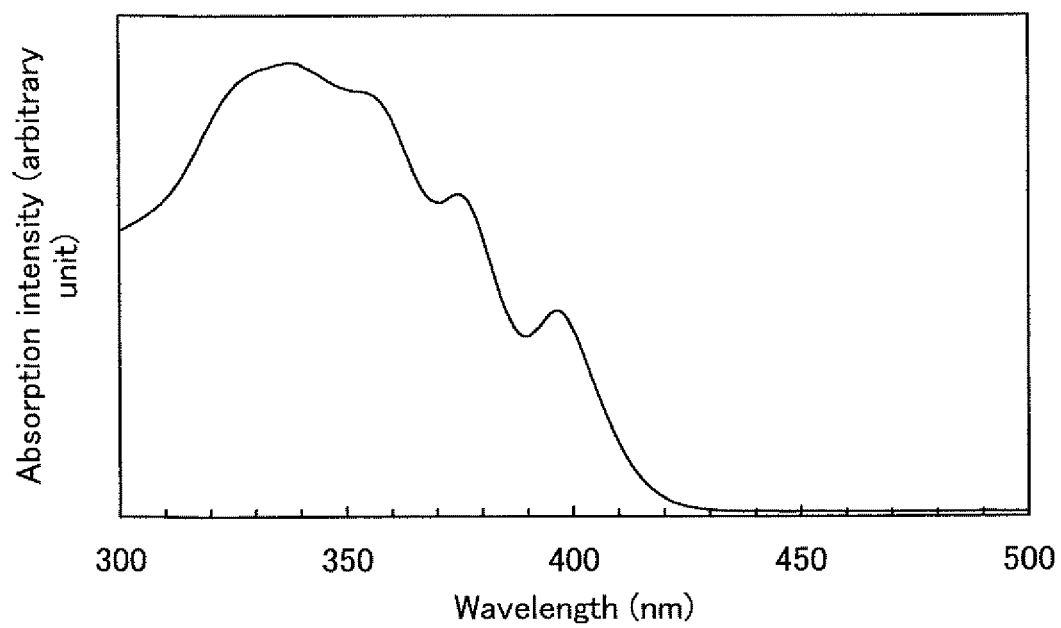
FIG. 29 illustrates an absorption spectrum of a toluene solution of 4-[4-(10-phenyl-9-anthryl)phenyl]-4'-(9-phenyl-9H-carbazol-3-yl)triphenylamine (PCBAPBA).
Figure 30:
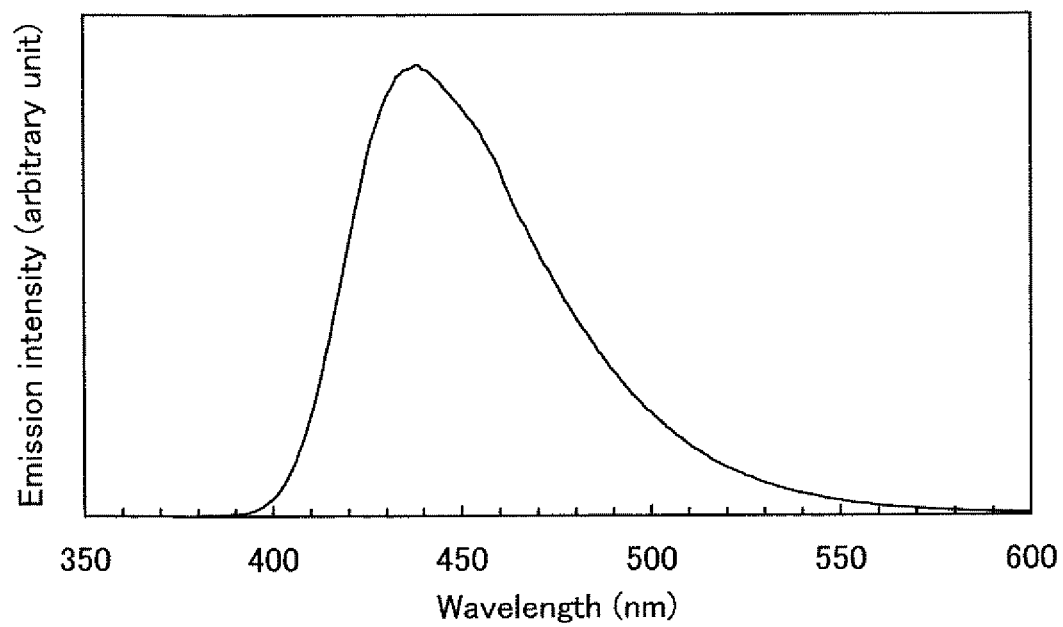
FIG. 30 illustrates an emission spectrum of a toluene solution of 4-[4-(10-phenyl-9-anthryl)phenyl]-4'-(9-phenyl-9H-carbazol-3-yl)triphenylamine (PCBAPBA).

Next, an absorption spectrum of PCBAPBA was measured using an ultraviolet-visible spectrophotometer (V-550, manufactured by JASCO Corporation) at room temperature with the use of a toluene solution. The measurement results are shown in FIG. 29. In FIG. 29, the horizontal axis indicates the wavelength (nm) and the vertical axis indicates the absorption intensity (arbitrary unit). Further, an emission spectrum of PCBAPBA was measured using a fluorescence spectrophotometer (FS920, manufactured by Hamamatsu Photonics Corporation) at room temperature with the use of a toluene solution. The measurement results are shown in FIG. 30. In FIG. 30, the horizontal axis indicates the wavelength (nm) and the vertical axis indicates the emission intensity (arbitrary unit). Absorption of the toluene solution of PCBAPBA was seen at around 373 nm and around 395 nm. The maximum emission wavelength of the toluene solution was 440 nm (an excitation wavelength of 370 nm).

Figure 31:
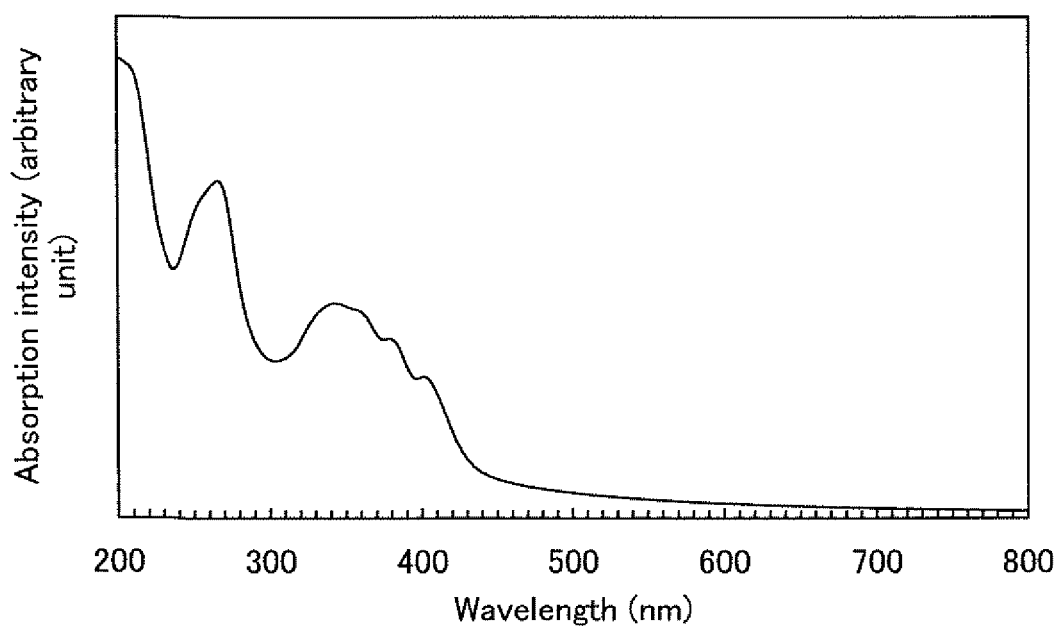
FIG. 31 illustrates an absorption spectrum of a thin film of 4-[4-(10-phenyl-9-anthryl)phenyl]-4'-(9-phenyl-9H-carbazol-3-yl)triphenylamine (PCBAPBA).
Figure 32:
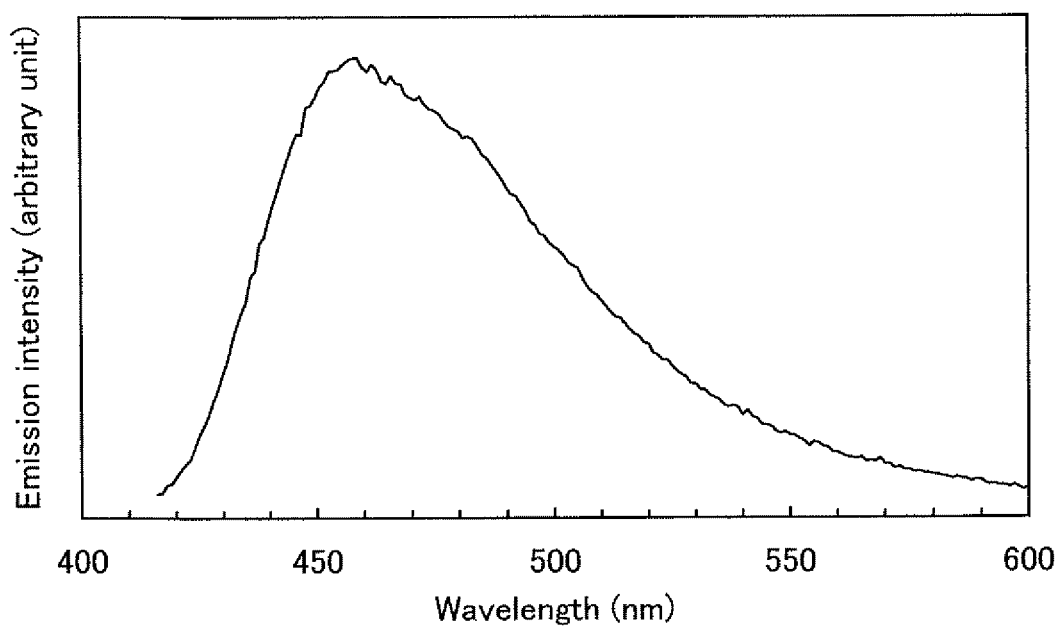
FIG. 32 illustrates an emission spectrum of a thin film of 4-[4-(10-phenyl-9-anthryl)phenyl]-4'-(9-phenyl-9H-carbazol-3-yl)triphenylamine (PCBAPBA).

Further, PCBAPBA was deposited by a deposition method, and a thin film of PCBAPA was measured in a similar manner. An absorption spectrum of the thin film of PCBAPA is shown in FIG. 31, and an emission spectrum thereof is shown in FIG. 32. In FIG. 31, the horizontal axis indicates the wavelength (nm) and the vertical axis indicates the absorption intensity (arbitrary unit). In FIG. 32, the horizontal axis indicates the wavelength (nm) and the vertical axis indicates the emission intensity (arbitrary unit). Absorption of the thin film of PCBAPBA was seen at around 267 nm, around 343 nm, around 379 nm, and around 402 nm. The maximum emission wavelength of the toluene solution was 458 nm (an excitation wavelength of 400 nm).

From FIG. 30 and FIG. 32, it can be seen that PCBAPBA emits blue light with high color purity.

[Example 5]

In this example, a light-emitting element of the present invention is described using FIG. 14. Chemical formulae of materials used in this example are shown below.

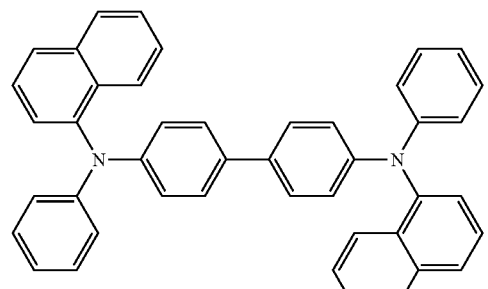
NPB

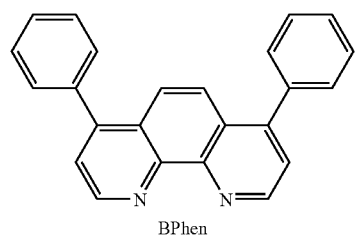
BPhen

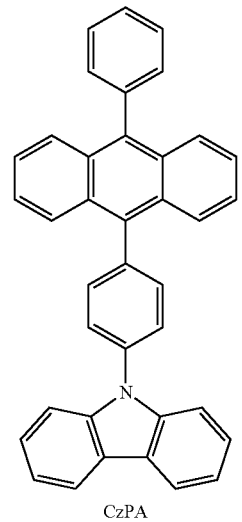
CzPA

-continued

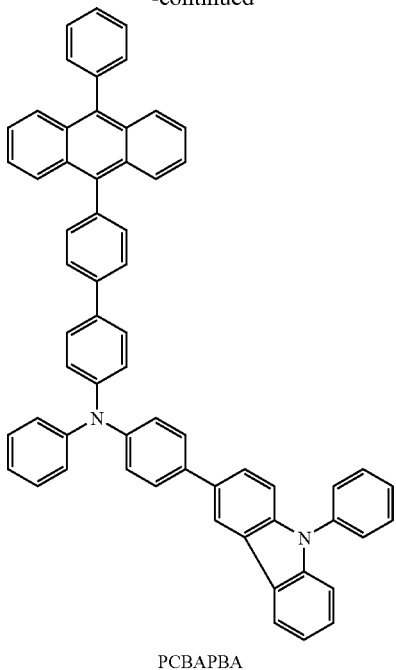

PCBAPBA (Light-Emitting Element 3)

First, indium tin oxide containing silicon oxide was deposited over a glass substrate 1100 by a sputtering method, whereby a first electrode 1101 was formed. It is to be noted that the film thickness of the first electrode was set to be 110 nm and that the area of the electrode was set to be 2 mm×2 mm.

Next, the substrate over which the first electrode was formed was fixed to a substrate holder provided in a vacuum deposition apparatus so that a surface on which the first electrode was formed faced downward. After the pressure of the vacuum deposition apparatus was reduced to about $10^{-4}$ Pa, a layer 1102 containing a composite material of an organic compound and an inorganic compound was formed over the first electrode 1101 by co-deposition of NPB and molybdenum(VI) oxide. The film thickness of the layer 1102 was set to be 50 nm, and the weight ratio of NPB and molybdenum (VI) oxide was adjusted so as to be 4:1(=NPB:molybdenum oxide). It is to be noted that the co-deposition method is a deposition method in which deposition is carried out from a plurality of evaporation sources at the same time in one treatment chamber.

Next, NPB was deposited over the layer 1102 containing a composite material to a thickness of 10 nm by a deposition method using resistive heating, whereby a hole-transporting layer 1103 was formed.

Further, by co-deposition of 9-[4-(10-phenyl-9-anthryl) phenyl]-9H-carbazole (CzPA) and PCBAPBA, a light-emitting layer 1104 was formed over the hole-transporting layer 1103 to a thickness of 30 nm. The weight ratio of CzPA and PCBAPBA was adjusted so as to be 1:0.10(=CzPA: PCBAPBA).

Thereafter, bathophenanthroline (BPhen) was deposited over the light-emitting layer 1104 to a thickness of 30 nm by a deposition method using resistive heating, whereby an electron-transporting layer 1105 was formed.

Furthermore, lithium fluoride (LiF) was deposited over the electron-transporting layer 1105 to a thickness of 1 nm, whereby an electron-injecting layer 1106 is formed.

Lastly, aluminum was deposited over the electron-injecting layer 1106 to a thickness of 200 nm by a deposition method using resistive heating, whereby a second electrode 1107 was formed. Accordingly, a light-emitting element 3 was fabricated.

Figure 33:
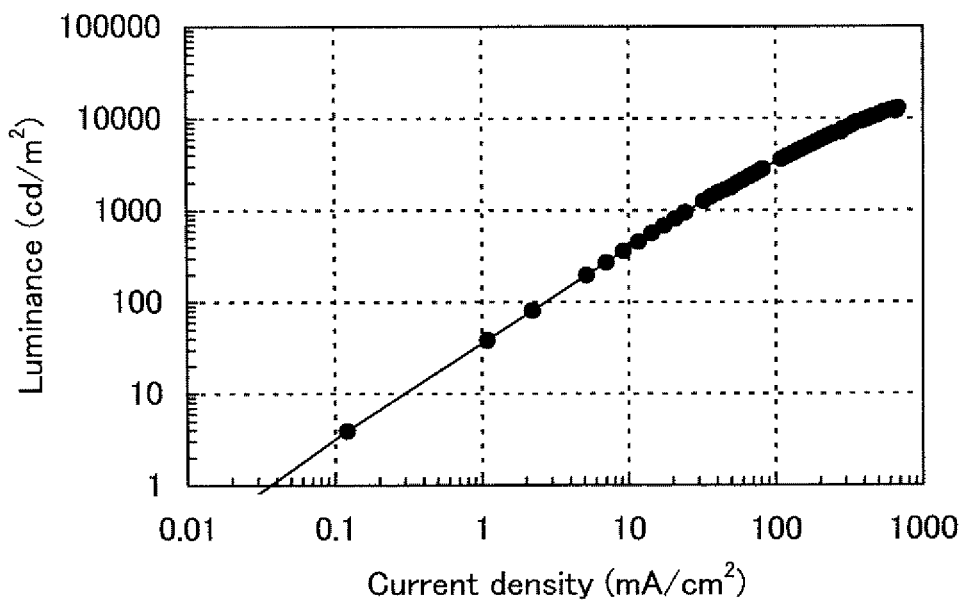
FIG. 33 illustrates current density-luminance characteristics of a light-emitting element fabricated in Example 5.
Figure 34:
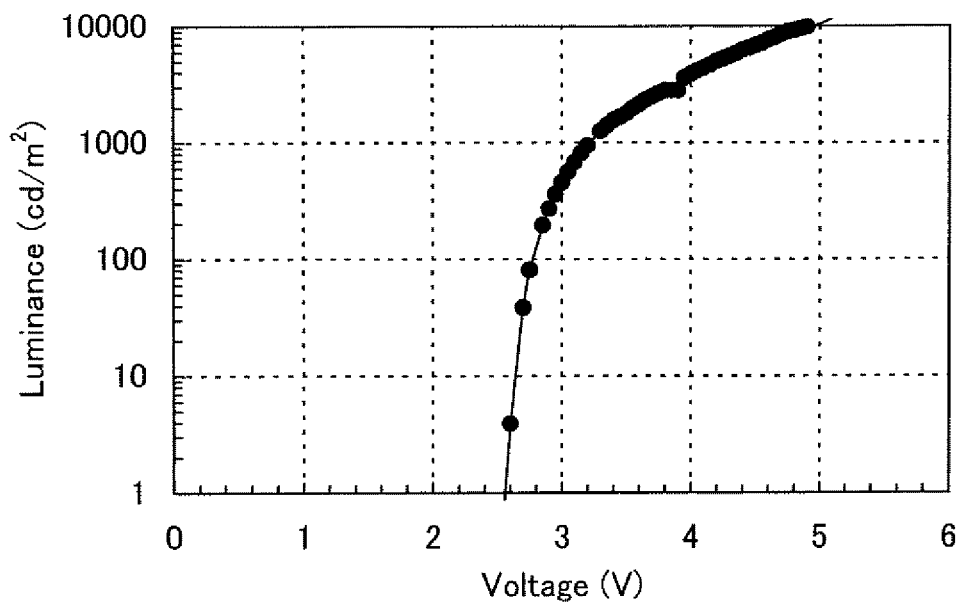
FIG. 34 illustrates voltage-luminance characteristics of a light-emitting element fabricated in Example 5.
Figure 35:
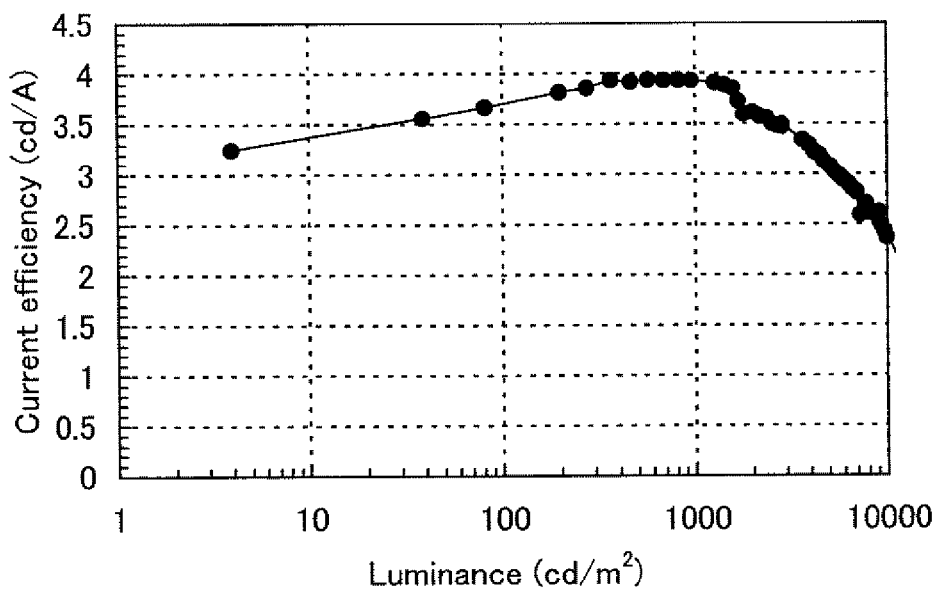
FIG. 35 illustrates luminance-current efficiency characteristics of a light-emitting element fabricated in Example 5.
Figure 36:
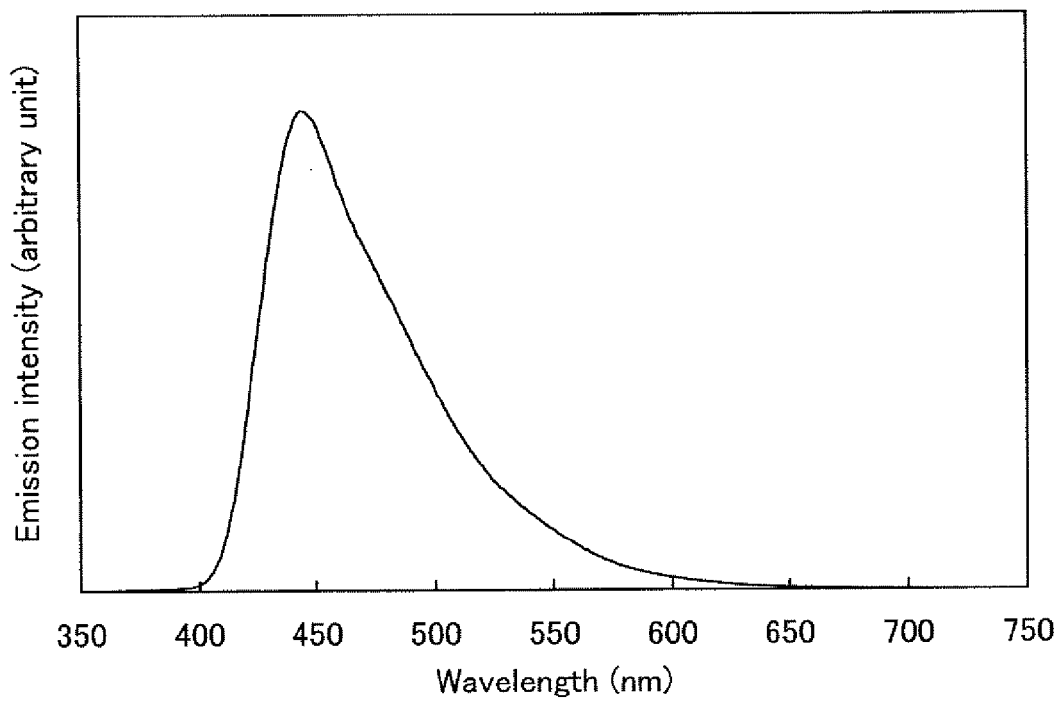
FIG. 36 illustrates an emission spectrum of a light-emitting element fabricated in Example 5.

Current density-luminance characteristics, voltage-luminance characteristics, and luminance-current efficiency characteristics of the light-emitting element 3 are shown in FIG. 33, FIG. 34, and FIG. 35, respectively. Also, the emission spectrum measured at a current of 1 mA is shown in FIG. 36. From FIG. 36, it can be seen that light emitted from the light-emitting element was from PCBA BA. A CIE chromaticity coordinates of the light-emitting element 3 at luminance of 950 cd/$^2$ were (x, y)=(0.15, 0.12), which are indicative of blue light with high color purity. The external quantum efficiency of the light-emitting element 3 measured at luminance of 950 cd/m$^2$ was 3.7%, which is indicative of high external quantum efficiency. From FIG. 35, it can be seen that the current efficiency of the light-emitting element 3 measured at luminance of 950 cd/m$^2$ was 3.9 cd/A, which is indicative of high luminous efficiency. From FIG. 34, the driving voltage of the light-emitting element 3 measured at luminance of 950 cd/m$^2$ was 3.2 V, and a voltage needed to obtain a given luminance is low. Furthermore, the power efficiency of the light-emitting element 3 was 3.9 lm/W, and thus, it is found that power consumption for the light-emitting element 3 is low.

This application is based on Japanese Patent Application serial no. 2007-115079 filed with Japan Patent Office on Apr. 25, 2007,and Japanese Patent Application serial no. 2008-011127 filed with Japan Patent Office on Jan. 22, 2008, the entire contents of which are hereby incorporated by reference.

What is claimed is:

1. An anthracene derivative represented by a general formula (1),

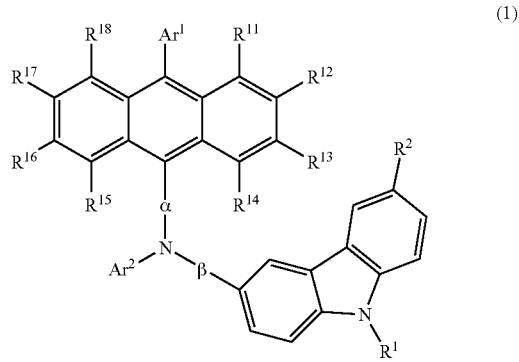

wherein Ar$^1$ is a phenyl group, wherein Ar$^2$ is represented by a structure (Ar-18) or (Ar-19), (Ar-18)

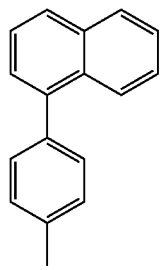

(108)

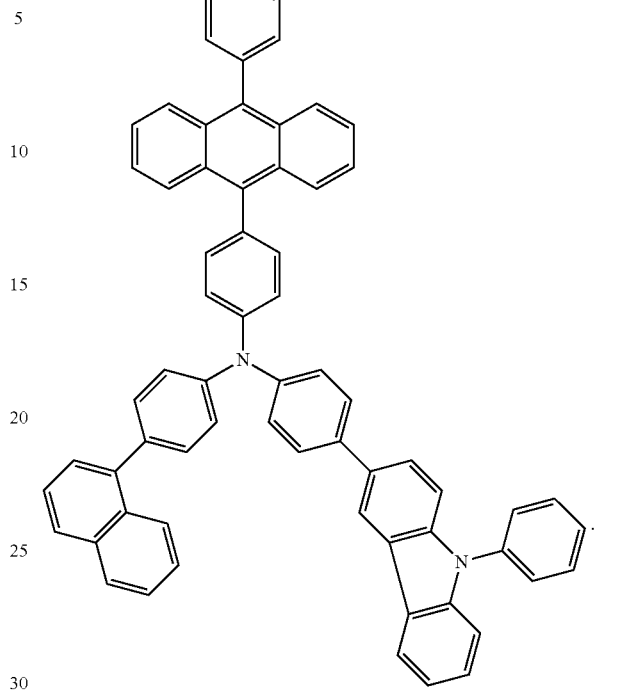

(Ar-19)

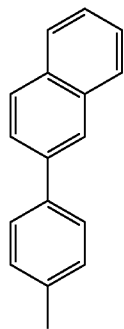

5. The anthracene derivative according to claim 1, wherein the anthracene derivative is represented by a structural formula (109), (109)

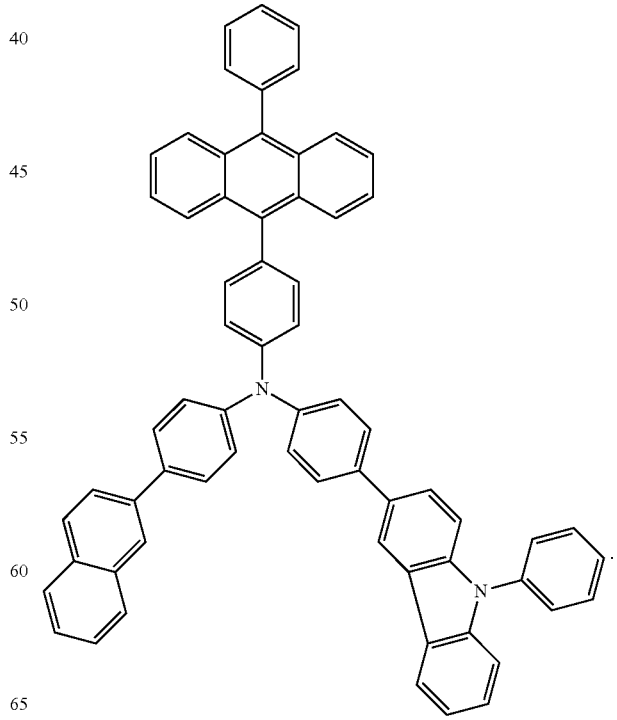

wherein α and β each represent a phenylene group, wherein $R^1$ represents an alkyl group having 1 to 4 carbon atoms or a substituted or unsubstituted aryl group having 6 to 25 carbon atoms, wherein $R^2$ represents one of hydrogen, an alkyl group having 1 to 4 carbon atoms, a substituted or unsubstituted aryl group having 6 to 25 carbon atoms, a halogen group, and a haloalkyl group, and wherein $R^{11}$ to $R^{18}$ each represent hydrogen or an alkyl group having 1 to 4 carbon atoms.

2. A light-emitting element comprising a light-emitting layer between a pair of electrodes, wherein the light-emitting layer includes the anthracene derivative according to claim 1.

3. A light-emitting device comprising the light-emitting element according to claim 2 and a control circuit configured to control light emission from the light-emitting element.

4. The anthracene derivative according to claim 1, wherein the anthracene derivative is represented by a structural formula (108), 6. An anthracene derivative represented by a general formula (6),

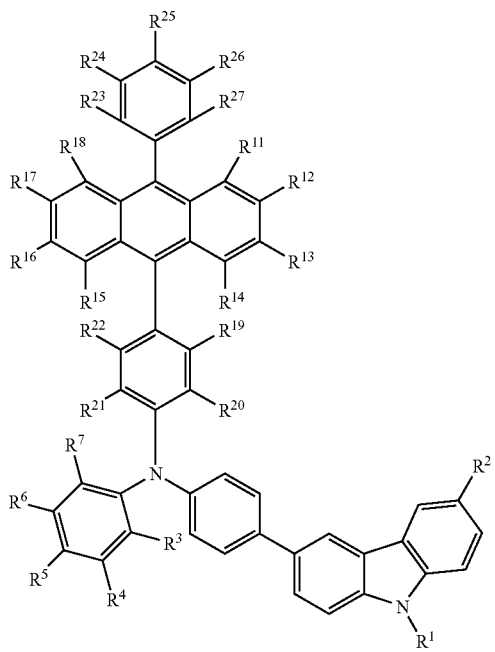

(6)

wherein $R^1$ represents an alkyl group having 1 to 4 carbon atoms or a substituted or unsubstituted aryl group having 6 to 25 carbon atoms, wherein $R^2$ represents one of hydrogen, an alkyl group having 1 to 4 carbon atoms, a substituted or unsubstituted aryl group having 6 to 25 carbon atoms, a halogen group, and a haloalkyl group, wherein $R^3$ to $R^7$ each represent one of hydrogen, an alkyl group having 1 to 4 carbon atoms, a halogen group, and a haloalkyl group, wherein $R^{11}$ to $R^{18}$ each represent hydrogen or an alkyl group having 1 to 4 carbon atoms, and wherein $R^{19}$ to $R^{27}$ each represent one of hydrogen, an alkyl group having 1 to 4 carbon atoms, and an alkoxy group having 1 to 4 carbon atoms.

7. The anthracene derivative according to claim 6, wherein the anthracene derivative is represented by a structural formula (100),

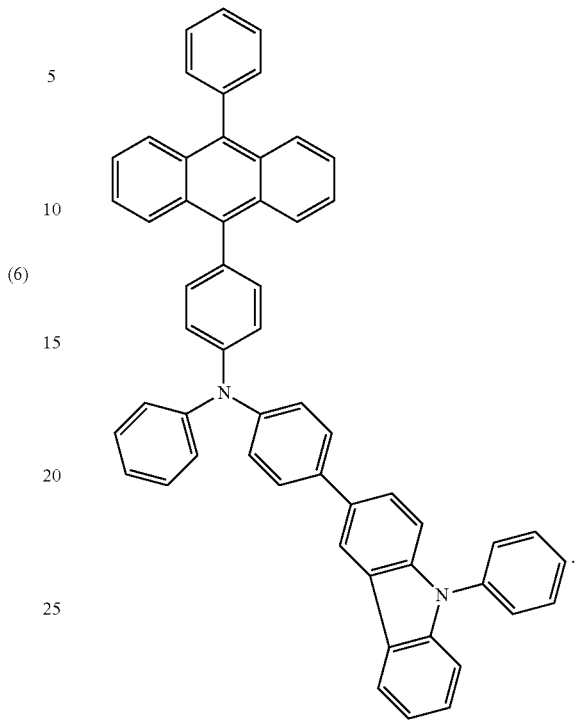

(100)

8. A light-emitting element comprising a light-emitting layer between a pair of electrodes, wherein the light-emitting layer includes the organic compound represented by a general formula (8),

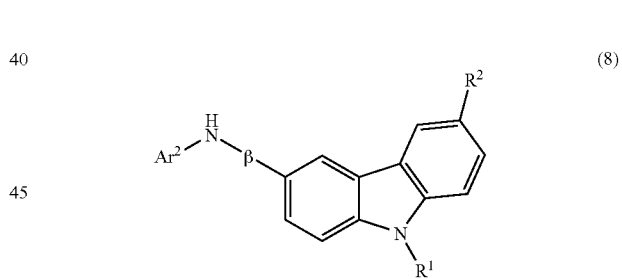

(8)

wherein $Ar^2$ represents a substituted or unsubstituted aryl group having 6 to 25 carbon atoms, wherein $\beta$ represents a substituted or unsubstituted arylene group having 6 to 25 carbon atoms, wherein $R^1$ represents an alkyl group having 1 to 4 carbon atoms or a substituted or unsubstituted aryl group having 6 to 25 carbon atoms, and wherein $R^2$ represents one of hydrogen, an alkyl group having 1 to 4 carbon atoms, an unsubstituted aryl group having 6 to 25 carbon atoms, a halogen group, and a haloalkyl group.

9. A light-emitting device comprising the light-emitting element according to claim 8 and a control circuit configured to control light emission from the light-emitting element.

10. An anthracene derivative represented by a general formula (1),

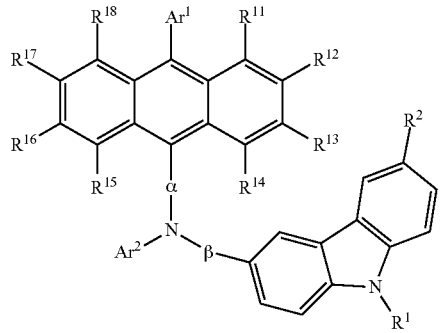
(1)

wherein Ar¹ and Ar² each represent a phenyl group,
wherein α represents a phenylene group,
wherein β is represented by one of the structures (β-1), (β-2), or (β-10),

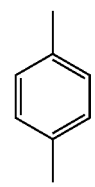
(β-1)

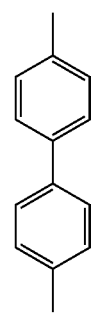
(β-2)

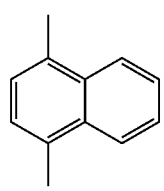
(β-10)

wherein R¹ is represented by one of the structures (R1-9), (R1-15), (R1-16), or (R1-17),

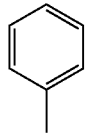
(R1-9)

-continued

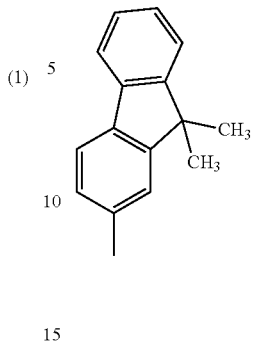
(R1-15)

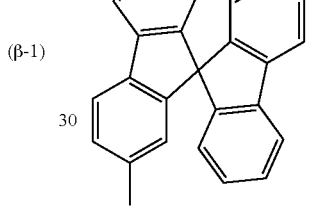
(R1-16)

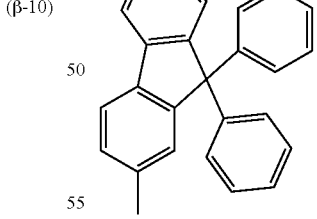
(R1-17)

wherein R² represents one of hydrogen, an alkyl group having 1 to 4 carbon atoms, a substituted or unsubstituted aryl group having 6 to 25 carbon atoms, a halogen group, and a haloalkyl group, and wherein R¹¹ to R¹⁸ each represent hydrogen or an alkyl group having 1 to 4 carbon atoms.

11. The anthracene derivative according to claim 10, wherein the anthracene derivative is represented by a structural formula (140),

12. The anthracene derivative according to claim 10, wherein the anthracene derivative is represented by a structural formula (141), (140)

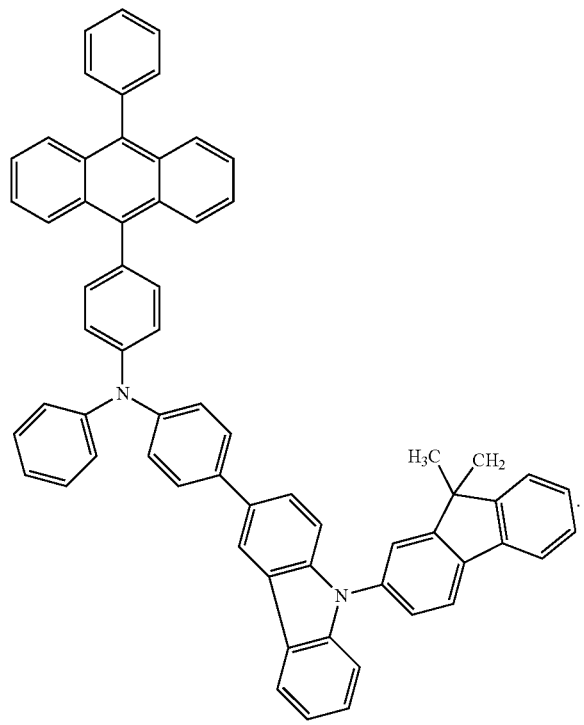

(141)

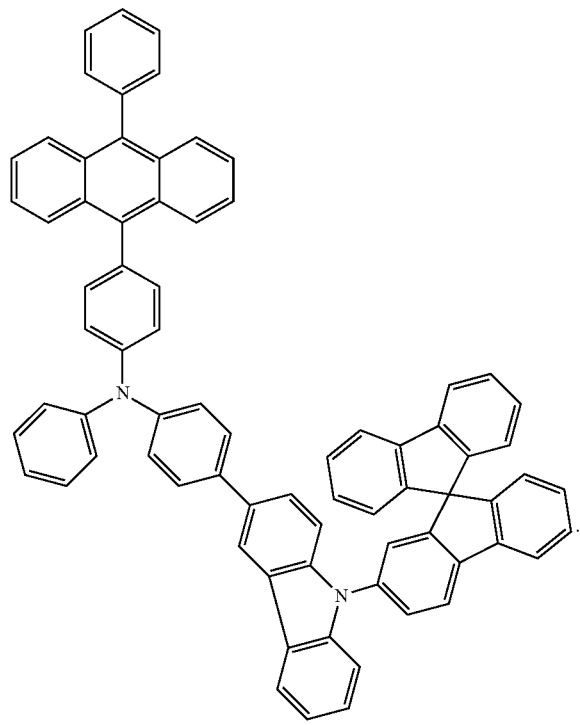

13. The anthracene derivative according to claim 10, wherein the anthracene derivative is represented by a structural formula (142), (142)

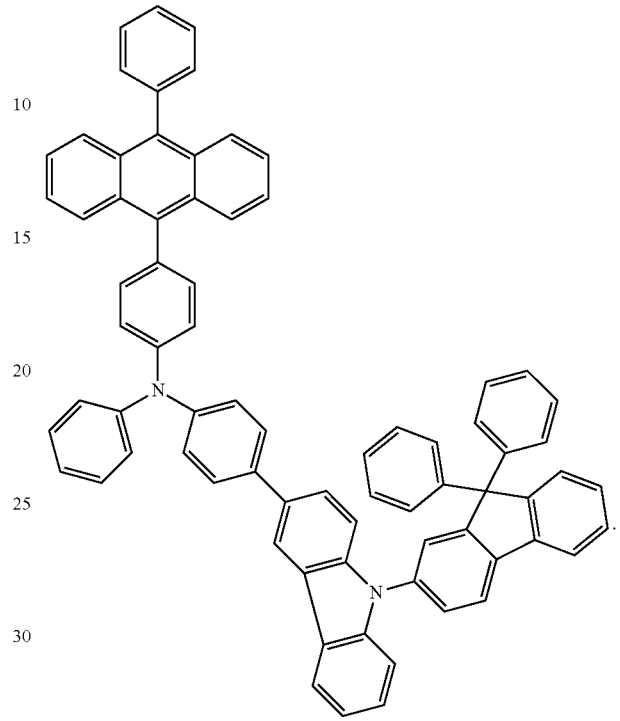

14. The anthracene derivative according to claim 10, wherein the anthracene derivative is represented by a structural formula (154), (154)

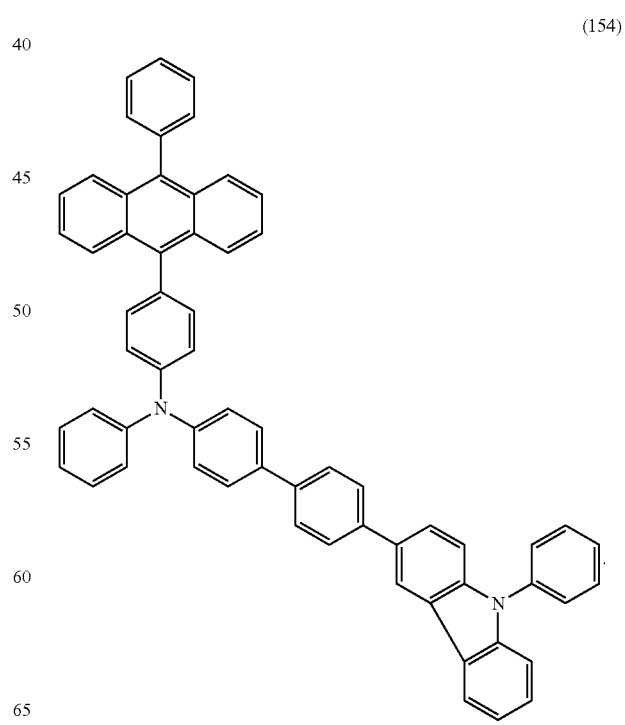

15. The anthracene derivative according to claim 10, wherein the anthracene derivative is represented by a structural formula (156),
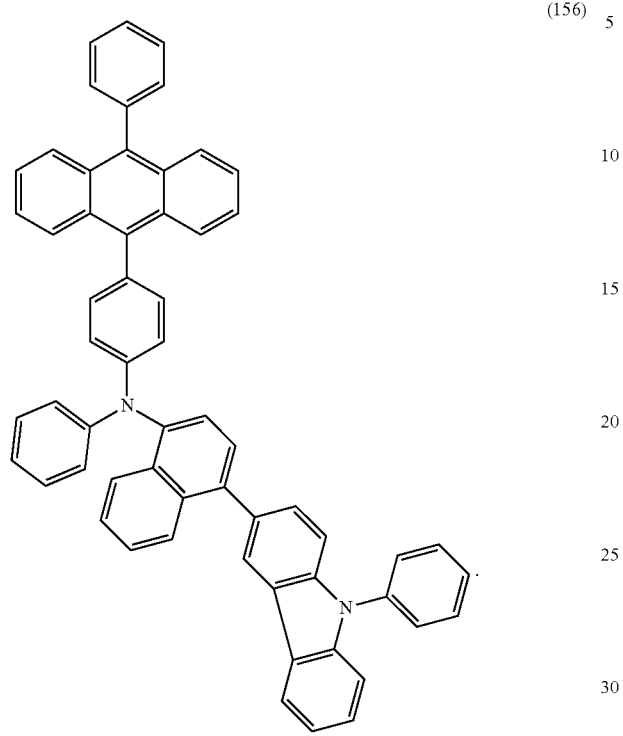
(156)
* * * * *

UNITED STATES PATENT AND TRADEMARK OFFICE
CERTIFICATE OF CORRECTION

PATENT NO.        : 8,835,018 B2                                    Page 1 of 1
APPLICATION NO.   : 12/055000
DATED             : September 16, 2014
INVENTOR(S)       : Sachiko Kawakami et al.

It is certified that error appears in the above-identified patent and that said Letters Patent is hereby corrected as shown below:

In the Specification:

Col. 1, line 26, "electroluninescent" should read --electroluminescent--.

Col. 1, line 43, "recombination that is" should read --recombination, that is--.

Col. 8, lines 46, "ha1oalkyl group" should read --haloalkyl group--.

Col. 14, line 60, "Further, a may" should read --Further, α may--.

Col. 55, lines 22-23, "ethyleneglycoldinethylether" should read
    --ethyleneglycoldimethylether--.

Col. 85, line 12, "mixture thereof or" should read --mixture thereof, or--.

Col. 86, line 37, "and the like" should read --and the like.--.

Col. 86, line 59, "t-BuAnth)," should read --t-BuDBA),--.

Col. 87, line 20, "poly[A-(4-{N'-[4-(4" should read --poly[N-(4-{N'-[4-(4--.

Col. 87, line 40, "4,4'4"-tis(N,N-" should read --4,4',4"-tris(N,N- --.

Col. 91, line 3, "high efficiency the" should read --high efficiency, the--.

Col. 91, line 47, "2,2'-bipyridin-6" should read --2,2'-bipyridine-6--.

Col. 93, line 38, "(YCAS2)," should read --(YGAS2),--.

Col. 94, lines 48-49, "abbreviated to CzA-lPA)," should read
    --abbreviated to CzAlpA),--.

Signed and Sealed this
Seventh Day of April, 2015

Michelle K. Lee
*Director of the United States Patent and Trademark Office*